US012406364B2

(12) United States Patent
Li

(10) Patent No.: US 12,406,364 B2
(45) Date of Patent: Sep. 2, 2025

(54) SYSTEMS AND METHODS FOR SPATIAL ANALYSIS OF ANALYTES USING FIDUCIAL ALIGNMENT

(71) Applicant: 10x Genomics, Inc., Pleasanton, CA (US)

(72) Inventor: Dongyao Li, San Jose, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 388 days.

(21) Appl. No.: 18/169,132

(22) Filed: Feb. 14, 2023

(65) Prior Publication Data
US 2023/0306593 A1    Sep. 28, 2023

Related U.S. Application Data

(60) Provisional application No. 63/310,242, filed on Feb. 15, 2022.

(51) Int. Cl.
*G06T 7/00*        (2017.01)
*G06T 3/02*        (2024.01)
(Continued)

(52) U.S. Cl.
CPC .............. *G06T 7/0012* (2013.01); *G06T 3/02* (2024.01); *G06T 3/20* (2013.01); *G06T 7/13* (2017.01);
(Continued)

(58) Field of Classification Search
CPC . G06T 2207/10056; G06T 2207/10064; G06T 2207/30024; G06T 7/33;
(Continued)

(56) References Cited

U.S. PATENT DOCUMENTS 7,709,198 B2    5/2010  Luo et al.
8,604,182 B2   12/2013  Luo et al.
(Continued)

FOREIGN PATENT DOCUMENTS

WO    WO 2018/091676 A1    5/2018
WO    WO 2020/053655 A1    3/2020
(Continued)

OTHER PUBLICATIONS

U.S. Appl. No. 63/080,547, entitled "Sample Handling Apparatus and Image Registration Methods," filed Sep. 18, 2020.
(Continued)

*Primary Examiner* — Zhiyu Lu

(57) ABSTRACT

Systems and methods for spatial analysis of analytes are provided. A data structure is obtained comprising an image, as an array of pixel values, of a sample on a substrate having intersecting border regions, fiducial markers encoding N-digit codes, and a set of capture spots, where at least two border regions includes a fiducial marker. The pixel values are analyzed to identify locations of fiducial markers. The locations are aligned with locations of reference fiducial markers in a template using an alignment algorithm to obtain a final transformation between the fiducial markers in the image and the reference fiducial markers in the template. The final transformation and a coordinate system of the template are used to register the image to the set of capture spots. The registered image is then analyzed in conjunction with spatial analyte data associated with each capture spot, thereby performing spatial analysis of analytes.

20 Claims, 30 Drawing Sheets

(51) Int. Cl.
*G06T 3/20* (2006.01)
*G06T 7/13* (2017.01)
*G06T 7/168* (2017.01)
*G06T 7/33* (2017.01)

(52) U.S. Cl.
CPC .............. *G06T 7/168* (2017.01); *G06T 7/337* (2017.01); *G06T 2207/10056* (2013.01); *G06T 2207/30024* (2013.01); *G06T 2207/30204* (2013.01)

(58) Field of Classification Search
CPC . G06T 2207/10024; G06T 2207/20104; G06T 2207/30072; G06T 2207/30204; G06T 3/02; G06T 3/20; G06T 7/0012; G06T 7/13; G06T 7/168; G06T 7/337; C12Q 1/6837
See application file for complete search history.

(56) References Cited

U.S. PATENT DOCUMENTS

| | | | |
|---|---|---|---|
| 8,951,726 | B2 | 2/2015 | Luo et al. |
| 9,012,022 | B2 | 4/2015 | George et al. |
| 9,593,365 | B2 | 3/2017 | Frisen et al. |
| 9,727,810 | B2 | 8/2017 | Fodor et al. |
| 9,783,841 | B2 | 10/2017 | Nolan et al. |
| 9,879,313 | B2 | 1/2018 | Chee et al. |
| 10,002,316 | B2 | 6/2018 | Fodor et al. |
| 10,041,949 | B2 | 8/2018 | Bendall et al. |
| 10,059,990 | B2 | 8/2018 | Boyden et al. |
| 10,480,022 | B2 | 11/2019 | Chee |
| 10,724,078 | B2 | 7/2020 | van Driel et al. |
| 10,774,374 | B2 | 9/2020 | Frisen et al. |
| 11,501,440 | B2 | 11/2022 | Weisenfeld et al. |
| 11,514,575 | B2 | 11/2022 | Mellen et al. |
| 2011/0059865 | A1 | 3/2011 | Smith et al. |
| 2013/0171621 | A1 | 7/2013 | Luo et al. |
| 2015/0000854 | A1 | 1/2015 | Gann-Fetter et al. |
| 2016/0108458 | A1 | 4/2016 | Frei et al. |
| 2017/0016053 | A1 | 1/2017 | Beechem et al. |
| 2017/0029875 | A1 | 2/2017 | Zhang et al. |
| 2017/0067096 | A1 | 3/2017 | Wassie et al. |
| 2017/0089811 | A1 | 3/2017 | Tillberg et al. |
| 2017/0241911 | A1 | 8/2017 | Rockel et al. |
| 2018/0051322 | A1 | 2/2018 | Church et al. |
| 2018/0216161 | A1 | 8/2018 | Chen et al. |
| 2018/0245142 | A1 | 8/2018 | So et al. |
| 2019/0055594 | A1 | 2/2019 | Samusik et al. |
| 2019/0085383 | A1 | 3/2019 | Church et al. |
| 2019/0161796 | A1 | 5/2019 | Hauling et al. |
| 2019/0194709 | A1 | 6/2019 | Church et al. |
| 2019/0264268 | A1 | 8/2019 | Firisen et al. |
| 2019/0330617 | A1 | 10/2019 | Church et al. |
| 2020/0024641 | A1 | 1/2020 | Nolan et al. |
| 2020/0077663 | A1 | 3/2020 | Clube et al. |
| 2020/0080136 | A1 | 3/2020 | Zhang et al. |
| 2020/0224244 | A1 | 7/2020 | Nilsson et al. |
| 2020/0239946 | A1 | 7/2020 | Dewal |
| 2020/0256867 | A1 | 8/2020 | Hennek et al. |
| 2020/0277664 | A1* | 9/2020 | Frenz .................... G02B 21/365 |
| 2021/0062272 | A1 | 3/2021 | Williams et al. |
| 2021/0150707 | A1 | 5/2021 | Weisenfeld et al. |
| 2021/0155982 | A1 | 5/2021 | Yin et al. |
| 2022/0412872 | A1* | 12/2022 | Nareid ............... G01N 15/1436 |
| 2023/0017773 | A1 | 1/2023 | Kim et al. |

FOREIGN PATENT DOCUMENTS

| | | |
|---|---|---|
| WO | WO 2020/061066 A1 | 3/2020 |
| WO | WO 2020/061108 A1 | 3/2020 |
| WO | WO 2020/123320 A2 | 6/2020 |
| WO | WO 2021/252747 A1 | 12/2021 |
| WO | WO 2022/061150 A2 | 3/2022 |

OTHER PUBLICATIONS

Achim et al., 2015, "High-throughput spatial mapping of single-cell RNA-seq data to tissue of origin," Nature Biotechnology 33: 503-509.
Calvet, L., et al., "Detection and Accurate Localizsation of Circular Fiducils under Highly Challengin Conditiosn," CVPR Paper, 2016.
Carter et al., *Applied Optics* 46:421-427, 2007.
Chen et al., *Science* 348(6233):aaa6090, 2015.
Chetverikov et al., 2002, "The Trimmed Iterative Closest Point Algorithm," Object recognition supported by user interaction for service robots, Quebec City, Quebec, Canada, ISSN: 1051-4651.
Chetverikov et al., 2005, "Robust Euclidean alignment of 3D point sets; the trimmed iterative closest point algorithm," Image and Vision Computing 23(3), pp. 299-309.
Chu et al., 2020, "Sub-pixel dimensional measurement algorithm based on intensity integration threshold," OSA Continuum 3(10): 2912.
Chui and Rangarajanb, 2003, "A new point matching algorithm for non-rigid registration," Computer Vision and Image Understanding 89(2-3), pp. 114-141.
Gatti and Khallaghi, 2022, "PyCPD: Pure NumPy Implementation of the Coherent Point Drift Algorithm," Journal of Open Source Software 7(80), p. 4681.
Gao et al., BMC Biol. 15:50, 2017.
Gupta et al., Nature Biotechnol. 36:1197-1202, 2018.
Hassanein et al., 2015, "A Survey of Hough Transform, Theory, Techniques and Applications," ArXiv:1502.02160.
Kaur and Kant, 2014, "A Review on Comparison and Analysis of Edge Detection Techniques," IJRECE 2(1): 38-41.
Lee et al., Nat. Protoc. 10(3):442-458, 2015.
Myronenko et al., 2007, "Non-rigid point set registration: Coherent Point Drift," NIPS, 1009-1016.
Myronenko and Song, "Point Set Registration: Coherent Point Drift," arXiv:0905.2635v1, May 15, 2009.
Pedersen, 2009, "Circular Hough Transform," Encyclopedia of Biometrics.
Rodriques et al., Science 363(6434):1463-1467, 2019.
Satija et al., 2015, "Spatial reconstruction of single-cell gene expression data," Nature Biotechnology. 33, 495-502.
Trejo et al., PLoS ONE 14(2):e0212031, 2019.
Uchida, 2013, "Image processing and recognition for biological images," Develop. Growth Differ. 55, 523-549.
Yang, 2011, "The thin plate spline robust point matching (TPS-RPM) algorithm: A revisit," Pattern Recognition Letters 32(7), pp. 910-918.
Zhai, 2001, "Making GenePix Array List (GAL) Files," GenePix Application Note, Molecular Devices, pp. 1-9.

* cited by examiner

200 — A method of spatial analysis of analytes.

202 — Obtain a data structure in electronic form comprising an image of a sample on a substrate. The substrate includes a plurality of border regions, where each respective border region in the plurality of border regions intersects another border region in the plurality of border regions.

The substrate includes at least a first plurality of fiducial markers, where the first plurality of fiducial markers comprises at least three fiducial markers. Each respective fiducial marker in the first plurality of fiducial markers encodes a different N-digit code, in a plurality of N-digit codes, where N is an integer greater than 3. At least two different border regions in the plurality of border regions includes a respective fiducial marker in the first plurality of fiducial markers.

The substrate includes a set of capture spots, where the set of capture spots comprises at least 1000 capture spots. The image comprises a plurality of pixel values, each respective pixel value in the plurality of pixel values corresponding to a pixel in an array of pixels, where the array of pixels comprises at least 100,000 pixels.

204 — The image is acquired using transmission light microscopy or fluorescent microscopy.

206 — The sample is a sectioned tissue sample and wherein the sectioned tissue sample has a depth of 30 microns or less.

208 — The sample is a sectioned tissue sample, each respective capture spot in the set of capture spots is (i) at a different position in a two-dimensional array and (ii) associates with one or more analytes from the sectioned tissue sample, and each respective capture spot in the set of capture spots is characterized by at least one unique spatial barcode in a plurality of spatial barcodes.

210 — The one or more analytes are nucleic acids, RNA, DNA, or proteins.

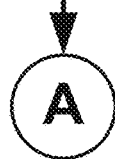

Figure 2A

SYSTEMS AND METHODS FOR SPATIAL ANALYSIS OF ANALYTES USING FIDUCIAL ALIGNMENT

CROSS REFERENCE TO RELATED PATENT APPLICATIONS

This application claims priority to U.S. Provisional patent application No. 63/310,242, entitled "SYSTEMS AND METHODS FOR SPATIAL ANALYSIS USING FIDUCIAL ALIGNMENT," filed Feb. 15, 2022, which is hereby incorporated by reference.

TECHNICAL FIELD

This specification describes technologies relating to processing observed analyte data in large, complex datasets, such as spatially arranged next generation sequencing data.

BACKGROUND

Spatial resolution of analytes in complex tissues provides new insights into the processes underlying biological function and morphology, such as cell fate and development, disease progression and detection, and cellular and tissue-level regulatory networks. See, Satija et al., 2015, "Spatial reconstruction of single-cell gene expression data," Nature Biotechnology. 33, 495-502, doi:10.1038.nbt.3192 and Achim et al., 2015, "High-throughput spatial mapping of single-cell RNA-seq data to tissue of origin," Nature Biotechnology 33: 503-509, doi:10.1038/nbt.3209, each of which is hereby incorporated herein by reference in its entirety.

An understanding of the spatial patterns or other forms of relationships between analytes can provide information on differential cell behavior. This, in turn, can help to elucidate complex conditions such as complex diseases. For example, the determination that the abundance of an analyte (e.g., a gene product) is associated with a tissue subpopulation of a particular tissue class (e.g., disease tissue, healthy tissue, the boundary of disease and healthy tissue, etc.) provides inferential evidence of the association of the analyte with a condition such as complex disease. Likewise, the determination that the abundance of an analyte is associated with a particular subpopulation of a heterogeneous cell population in a complex 2-dimensional or 3-dimensional tissue (e.g., a mammalian brain, liver, kidney, heart, a tumor, organoid, or a developing embryo of a model organism) provides inferential evidence of the association of the analyte to the particular subpopulation.

Thus, spatial analysis of analytes can provide information for the early detection of disease by identifying at-risk regions in complex tissues and characterizing the analyte profiles present in these regions through spatial reconstruction (e.g., of gene expression, protein expression, DNA methylation, copy number variation, and/or single nucleotide polymorphisms, among others). A high-resolution spatial mapping of analytes to their specific location within a region or subregion reveals spatial expression patterns of analytes, provides relational data, and further implicates analyte network interactions relating to disease or other morphologies or phenotypes of interest, resulting in a holistic understanding of cells in their morphological context.

SUMMARY

Technical solutions (e.g., computing systems, methods, and non-transitory computer readable storage mediums) for spatial analysis of analytes are provided in the present disclosure.

The following presents a summary of the present disclosure in order to provide a basic understanding of some of the aspects of the present disclosure. This summary is not an extensive overview of the present disclosure. It is not intended to identify key/critical elements of the present disclosure or to delineate the scope of the present disclosure. Its sole purpose is to present some of the concepts of the present disclosure in a simplified form as a prelude to the more detailed description that is presented later.

One aspect of the present disclosure provides a method for spatial analysis of analytes, the method comprising obtaining a data structure, in electronic form, comprising an image of a sample on a substrate, where the substrate includes a plurality of border regions, where each respective border region in the plurality of border regions intersects another border region in the plurality of border regions. The substrate includes at least a first plurality of fiducial markers, the first plurality of fiducial markers comprises at least three fiducial markers, and each respective fiducial marker in the first plurality of fiducial markers encodes a different N-digit code, in a plurality of N-digit codes, where N is an integer greater than 3. At least two different border regions in the plurality of border regions includes a respective fiducial marker in the first plurality of fiducial markers, the substrate includes a set of capture spots, where the set of capture spots comprises at least 1000 capture spots, and the image comprises a plurality of pixel values, each respective pixel value in the plurality of pixel values corresponding to a pixel in an array of pixels, wherein the array of pixels comprises at least 100,000 pixels.

The method includes analyzing the plurality of pixel values to identify a respective location of each fiducial marker in the first plurality of fiducial markers within the image. The respective location of each fiducial marker in the first plurality of fiducial markers within the image is aligned with a location of each reference fiducial marker in a plurality of reference fiducial markers of a first template using an alignment algorithm to obtain a final transformation between the first plurality of fiducial markers of the image and the plurality of reference fiducial markers of the first template. The final transformation and a coordinate system of the first template are used to register the image to the set of capture spots. The image is then analyzed in conjunction with spatial analyte data associated with each capture spot, thereby performing spatial analysis of analytes.

In some embodiments, the plurality of border regions consists of four border regions, the first plurality of fiducial markers comprises a plurality of subsets of fiducial markers, and each respective border region in the plurality of border regions is associated with a respective subset of fiducial markers in the plurality of subsets of fiducial markers. In some such embodiments, each respective fiducial marker in the first plurality of fiducial markers has a different pattern in a plurality of patterns, the plurality of patterns comprises more than 5, 10, 20, 30, 40, or 50 patterns, and each pattern in the plurality of patterns encodes a different N-digit code in the plurality of N-digit codes. In some such embodiments, each respective fiducial marker in the first plurality of fiducial markers has a different pattern in a plurality of patterns, the plurality of patterns consists of between 20 and 400 patterns, and each pattern in the plurality of patterns encodes a different N-digit code in the plurality of N-digit codes.

In some embodiments, each respective pattern in the plurality of patterns is a different concentric closed-form arrangement. In some embodiments, each different concentric closed-form arrangement is a different concentric circular pattern.

In some embodiments, each fiducial marker in the first plurality of fiducial markers has a width of between 0.001 microns and 25 microns.

In some embodiments, each respective pattern in the plurality of patterns comprises a different pattern of at least three rings and at least two inter-ring spacings, each ring of each respective pattern in the plurality of patterns is characterized by a respective linewidth in a set of at least three discrete linewidths, each of the at least two inter-ring spacings of each respective pattern in the plurality of patterns is characterized by one of at least three different inter-ring spacing widths, and a respective linewidth of each respective ring in the at least three rings of a respective pattern in the plurality of patterns together with a respective inter-ring spacing of each of the at least two inter-ring spacings of the respective pattern collectively encode at least a five bit ternary code that localizes the corresponding fiducial marker to a particular position on the substrate in accordance with the first template.

In some embodiments, the analyzing the plurality of pixel values to identify a respective location of each fiducial marker in the first plurality of fiducial markers within the image comprises identifying a first plurality of edges in the plurality of pixel values; filtering the first plurality of edges to identify a second plurality of edges from the first plurality of edges, where each edge in the second plurality of edges is a member of an edge-group of length six in a plurality of edge-groups of length six in the second plurality of edges; and identifying a respective fiducial center candidate using a circle Hough transform of each respective edge-group of length six in the plurality of edge-groups of length six, thereby identifying a plurality of fiducial center candidates, where each respective fiducial center candidate in the plurality of fiducial center candidates is associated with a pixel in the array of pixels. In some embodiments, the analyzing the plurality of pixel values further includes identifying a plurality of fiducial centers from the plurality of fiducial center candidates by applying a threshold requirement to each fiducial center candidate in the plurality of fiducial center candidates; associating each respective edge-group of length six in the plurality of edge-groups of length six with a corresponding fiducial center in the plurality of fiducial centers based at least on a proximity of the respective edge-group of length six to the corresponding fiducial center; arranging, for each respective edge-group of length six in the plurality of edge-groups of length six, each edge in the respective edge-group of link six with respect to the fiducial center associated with the respective edge-group to form a corresponding ordered set of edges for each fiducial marker in the first plurality of fiducial markers, thereby forming a respective ordered set of concentric circles about each respective fiducial center in the plurality of fiducial centers; and determining, for each respective fiducial marker in the plurality of fiducial markers, the at least five bit ternary code of the fiducial marker from a radius of each concentric circle in the respective ordered set of concentric circles about the fiducial center of the respective fiducial marker.

In some embodiments, the identifying the first plurality of edges in the array of pixel values is performed using Sobel edge detection, and the filtering the first plurality of edges comprises determining a corresponding normal of a tangent of a respective edge in the first plurality of edges by fitting the respective edge with a polynomial line and using a corresponding normal of the polynomial line to identify edges in the first plurality of edges that are a member of an edge-group common to the respective edge.

In some embodiments, the fitting the respective edge with a polynomial line is performed at sub-pixel resolution.

In some embodiments, the first plurality of fiducial markers comprise titanium, chromium, platinum, tantalum, gold, a combination thereof, and/or an alloy thereof. In some embodiments, the first plurality of fiducial markers have a thickness (e.g., vertical thickness, vertical deposition thickness) of between 10 nm and 50 nm. In some embodiments, the first plurality of fiducial markers have a thickness of between 40 nm and 300 nm.

In some embodiments, the alignment algorithm is a linear regression.

In some embodiments, the analyzing the plurality of pixel values is performed on (i) a two-dimensional affine transformation of the array of pixel values and (ii) the two-dimensional affine transformation taking mirroring into consideration; the alignment algorithm computes a first residual value based on the respective location of each fiducial marker in the first plurality of fiducial markers within the two-dimensional affine transformation of the array of pixel values and a second residual value based on the respective location of each fiducial marker in the first plurality of fiducial markers within the two-dimensional affine transformation taking mirroring into consideration; and the alignment algorithm selects between the image and a mirror image of the image to compute the final transformation based on a comparison of the first and second residual value.

In some embodiments, the final transformation includes a similarity transform that comprises rotation, translation, and isotropic scaling of the first plurality of fiducial markers of the image to minimize a residual error between the first plurality of fiducial markers of the image and the corresponding plurality of reference fiducial markers. In some embodiments, the final transformation includes a perspective transform.

In some embodiments, the sample is a sectioned tissue sample (e.g., a tissue section), each respective capture spot in the set of capture spots is (i) at a different position in a two-dimensional array and (ii) associates with one or more analytes from the sectioned tissue sample, and each respective capture spot in the set of capture spots is characterized by at least one unique spatial barcode in a plurality of spatial barcodes. In some embodiments, a capture spot in the set of capture spots comprises a capture domain. In some embodiments, a capture spot in the set of capture spots comprises a cleavage domain. In some embodiments, each capture spot in the set of capture spots is attached directly or attached indirectly (e.g., via a linker) to the substrate.

In some embodiments, the one or more analytes comprise five or more distinct (e.g., different) analytes, ten or more distinct (e.g., different) analytes, fifty or more distinct (e.g., different) analytes, one hundred or more distinct (e.g., different) analytes, five hundred or more distinct (e.g., different) analytes, 1000 or more distinct (e.g., different) analytes, 2000 or more distinct (e.g., different) analytes, or between 2000 and 10,000 distinct (e.g., different) analytes. For example, in some embodiments the one or more analytes comprise five or more distinct mRNAs of a transcriptome.

In some embodiments, the unique spatial barcode encodes a unique predetermined value selected from the set $\{1, \ldots, 1024\}$, $\{1, \ldots, 4096\}$, $\{1, \ldots, 16384\}$, $\{1, \ldots, 65536\}$, $\{1, \ldots, 262144\}$, $\{1, \ldots, 1048576\}$, $\{1, \ldots, 4194304\}$, $\{1, \ldots, 16777216\}$, $\{1, \ldots, 67108864\}$, or $\{1, \ldots, 1 \times 10^{12}\}$.

In some embodiments, each respective capture spot in the set of capture spots includes 1000 or more capture probes, 2000 or more capture probes, 10,000 or more capture probes, 100,000 or more capture probes, $1 \times 10^6$ or more capture probes, $2 \times 10^6$ or more capture probes, $5 \times 10^6$ capture probes, or $1 \times 10^7$ or more capture probes. In some embodiments, each capture probe in the respective capture spot includes a poly-A sequence or a poly-T sequence and a unique spatial barcode that characterizes the respective capture spot. In some embodiments, each capture probe in the respective capture spot includes the same spatial barcode from the plurality of spatial barcodes. In some embodiments, each capture probe in the respective capture spot includes a different spatial barcode from the plurality of spatial barcodes.

In some embodiments, the sample is a sectioned tissue sample and the sectioned tissue sample has a depth of 30 microns or less.

In some embodiments, the one or more analytes is a plurality of analytes; a respective capture spot in the set of capture spots includes a plurality of capture probes, each probe in the plurality of capture probes including a capture domain that is characterized by a capture domain type in a plurality of capture domain types; and each respective capture domain type in the plurality of capture domain types is configured to bind to a different analyte in the plurality of analytes.

In some embodiments, the plurality of capture domain types comprises between 5 and 15,000 capture domain types and the respective capture spot includes at least five, at least 10, at least 100, or at least 1000 capture probes for each capture domain type in the plurality of capture domain types. In some embodiments, the plurality of capture domain types comprise gene-specific capture domains.

In some embodiments, the one or more analytes is a plurality of analytes, and a respective capture spot in the set of capture spots includes a plurality of capture probes, each capture probe in the plurality of capture probes including a capture domain that is characterized by a single capture domain type configured to bind to each analyte in the plurality of analytes in an unbiased manner.

In some embodiments, each respective capture spot in the set of capture spots is contained within a 10 micron by 10 micron square on the substrate. In some embodiments, a distance between a center of each respective capture spot to a neighboring capture spot in the set of capture spots on the substrate is between 4 microns and 8 microns. In some embodiments, a shape of each capture spot in the set of capture spots on the substrate is a closed-form shape. In some embodiments, the closed-form shape is circular and each capture spot in the set of capture spots has width of between 3 microns and 7 microns. In some embodiments, the closed-form shape is square and each capture spot in the set of capture spots has width of between 6 microns and 10 microns.

In some embodiments, the image is acquired using transmission light microscopy or fluorescent microscopy.

In some embodiments, the spatial analyte data associated with each capture spot is nucleic acid sequencing data associated with each capture spot. In some embodiments, the one or more analytes are nucleic acids, RNA, DNA, or proteins.

In some embodiments, the set of capture spots comprises at least 10,000 capture spots, at least 100,000 capture spots, at least 500,000 capture spots, at least $1 \times 10^6$ capture spots, at least at least $2 \times 10^6$ capture spots, at least at least $3 \times 10^6$ capture spots, or at least at least $4 \times 10^6$ capture spots.

In some embodiments, the substrate further comprises one or more glyphs at a first corner of the substrate. In some embodiments, the substrate is rectangular and further comprises one or more glyphs at each corner of the substrate. In some embodiments, the substrate is square, planar, and further comprises one or more glyphs at each corner of the substrate.

Another aspect of the present disclosure provides a computer system including one or more processors and memory storing one or more programs for spatial analysis of analytes. It will be appreciated that this memory can be on a single computer, a network of computers, one or more virtual machines, or in a cloud computing architecture. The one or more programs are configured for execution by the one or more processors. The one or more programs include instructions for performing any of the methods disclosed herein.

Still another aspect of the present disclosure provides a computer readable storage medium storing one or more programs to be executed by an electronic device. The one or more programs include instructions for the electronic device to perform spatial analysis of analytes by any of the methods disclosed herein. It will be appreciated that the computer readable storage medium can exist as a single computer readable storage medium or any number of component computer readable storage mediums that are physically separated from each other.

Other embodiments are directed to systems, portable consumer devices, and computer readable media associated with methods described herein.

As disclosed herein, any embodiment disclosed herein when applicable can be applied to any aspect.

Various embodiments of systems, methods, and devices within the scope of the appended claims each have several aspects, no single one of which is solely responsible for the desirable attributes described herein. Without limiting the scope of the appended claims, some prominent features are described herein. After considering this discussion, and particularly after reading the section entitled "Detailed Description" one will understand how the features of various embodiments are used.

INCORPORATION BY REFERENCE

All publications, patents, patent applications, and information available on the Internet and mentioned in this specification are herein incorporated by reference to the same extent as if each individual publication, patent, patent application, or item of information was specifically and individually indicated to be incorporated by reference. To the extent publications, patents, patent applications, or item of information available on the Internet incorporated by reference contradict the disclosure contained in the specification, the specification is intended to supersede and/or take precedence over any such contradictory material.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

FIGS. 2A, 2B, 2C, 2D, 2E, 2F, 2G, 2H, and 2I illustrate non-limiting methods for spatial analysis of analytes in accordance with some embodiments of the present disclosure, in which optional steps are illustrated by dashed line boxes.

FIGS. 4A, 4B, 4C, 4D, 4E, 4F, 4G, 411, 41, 4J, and 4K collectively show exemplary schematics for analyzing a plurality of pixel values to identify a respective location of a respective fiducial marker, in accordance with some embodiments of the present disclosure.

DETAILED DESCRIPTION

Introduction

Figure 1:
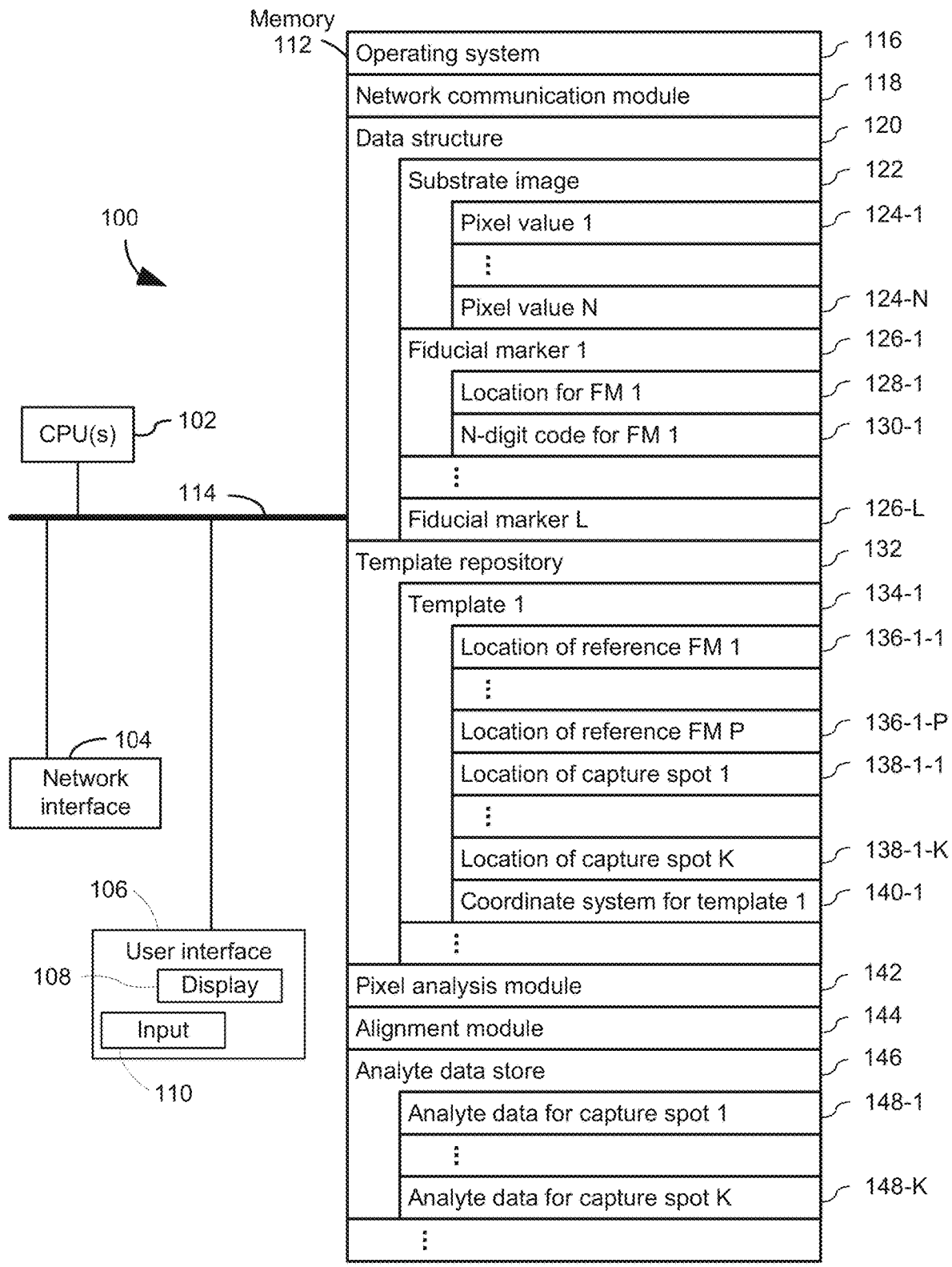
FIG. 1 shows an exemplary spatial analysis workflow in accordance with an embodiment of the present disclosure.
Figure 2B:
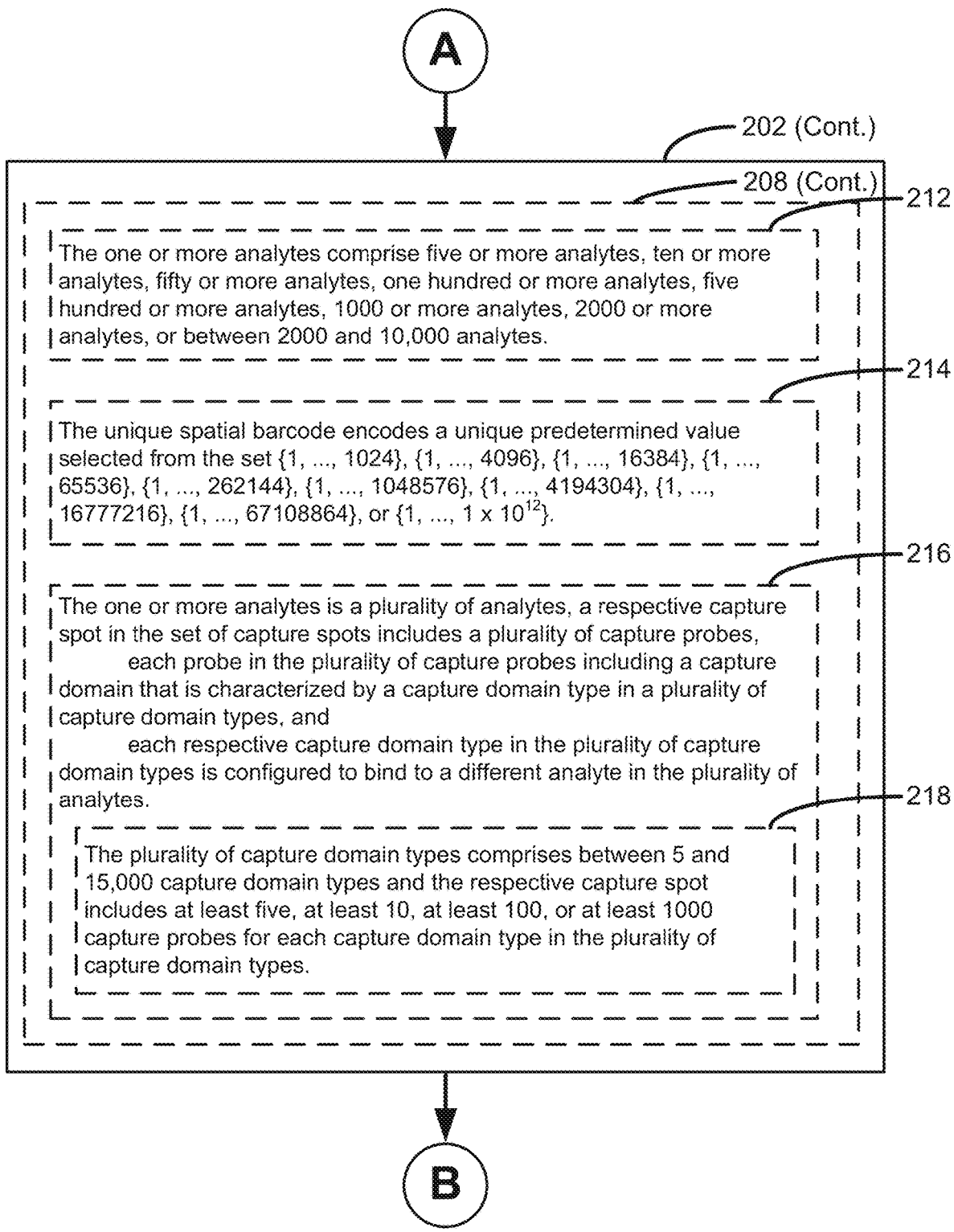
Figure 2C:
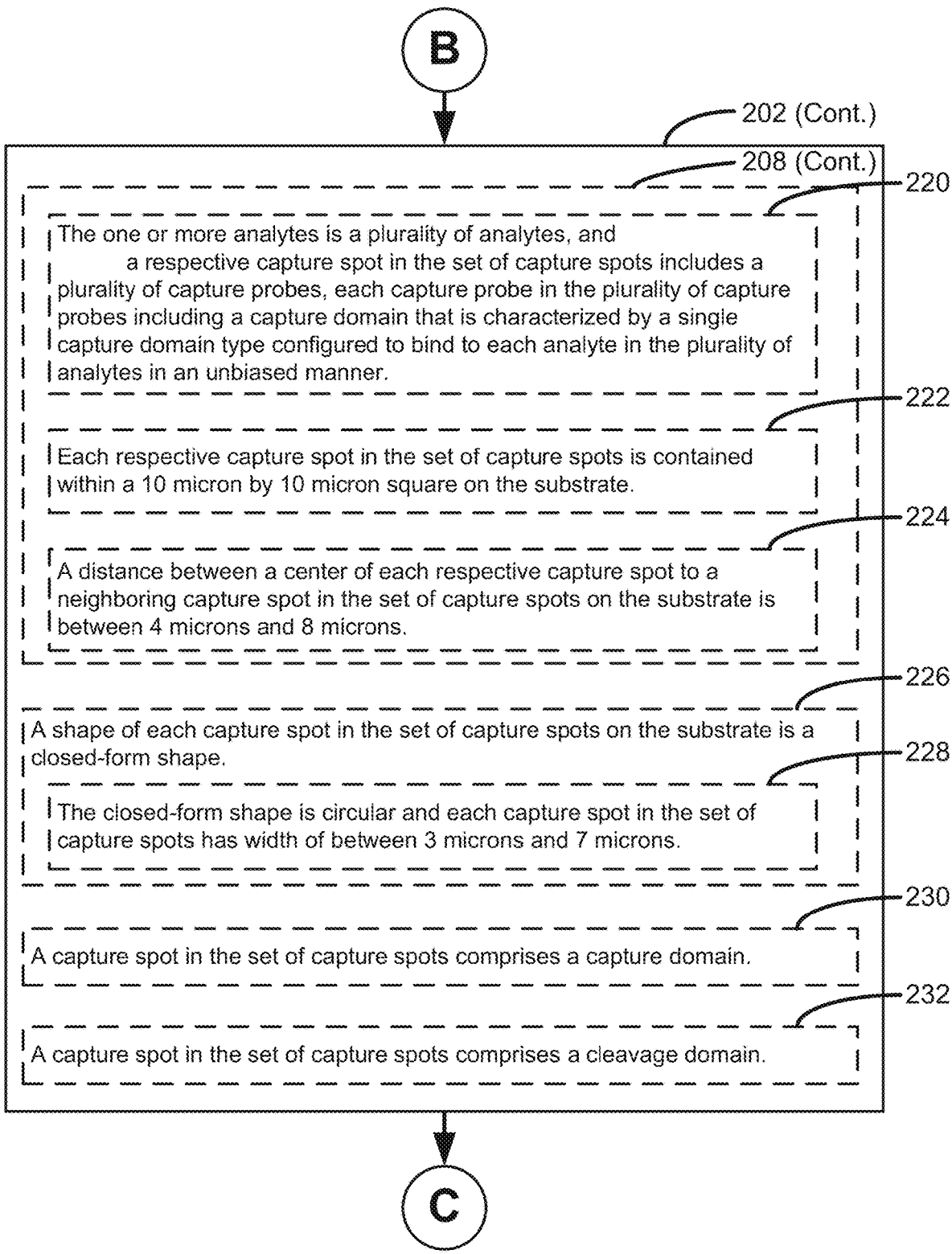
Figure 2D:
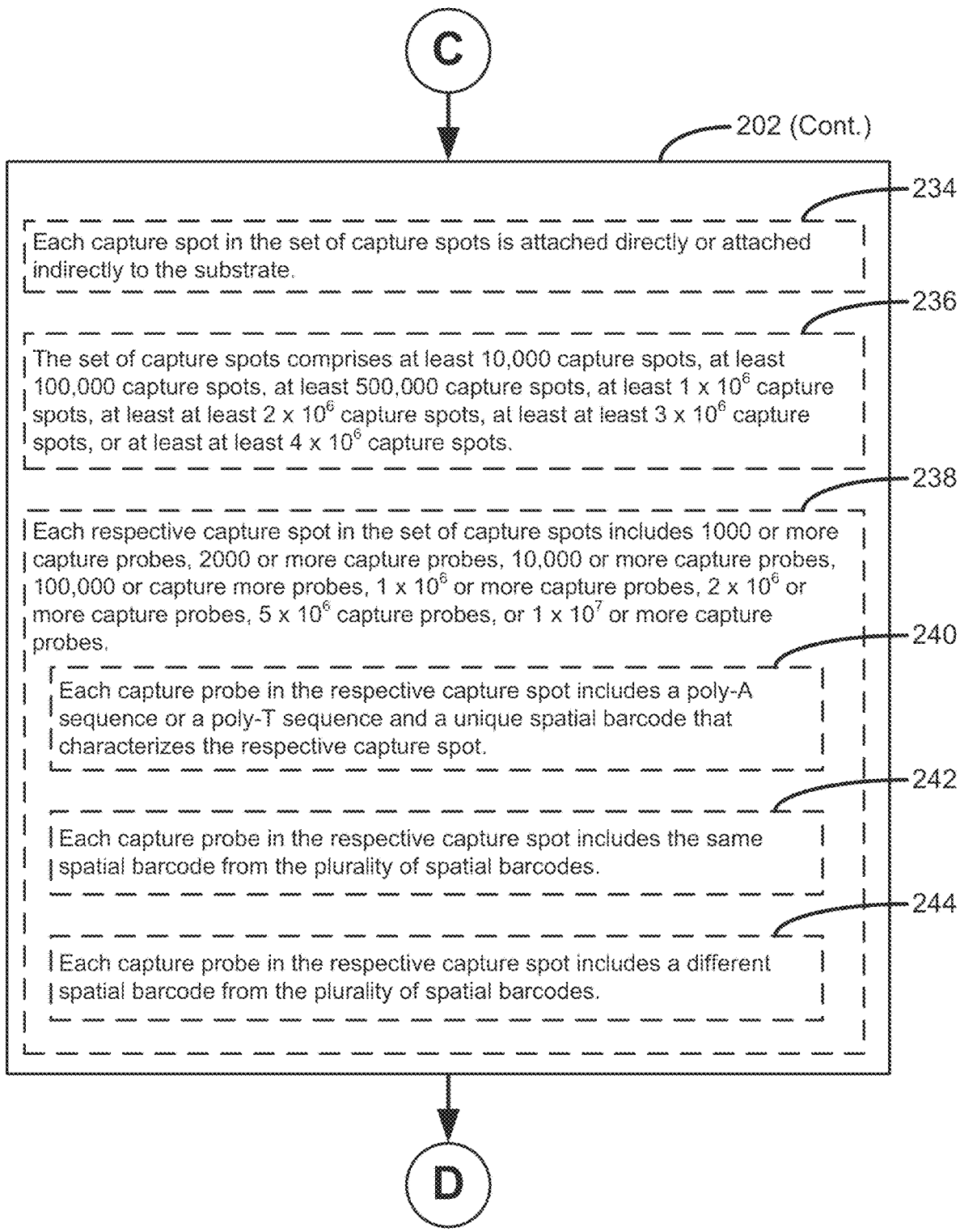
Figure 2E:
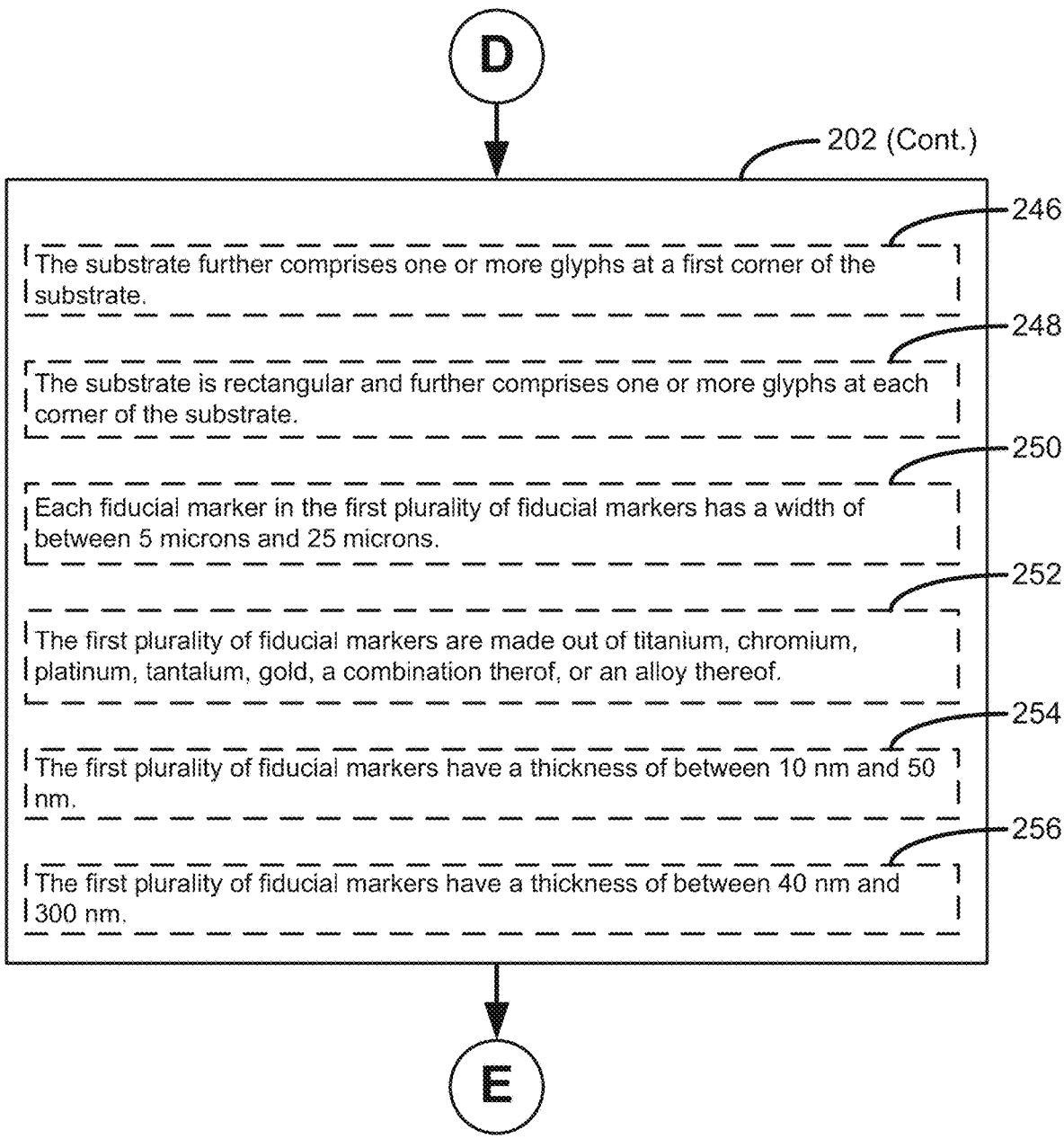
Figure 2F:
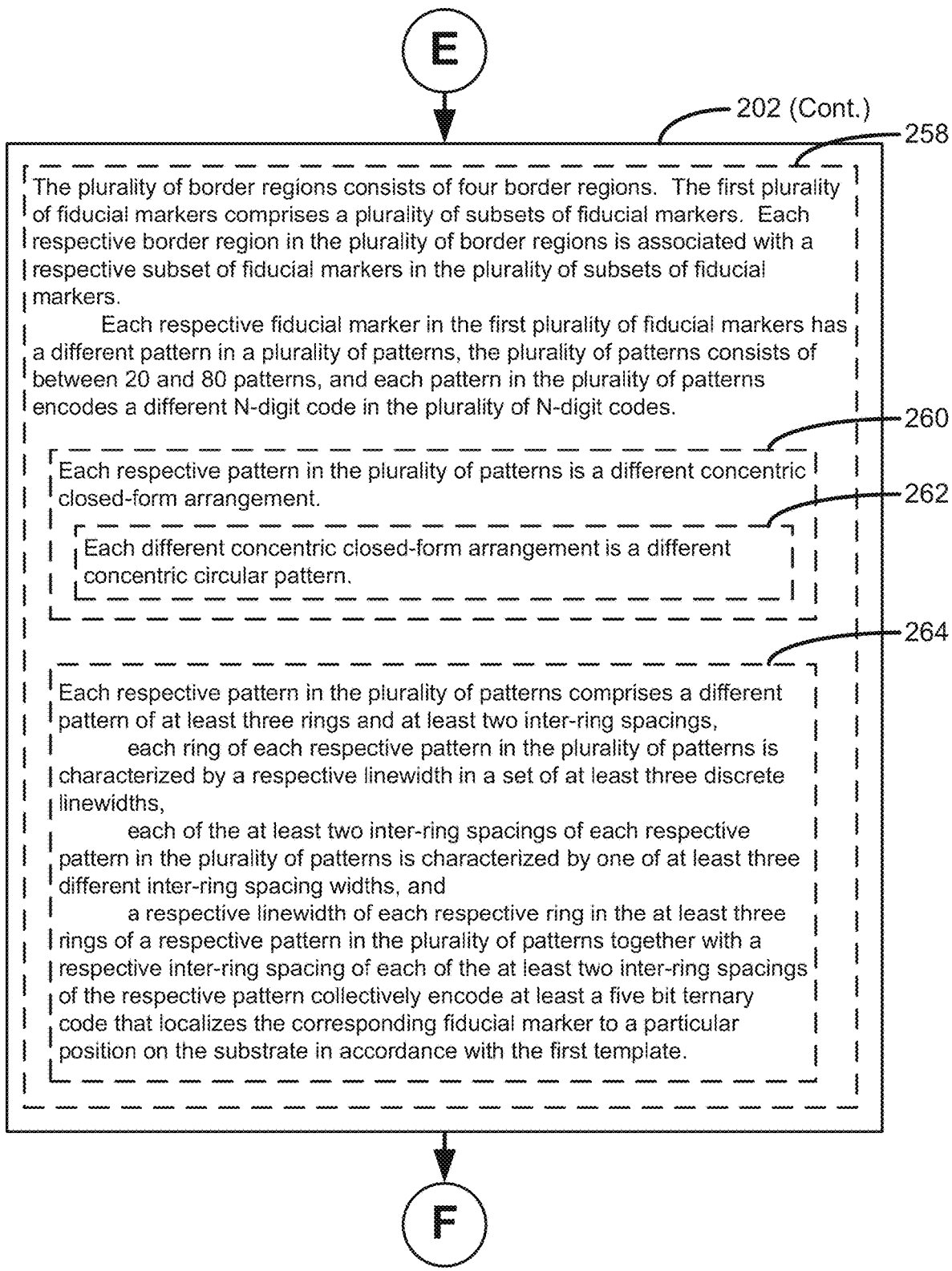
Figure 2G:
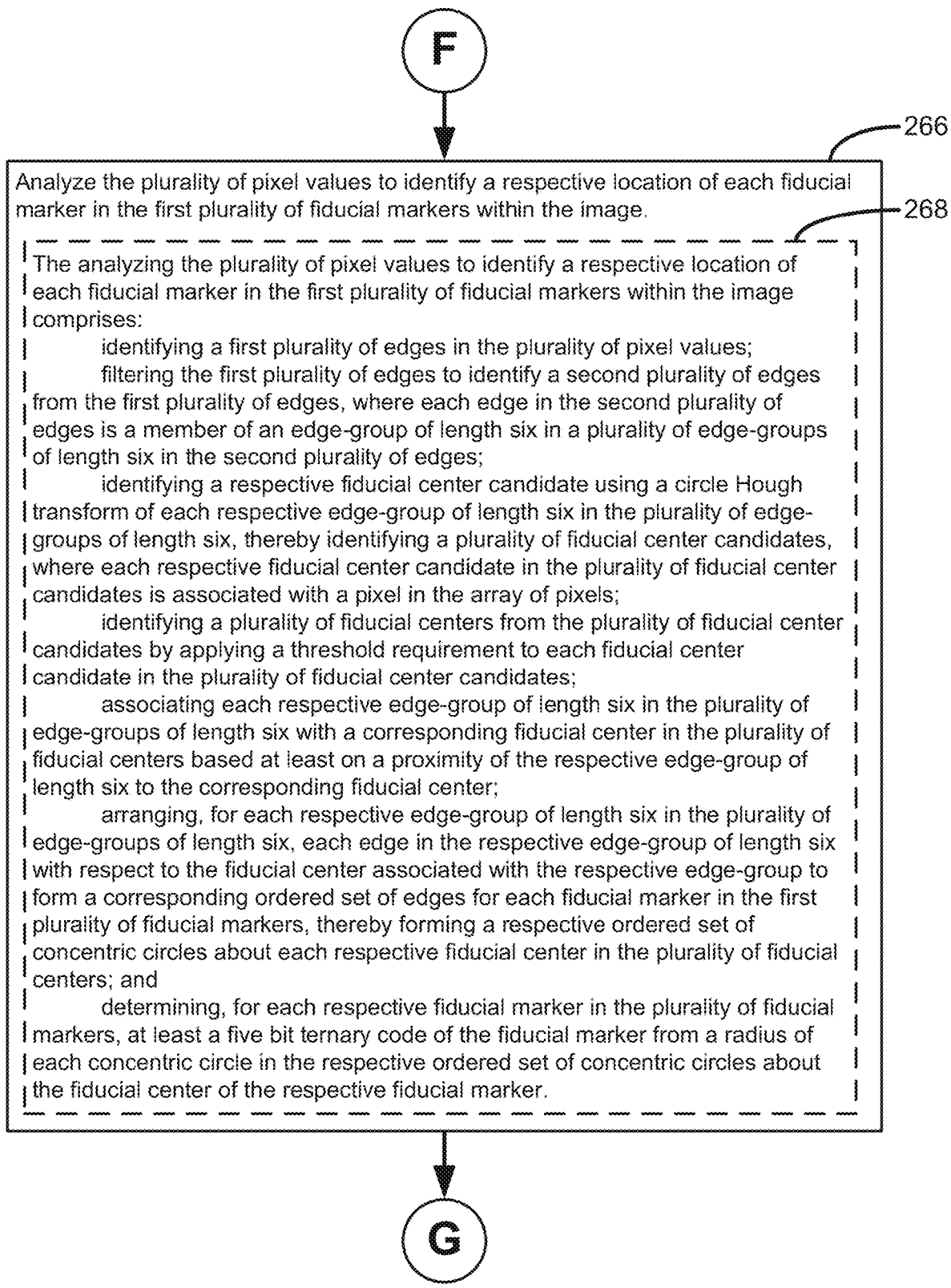
Figure 2H:
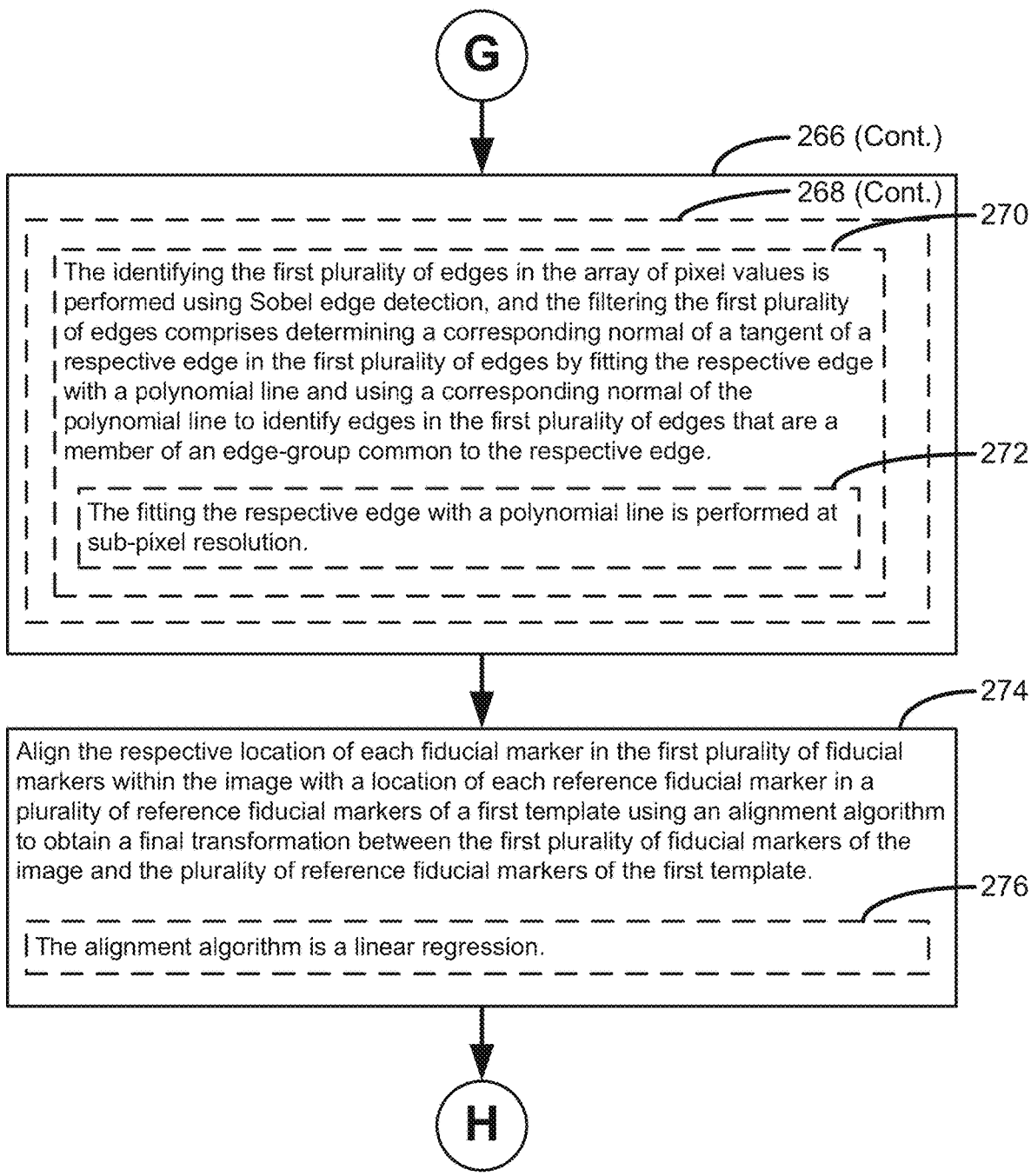
Figure 2I:
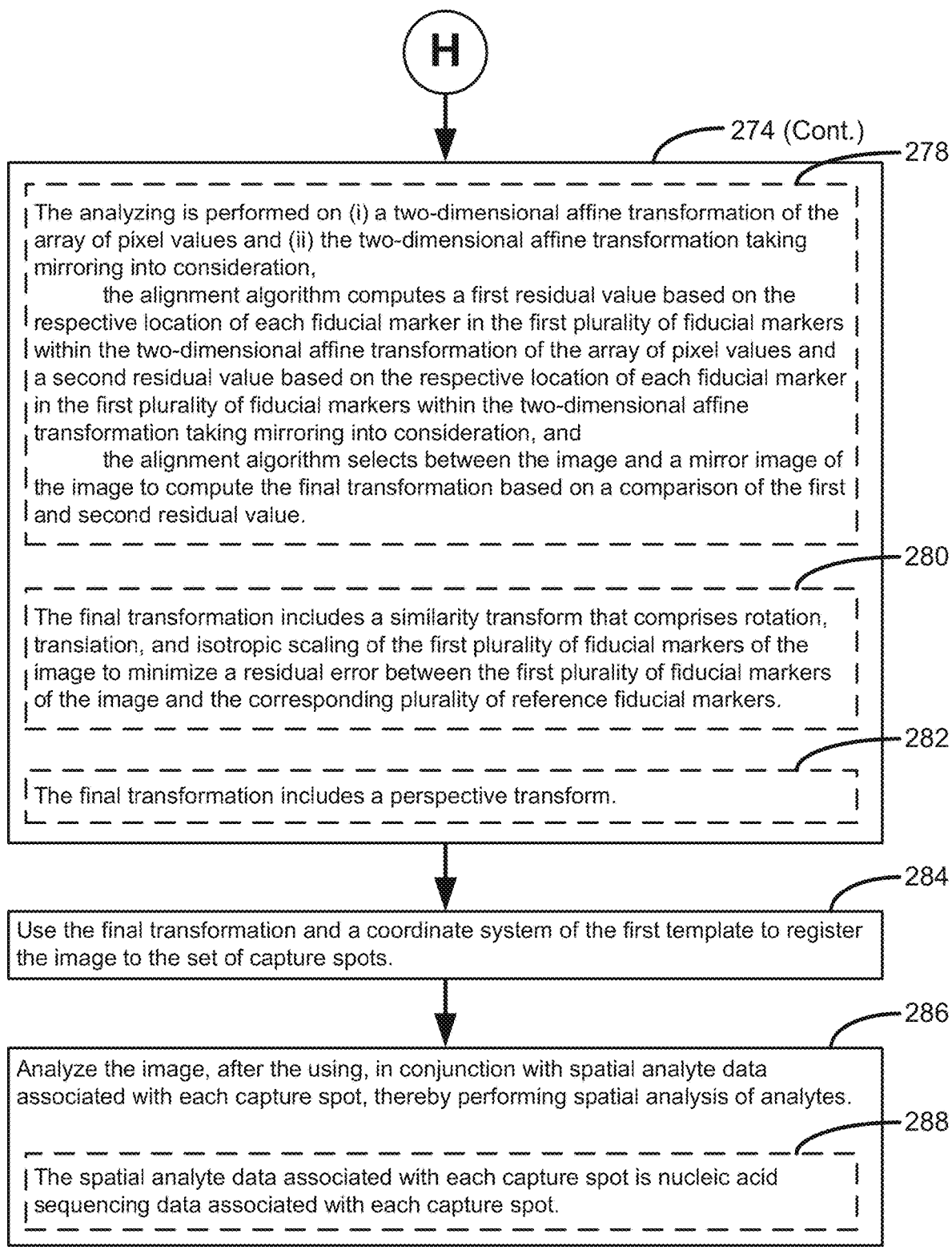

This disclosure describes apparatus, systems, methods, and compositions for spatial analysis of samples. This section in particular describes certain general terminology, analytes, sample types, and preparative steps that are referred to in later sections of the disclosure.

Spatial analysis of analytes can be performed by capturing analytes, analyte capture agents and/or analyte binding domains and mapping them to known locations (e.g., via barcoded capture probes attached to a substrate) using a sample image indicating the tissues or regions of interest that correspond to the known locations. For example, in some implementations of spatial analysis, a sample is prepared (e.g., fresh-frozen tissue is sectioned, placed onto a slide, fixed, and/or stained for imaging). The imaging of the sample provides the sample image to be used for spatial analysis. Analyte detection is then performed using, e.g., analyte or analyte ligand capture via barcoded capture probes, library construction, and sequencing. The resulting barcoded analyte data and the sample image can be combined during data visualization for spatial analysis.

One difficulty with such analysis is ensuring that a sample or an image of a sample (e.g., a tissue section or an image of a tissue section) is properly aligned with the barcoded capture probes (e.g., using fiducial alignment). Technical limitations in the field include imperfections in sample quality that can be introduced during conventional wet-lab methods for tissue sample preparation and sectioning. These issues arise either due to the nature of the tissue sample itself (including, inter alia, interstitial regions, vacuoles and/or general granularity that is often difficult to interpret after imaging) or from improper handling or sample degradation resulting in gaps or holes in the sample (e.g., tearing samples or obtaining only a partial sample such as from a biopsy). Additionally, wet-lab methods for imaging result in further imperfections, including but not limited to air bubbles, debris, crystalline stain particles deposited on the substrate or tissue, inconsistent or poor-contrast staining, and/or microscopy limitations that produce image blur, over- or under-exposure, and/or poor resolution. See, Uchida, 2013, "Image processing and recognition for biological images," Develop. Growth Differ. 55, 523-549, doi:10.1111/dgd.12054, which is hereby incorporated herein by reference in its entirety. Such imperfections make the alignment of sample image to analyte data more difficult.

Given the above limitations, there is a need in the art for systems and methods that provide improved alignment. Advantageously, the systems and methods of the present disclosure facilitate reproducible detection and alignment of samples in images to analyte data, without the need for extensive training and labor costs. Moreover, the presently disclosed systems and methods improve the accuracy of alignment by removing issues of uncertainty and subjectivity that arise from human manual alignment. Such systems and methods provide a cost-effective, user-friendly tool for a practitioner to reliably perform spatial reconstruction of analytes in sample images without the need for additional user input during the spatial mapping step beyond providing the image.

Accordingly, the present disclosure provides systems and methods for improved spatial analysis of analytes. In an example embodiment, a data structure is obtained, comprising an image of a sample on a substrate, where the substrate includes a plurality of intersecting border regions (e.g., four borders surrounding a capture spot array). The substrate includes a set of capture spots (e.g., at least 1000 capture spots in a capture spot array), and the image includes a plurality of pixel values corresponding to an array of pixels in the image. The substrate also includes a plurality of fiducial markers encoding different N-digit codes. In some embodiments, each fiducial marker in the plurality of fiducial markers has a different pattern in a plurality of patterns, such that each fiducial marker on the substrate is unique and encodes a different, unique N-digit code.

In some embodiments, each respective pattern is a different concentric circular pattern. In an illustrative example, a respective pattern comprises three rings and two inter-ring spacings, where each ring is characterized by a respective linewidth and each inter-ring spacing is characterized by a respective inter-ring spacing width. A respective linewidth and/or a respective inter-ring spacing width can be selected from thin (e.g., 0), medium (e.g., 1), and thick (e.g., 2) widths. Thus, in the illustrative example, the N-digit code is a five bit ternary code indicating the sequence of selected widths for each of the three rings and the two inter-ring spacings (e.g., 0-1-1-0-2 or 2-2-2-2-2). While the foregoing example uses three rings and two inter-ring spacings, a respective fiducial marker can include any number N of rings (where N is a positive integer of 2 or greater) and corresponding inter-ring spacings, each of which can be characterized by any number of possible corresponding widths. Each of the rings and inter-ring spacings can have the same or a different set of possible corresponding widths, the selection of which can be encoded in the N-digit code.

Returning to the method, the plurality of pixel values is analyzed to identify a respective location of each fiducial marker within the image. Briefly, an edge detection algorithm is used to find edges in the image, and edge-groups are constructed based on the normal direction of each identified edge (e.g., a perpendicular line passing through a given number of edges). The number of edges used to construct each edge-group is based on the number of expected edges in a respective fiducial marker; for instance, a fiducial marker comprising three concentric rings defines an edge-group of length six. Candidate edge-groups can be further filtered by, e.g., setting a minimum or maximum distance between edges in order to be grouped into a respective edge-group.

The center of each edge-group is determined by averaging over the constituent edges within the edge-group. A circle Hough transform (CHT) is performed using the identified edge-group centers, assisted by the normal directions corresponding to the identified centers. In brief, for each respective edge-group center, a CHT simulates candidate circles using the edge-group center to define candidate circle perimeters. Fiducial centers are identified at points (e.g., pixels) within the image where the number of intersecting candidate circle perimeters generated for all of the edge-group centers exceeds a threshold value (e.g., reach a local maximum).

Edge-groups are assigned to fiducial centers based on distance; for instance, in some embodiments, each edge-group is grouped to the closest fiducial center. The edges of each edge-group are then ordered based on the distance between each edge and its corresponding fiducial center. Thus, for a fiducial marker comprising three concentric rings, the edge closest to the fiducial center in an edge-group of length six would correspond to the inner edge of the innermost circle (e.g., order 1), and the edge farthest from the fiducial center would correspond to the outer edge of the outermost circle (e.g., order 6).

In some implementations, the method includes refining the fiducial center by fitting the center against a subset of edges, in a plurality of subsets of edges, across the plurality of assigned edge-groups, where each edge in each subset of edges has a common order. For example, the innermost edges of all of the assigned edge-groups would be grouped into a first subset (e.g., order 1) and the second edges of all of the assigned edge-groups would be grouped into a second subset (e.g., order 2). For a fiducial marker comprising three concentric rings, the fitting thus generates six fitted fiducial centers corresponding to each ordered subset of edges. The plurality of fitted fiducial centers are averaged, thereby generating a refined fiducial center. For each ordered subset of edges, the distance of each respective edge from the refined fiducial center is determined and averaged, thereby generating a respective radius for each perimeter (e.g., inner and outer perimeter) of each concentric circle in the fiducial marker.

As described above, the generated radii can be used to determine the respective linewidths and inter-ring spacing widths for each ring and inter-ring spacing of each respective fiducial marker identified using the foregoing procedure. When encoded into an N-digit code (e.g., a five bit ternary code), the identity of the fiducial marker can be elucidated (e.g., based on the unique assignment of N-digit codes).

The location of the fiducial marker on the substrate is determined using a template that indicates the position of a plurality of reference fiducial markers relative to the substrate and the set of capture spots on the substrate. Specifically, in some such embodiments, an alignment algorithm is used to align each respective fiducial marker within the image with a corresponding reference fiducial marker in the template to obtain a final transformation between the plurality of fiducial markers of the image and the plurality of reference fiducial markers of the template. The final transformation and a coordinate system of the template are used to register the image to the set of capture spots. The image can then be analyzed in conjunction with spatial analyte data associated with each capture spot, thereby performing spatial analysis of analytes.

As described above, and as illustrated by the exemplary embodiment, the systems and methods provided by the present disclosure facilitate reproducible detection and alignment of samples in images to analyte data by automating (i) the detection of fiducial markers and (ii) the subsequent use of the identified fiducial markers to align a sample image to a set of capture spots associated with analyte data. Advantageously, the systems and methods also allow for orientation, alignment, and registration of a sample image using fiducial markers even in cases where some of the fiducial markers are obscured. For instance, a sample can be placed onto a substrate such that a portion of the plurality of fiducial markers is covered by the sample. In some cases, the sample covers a majority of the fiducial markers in the plurality of fiducial markers or one or more entire border regions. Orientation and alignment of the sample image to the set of capture spots on the substrate can be prone to errors in such instances, particularly when the plurality of fiducial markers on the substrate comprise repetitive patterns for which the respective positions of individual fiducial markers are difficult to distinguish from their flipped, rotated, or translocated counterparts.

Accordingly, the present disclosure allows for the accurate alignment of sample images to analyte data even in instances where only three fiducial markers are visible on the substrate. In such cases, the fiducial markers are present on at least two different border regions. Advantageously, the alignment is facilitated by the different N-digit code for each respective fiducial marker in the plurality of fiducial markers, which allows each respective fiducial marker to be individually localized on the substrate without the uncertainty resulting from repetitive patterns of identical fiducial markers.

The systems and methods of the present disclosure provide benefits to applications in which large numbers of samples and/or large numbers of images are processed. For example, clinical or diagnostic studies can involve spatial analysis of analytes using multiple sections of one or more tissues obtained from one or more subjects. In some such instances, samples on a substrate can be flipped, rotated, translocated, or tilted during processing, such as when mounting a substrate onto an imaging platform. Additionally, sample images can be imaged from above or below the platform, depending on the type of imaging system used, which can result in ostensibly flipped images. These variations in sample acquisition result in further uncertainties that lead to alignment error, in addition to the difficulties introduced by the potential obfuscation of one or more fiducial markers. These issues become particularly apparent when processing large numbers of samples, such as de-identified clinical samples, where individual monitoring and manual adjustment may not be feasible.

In another example, a sample on a substrate can be a single cell suspension that contains few or no histological features that allow for visual orientation of the image to the analyte data. Thus, accurate alignment of the fiducial markers to analyte data cannot be manually performed. Furthermore, sample images can be flipped, cropped, or otherwise manipulated after acquisition, either purposely or inadvertently, prior to performing spatial analysis of analytes. The present disclosure advantageously provides for the orientation and alignment of sample images that take into account at least the above-mentioned situations and thus facilitates improved, more accurate analysis of spatial analyte data.

Definitions

Specific terminology is used throughout this disclosure to explain various aspects of the apparatus, systems, methods, and compositions that are described. This sub-section includes explanations of certain terms that appear in later sections of the disclosure. To the extent that the descriptions in this section are in apparent conflict with usage in other sections of this disclosure, the definitions in this section will control.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated integers, steps, operations, elements, and/or components, but do not preclude the presence or addition of one or more other integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting (the stated condition or event)" or "in response to detecting (the stated condition or event)," depending on the context.

The term "each," when used in reference to a collection of items, is intended to identify an individual item in the collection but does not necessarily refer to every item in the collection, unless expressly stated otherwise, or unless the context of the usage clearly indicates otherwise.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

Analytes

As used herein, the term "analyte" refers to any biological substance, structure, moiety, or component to be analyzed.

In some embodiments, the apparatus, systems, methods, and compositions described in this disclosure can be used to detect and analyze a wide variety of different analytes.

Analytes can generally be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte is an organelle (e.g., nuclei or mitochondria). In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a connected probe (e.g., a ligation product) or an analyte capture agent (e.g., an oligonucleotide-conjugated antibody), such as those described herein. In some embodiments, analytes can include one or more intermediate agents, e.g., connected probes or analyte capture agents that bind to nucleic acid, protein, or peptide analytes in a sample.

Cell surface elements corresponding to analytes can include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

Analytes can be derived from a specific type of cell and/or a specific sub-cellular region. For example, analytes can be derived from cytosol, from cell nuclei, from mitochondria, from microsomes, and more generally, from any other compartment, organelle, or portion of a cell. Permeabilizing agents that specifically target certain cell compartments and organelles can be used to selectively release analytes from cells for analysis. Examples of nucleic acid analytes include DNA analytes such as genomic DNA, methylated DNA, specific methylated DNA sequences, fragmented DNA, mitochondrial DNA, in situ synthesized PCR products, and RNA/DNA hybrids.

Examples of nucleic acid analytes also include RNA analytes such as various types of coding and non-coding RNA. Examples of the different types of RNA analytes include messenger RNA (mRNA), ribosomal RNA (rRNA), transfer RNA (tRNA), microRNA (miRNA), and viral RNA. The RNA can be a transcript (e.g., present in a tissue section). The RNA can be small (e.g., less than 200 nucleic acid bases in length) or large (e.g., RNA greater than 200 nucleic acid bases in length). Small RNAs mainly include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

Additional examples of analytes include mRNA and cell surface elements (e.g., using the labelling agents described herein), mRNA and intracellular proteins (e.g., transcription factors), mRNA and cell methylation status, mRNA and accessible chromatin (e.g., ATAC-seq, DNase-seq, and/or MNase-seq), mRNA and metabolites (e.g., using the labelling agents described herein), a barcoded labelling agent (e.g., the oligonucleotide tagged antibodies described herein) and a V(D)J sequence of an immune cell receptor (e.g., a T-cell or B-cell receptor), mRNA and a perturbation agent (e.g., a CRISPR crRNA/sgRNA, TALEN, zinc finger nuclease, and/or antisense oligonucleotide as described herein). In some embodiments, a perturbation agent is a small molecule, an antibody, a drug, an aptamer, a miRNA, a physical environmental (e.g., temperature change), or any other known perturbation agents.

In certain embodiments, an analyte is extracted from a live cell deposited on the capture spot array. Processing conditions can be adjusted to ensure that a biological sample remains live during analysis, and analytes are extracted from (or released from) live cells of the sample. Live cell-derived analytes can be obtained only once from the sample or can be obtained at intervals from a sample that continues to remain in viable condition (e.g., permeabilization conditions that do not lyse the cell).

In general, the systems, apparatus, methods, and compositions can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000 or more analytes present in a region of the sample or within an individual capture spot of the substrate.

In some embodiments, multiplexed assays are performed to analyze two or more different analytes. In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) a capture handle sequence. As used herein, the term "analyte binding moiety barcode" refers to a barcode that is associated with or otherwise identifies the analyte binding moiety. As used herein, the term "analyte capture sequence" or "capture handle sequence" refers to a region or moiety configured to hybridize to, bind to, couple to, or otherwise interact with a capture domain of a capture probe. In some embodiments, a capture handle sequence is complementary to a capture domain of a capture probe. In some cases, an analyte binding moiety barcode (or portion thereof) may be removable (e.g., cleaved) from the analyte capture agent.

In some embodiments, detection of one or more analytes (e.g., protein analytes) can be performed using one or more intermediate agents. In some embodiments, the one or more intermediate agents include one or more probes. For example, in some embodiments, a respective analyte is detected indirectly by hybridizing one or more probes to the respective analyte and subsequently detecting the one or more probes after hybridization. In some embodiments, the one or more intermediate agents is a plurality of probes, and detection of analytes is performed by detecting a ligation product obtained from the plurality of probes. In some embodiments, the detection of analytes is performed using RNA-templated ligation. For instance, in some embodiments, RNA-templated ligation comprises hybridization of a set of probes to a target analyte. Each probe in the set of probes hybridizes to a sequence in the analyte that is specific to the analyte, and, upon hybridization, the set of probes is ligated to form a ligation product. In some embodiments, all or a portion of the ligation product is complementary to a capture domain of a capture probe.

In some instances, the one or more intermediate agents for a respective analyte is a pair of probes that is specific to the respective analyte. In some instances, the one or more intermediate agents for a respective analyte is a set of probes that is specific to the respective analyte. In some embodiments, each respective probe in a respective set of probes is an oligonucleotide probe.

In some embodiments, probes can be designed so that one of the probes of a pair is a probe that hybridizes to a specific sequence. Then, the other probe can be designed to detect a mutation of interest. Accordingly, in some instances, multiple second probes can be designed and can vary so that each probe binds to a specific sequence. For example, one second probe can be designed to hybridize to a wild-type sequence, and another second probe can be designed to detect a mutated sequence. Thus, in some instances, a set of probes can include one first probe and two second probes (or vice versa).

In some instances, probes can be designed so that they cover conserved regions of an analyte. Thus, in some instances, a probe (or probe pair) can hybridize to similar analytes in a biological sample (e.g., to detect conserved or similar analytes) or in different biological samples (e.g., across different species).

In some embodiments, the one or more intermediate agents comprises a plurality of probe sets that covers all or nearly all of a genome (e.g., human genome). In instances where the plurality of probe sets are designed to cover an entire genome (e.g., the human genome), the methods disclosed herein can detect analytes in an unbiased manner. In some instances, one probe pair (e.g., oligonucleotide pair) is designed to cover one analyte (e.g., transcript). In some instances, more than one probe pair (e.g., a probe pair comprising a first probe and a second probe) is designed to cover one analyte (e.g., tiling a transcript). For example, at least two, three, four, five, six, seven, eight, nine, ten, or more probe sets can be used to hybridize to a single analyte. Factors to consider when designing probes is presence of variants (e.g., SNPs, mutations) or multiple isoforms expressed by a single gene. In some instances, the probe pair does not hybridize to the entire analyte (e.g., a transcript), but instead the probe pair hybridizes to a portion of the entire analyte (e.g., transcript).

In some instances, the plurality of sets of probes comprises about 5000, 10,000, 15,000, 20,000, or more probe pairs (e.g., a probe pair comprising a first probe and a second probe). In some instances, the plurality of sets of probes comprises about 20,000 probe pairs.

In some instances, analyte capture is performed using targeted RNA capture. Targeted RNA capture allows for examination of a subset of RNA analytes from the entire transcriptome. In some embodiments, the subset of analytes includes an individual target RNA. In some embodiments, the subset of analytes includes two or more targeted RNAs. In some embodiments, the subset of analytes includes one or more mRNAs transcribed by one or more targeted genes. In some embodiments, the subset of analytes includes one or more mRNA splice variants of one or more targeted genes. In some embodiments, the subset of analytes includes non-polyadenylated RNAs in a biological sample. In some embodiments, the subset of analytes includes detection of mRNAs having one or more single nucleotide polymorphisms (SNPs) in a biological sample.

In some embodiments, the subset of analytes includes mRNAs that mediate expression of a set of genes of interest. In some embodiments, the subset of analytes includes mRNAs that share identical or substantially similar sequences, which mRNAs are translated into polypeptides having similar functional groups or protein domains. In some embodiments, the subset of analytes includes mRNAs that do not share identical or substantially similar sequences, which mRNAs are translated into proteins that do not share similar functional groups or protein domains. In some embodiments, the subset of analytes includes mRNAs that are translated into proteins that function in the same or similar biological pathways. In some embodiments, the biological pathways are associated with a pathologic disease. For example, targeted RNA capture can detect genes that are overexpressed or under-expressed in cancer.

In some embodiments, the subset of analytes includes 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, about 55, about 60, about 65, about 70, about 75, about 80, about 85, about 90, about 95, about 100, about 110, about 120, about 130, about 140, about 150, about 160, about 170, about 180, about 190, about 200, about 225, about 250, about 275, about 300, about 325, about 350, about 375, about 400, about 425, about 450, about 475, about 500, about 600, about 700, about 800, about 900, or about 1000 analytes.

In some instances, the methods disclosed herein can detect the abundance and location of at least 5,000, 10,000, 15,000, 20,000, or more different analytes.

In some embodiments, the subset of analytes detected by targeted RNA capture methods provided herein includes a large proportion of the transcriptome of one or more cells. For example, the subset of analytes detected by targeted RNA capture methods provided herein can include at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more of the mRNAs present in the transcriptome of one or more cells.

In some instances, the probes are DNA probes. In some instances, the probes are diribo-containing probes.

Additional examples of analytes suitable for use in the present disclosure are described in U.S. Pat. No. 11,501,440, entitled "SYSTEMS AND METHODS FOR SPATIAL ANALYSIS OF ANALYTES USING FIDUCIAL ALIGNMENT," U.S. Patent Application Publication No. US2021-0150707, entitled "SYSTEMS AND METHODS FOR TISSUE CLASSIFICATION," published May 20, 2021; U.S. Pat. No. 11,514,575, entitled "Systems and Methods for Identifying Morphological Patterns in Tissue Samples," published Apr. 1, 2021; and U.S. Patent Application Publication No. US2021-0155982 A1, entitled "Pipeline for Spatial Analysis of Analytes," published May 27, 2021, each of which is hereby incorporated herein by reference in its entirety.

Examples of RNA-templated ligation suitable for use in the present disclosure are described in U.S. Pat. Nos. 11,332,790; 11,505,828; and 11,560,593; and PCT Publication No. WO2021/133849; each of which is hereby incorporated herein by reference in its entirety.

Barcodes

As used herein, the term "barcode" refers to a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes.

Barcodes can have a variety of different formats. For example, barcodes can include polynucleotide barcodes, random nucleic acid and/or amino acid sequences, and synthetic nucleic acid and/or amino acid sequences. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI").

Barcodes can spatially-resolve molecular components found in biological samples, for example, a barcode can be or can include a "spatial barcode". In some embodiments, a barcode includes both a UMI and a spatial barcode. In some embodiments the UMI and barcode are separate entities. In some embodiments, a barcode includes two or more sub-barcodes that together function as a single barcode. For example, a polynucleotide barcode can include two or more polynucleotide sequences (e.g., sub-barcodes) that are separated by one or more non-barcode sequences.

Barcodes suitable for use in the present disclosure are further described in U.S. Pat. No. 11,501,440, entitled "SYSTEMS AND METHODS FOR SPATIAL ANALYSIS OF ANALYTES USING FIDUCIAL ALIGNMENT," U.S. Patent Application Publication No. US2021-0150707, entitled "SYSTEMS AND METHODS FOR TISSUE CLASSIFICATION," published May 20, 2021; U.S. Pat. No. 11,514,575, entitled "Systems and Methods for Identifying Morphological Patterns in Tissue Samples," published Apr. 1, 2021; and U.S. Patent Application Publication No. US2021-0155982 A1, entitled "Pipeline for Spatial Analysis of Analytes," published May 27, 2021, each of which is hereby incorporated herein by reference in its entirety.

Biological Samples

As used herein, the term "sample" or "biological sample" refers to any material obtained from a subject for analysis using any of a variety of techniques including, but not limited to, biopsy, surgery, and laser capture microscopy (LCM), and generally includes cells and/or other biological material from the subject. In addition to the subjects described above, a biological sample can also be obtained from non-mammalian organisms (e.g., plants, insects, arachnids, nematodes, fungi, amphibians, and fish. A biological sample can be obtained from a prokaryote such as a bacterium, e.g., *Escherichia coli*, Staphylococci or *Mycoplasma pneumoniae*; archaea; a virus such as Hepatitis C virus or human immunodeficiency virus; or a viroid. A biological sample can also be obtained from a eukaryote, such as a patient derived organoid (PDO) or patient derived xenograft (PDX). The biological sample can include organoids, a miniaturized and simplified version of an organ produced in vitro in three dimensions that shows realistic microanatomy. Organoids can be generated from one or more cells from a tissue, embryonic stem cells, and/or induced pluripotent stem cells, which can self-organize in three-dimensional culture owing to their self-renewal and differentiation capacities. In some embodiments, an organoid is a cerebral organoid, an intestinal organoid, a stomach organoid, a lingual organoid, a thyroid organoid, a thymic organoid, a testicular organoid, a hepatic organoid, a pancreatic organoid, an epithelial organoid, a lung organoid, a kidney organoid, a gastruloid, a cardiac organoid, or a retinal organoid. Subjects from which biological samples can be obtained can be healthy or asymptomatic individuals, individuals that have or are suspected of having a disease (e.g., cancer) or a pre-disposition to a disease, and/or individuals that are in need of therapy or suspected of needing therapy.

The biological sample can include any number of macromolecules, for example, cellular macromolecules and organelles (e.g., mitochondria and nuclei). The biological sample can include nucleic acids and/or proteins. The biological sample can include carbohydrates or lipids. The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, bone sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions and/or disaggregated cells.

Cell-free biological samples can include extracellular polynucleotides. Extracellular polynucleotides can be isolated from a bodily sample, e.g., blood, plasma, serum, urine, saliva, mucosal excretions, sputum, stool, and tears.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic characteristics. Examples of diseases include inflammatory disorders, metabolic disorders, nervous system disorders, and cancer. Cancer cells can be derived from solid tumors, hematological malignancies, cell lines, or obtained as circulating tumor cells.

Biological samples can also include fetal cells. For example, a procedure such as amniocentesis can be performed to obtain a fetal cell sample from maternal circulation. Sequencing of fetal cells can be used to identify any of a number of genetic disorders, including, e.g., aneuploidy such as Down's syndrome, Edwards syndrome, and Patau syndrome. Further, cell surface elements of fetal cells can be used to identify any of a number of disorders or diseases.

Biological samples can also include immune cells. Sequence analysis of the immune repertoire of such cells, including genomic, proteomic, and cell surface elements, can provide a wealth of information to facilitate an understanding the status and function of the immune system. Examples of immune cells in a biological sample include, but are not limited to, B cells, T cells (e.g., cytotoxic T cells, natural killer T cells, regulatory T cells, and T helper cells), natural killer cells, cytokine induced killer (CIK) cells, myeloid cells, such as granulocytes (basophil granulocytes, eosinophil granulocytes, neutrophil granulocytes/hyper-segmented neutrophils), monocytes/macrophages, mast cells, thrombocytes/megakaryocytes, and dendritic cells.

As discussed above, a biological sample can include a single analyte of interest, or more than one analyte of interest.

A variety of steps can be performed to prepare a biological sample for analysis. Except where indicated otherwise, the preparative steps for biological samples can generally be combined in any manner to appropriately prepare a particular sample for analysis.

For instance, in some embodiments, the biological sample is a tissue section. In some embodiments, the biological sample is prepared using tissue sectioning. A biological sample can be harvested from a subject (e.g., via surgical biopsy, whole subject sectioning, grown in vitro (e.g., patient derived tumor(s) or patient derived organoid(s)) on a growth substrate or culture dish as a population of cells, or prepared for analysis as a tissue slice or tissue section). Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material. The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 micrometers thick.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 11, 12, 13, 14, 15, 20, 30, 40, or 50 micrometers. Thicker sections can also be used if desired or convenient, e.g., at least 70, 80, 90, or 100 micrometers or more. Typically, the thickness of a tissue section is between 1-100 micrometers, 1-50 micrometers, 1-30 micrometers, 1-25 micrometers, 1-20 micrometers, 1-15 micrometers, 1-10 micrometers, 2-8 micrometers, 3-7 micrometers, or 4-6 micrometers, but as mentioned above, sections with thicknesses larger or smaller than these ranges can also be analyzed.

In some embodiments, a tissue section is a similar size and shape to a substrate (e.g., the first substrate and/or the second substrate). In some embodiments, a tissue section is a different size and shape from a substrate. In some embodiments, a tissue section is on all or a portion of the substrate. In some embodiments, several biological samples from a subject are concurrently analyzed. For instance, in some embodiments several different sections of a tissue are concurrently analyzed. In some embodiments, 1, 2, 3, 4, 5, 6, 7, 8, 9, 10, 11, 12, 13, 14, 15, 16, 17, 18, 19, or 20 different biological samples from a subject are concurrently analyzed. For example, in some embodiments, 1, 2, 3, 4, 5, 6, 7, 8, 9, 10, 11, 12, 13, 14, 15, 16, 17, 18, 19, or 20 different tissue sections from a single biological sample from a single subject are concurrently analyzed. In some embodiments, one or more images are acquired of each such tissue section.

In some embodiments, a tissue section on a substrate is a single uniform tissue section. In some embodiments, multiple tissue sections are placed proximal but not overlapping on a substrate. In some such embodiments, a single capture area can contain multiple tissue sections, where each tissue section is obtained from either the same biological sample and/or subject or from different biological samples and/or subjects. In some embodiments, a tissue section is a single tissue section that comprises one or more regions where no cells are present (e.g., holes, tears, or gaps in the tissue). Thus, in some embodiments, such as the above, an image of a tissue section on a substrate can contain regions where tissue is present and regions where tissue is not present.

Additional examples of tissue samples are catalogued, for example, in 10X, 2019, "Visium Spatial Gene Expression Solution," in in U.S. Pat. No. 11,501,440, entitled "SYSTEMS AND METHODS FOR SPATIAL ANALYSIS OF ANALYTES USING FIDUCIAL ALIGNMENT," U.S. Patent Application Publication No. US2021-0150707, entitled "SYSTEMS AND METHODS FOR TISSUE CLASSIFICATION," published May 20, 2021; U.S. Pat. No. 11,514,575, entitled "Systems and Methods for Identifying Morphological Patterns in Tissue Samples," published Apr. 1, 2021; and U.S. Patent Application Publication No. US2021-0155982 A1, entitled "Pipeline for Spatial Analysis of Analytes," published May 27, 2021, each of which is hereby incorporated herein by reference in its entirety.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analyzed successively to obtain three-dimensional information about the biological sample.

In some embodiments, a biological sample is prepared using one or more steps including, but not limited to, freezing, fixation, embedding, formalin fixation and paraffin embedding, hydrogel embedding, biological sample transfer, isometric expansion, cell disaggregation, cell suspension, cell adhesion, permeabilization, lysis, protease digestion, selective permeabilization, selective lysis, selective enrichment, enzyme treatment, library preparation, and/or sequencing pre-processing. Methods for biological sample preparation that are contemplated in the present disclosure are described in further detail in U.S. Pat. No. 11,501,440, entitled "SYSTEMS AND METHODS FOR SPATIAL ANALYSIS OF ANALYTES USING FIDUCIAL ALIGNMENT," U.S. Patent Application Publication No. US2021-0150707, entitled "SYSTEMS AND METHODS FOR TISSUE CLASSIFICATION," published May 20, 2021; U.S. Pat. No. 11,514,575, entitled "Systems and Methods for Identifying Morphological Patterns in Tissue Samples," published Apr. 1, 2021; and U.S. Patent Application Publication No. US2021-0155982 A1, entitled "Pipeline for Spatial Analysis of Analytes," published May 27, 2021, each of which is hereby incorporated herein by reference in its entirety.

In some embodiments, a biological sample is prepared by staining. To facilitate visualization, biological samples can be stained using a wide variety of stains and staining techniques. In some embodiments, for example, a sample can be stained using any number of biological stains, including but not limited to, acridine orange, Bismarck brown, carmine, Coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, safranin, or a combination thereof.

The sample can be stained using known staining techniques, including Can-Grunwald, Giemsa, hematoxylin and eosin (H&E), Jenner's, Leishman, Masson's trichrome, Papanicolaou, Romanowsky, silver, Sudan, Wright's, and/or Periodic Acid Schiff (PAS) staining techniques. PAS staining is typically performed after formalin or acetone fixation.

In some embodiments, the sample is stained using a detectable label (e.g., radioisotopes, fluorophores, chemiluminescent compounds, bioluminescent compounds, and dyes). In some embodiments, a biological sample is stained using only one type of stain or one technique. In some embodiments, staining includes biological staining techniques such as H&E staining. In some embodiments, staining includes identifying analytes using fluorescently-labeled antibodies. In some embodiments, a biological sample is stained using two or more different types of stains, or two or more different staining techniques. For example, a biological sample can be prepared by staining and imaging using one technique (e.g., H&E staining and bright-field imaging), followed by staining and imaging using another technique (e.g., IHC/IF staining and fluorescence microscopy) for the same biological sample.

In some embodiments, biological samples can be destained. Methods of destaining or discoloring a biological sample are known in the art, and generally depend on the nature of the stain(s) applied to the sample. For example, H&E staining can be destained by washing the sample in HCl, or any other low pH acid (e.g., selenic acid, sulfuric acid, hydroiodic acid, benzoic acid, carbonic acid, malic acid, phosphoric acid, oxalic acid, succinic acid, salicylic acid, tartaric acid, sulfurous acid, trichloroacetic acid, hydrobromic acid, hydrochloric acid, nitric acid, orthophosphoric acid, arsenic acid, selenous acid, chromic acid, citric acid, hydrofluoric acid, nitrous acid, isocyanic acid, formic acid, hydrogen selenide, molybdic acid, lactic acid, acetic acid, carbonic acid, hydrogen sulfide, or combinations thereof). In some embodiments, destaining can include 1, 2, 3, 4, 5, or more washes in a low pH acid (e.g., HCl). In some embodiments, destaining can include adding HCl to a downstream solution (e.g., permeabilization solution). In some embodiments, destaining can include dissolving an enzyme used in the disclosed methods (e.g., pepsin) in a low pH acid (e.g., HCl) solution. In some embodiments, after destaining hematoxylin with a low pH acid, other reagents can be added to the destaining solution to raise the pH for use in other applications. For example, SDS can be added to a low pH acid destaining solution in order to raise the pH as compared to the low pH acid destaining solution alone. As another example, in some embodiments, one or more immunofluorescence stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., 2017, J. Histochem. Cytochem. 65(8): 431-444, Lin et al., 2015, Nat Commun. 6:8390, Pirici et al., 2009, J. Histochem. Cytochem. 57:567-75, and Glass et al., 2009, J. Histochem. Cytochem. 57:899-905, the entire contents of each of which are incorporated herein by reference.

In some embodiments, the biological sample can be attached to a substrate (e.g., a slide and/or a chip). Examples of substrates suitable for this purpose are described in detail elsewhere herein (see, for example, the section entitled "Definitions: Substrates," below). Attachment of the biological sample can be irreversible or reversible, depending upon the nature of the sample and subsequent steps in the analytical method.

In certain embodiments, the sample can be attached to the substrate reversibly by applying a suitable polymer coating to the substrate and contacting the sample to the polymer coating. The sample can then be detached from the substrate using an organic solvent that at least partially dissolves the polymer coating. Hydrogels are examples of polymers that are suitable for this purpose. More generally, in some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

Biological samples contemplated for use in the present disclosure are further described in U.S. Pat. No. 11,501,440, entitled "SYSTEMS AND METHODS FOR SPATIAL ANALYSIS OF ANALYTES USING FIDUCIAL ALIGNMENT," U.S. Patent Application Publication No. US2021-0150707, entitled "SYSTEMS AND METHODS FOR TISSUE CLASSIFICATION," published May 20, 2021; U.S. Pat. No. 11,514,575, entitled "Systems and Methods for Identifying Morphological Patterns in Tissue Samples," published Apr. 1, 2021; and U.S. Patent Application Publication No. US2021-0155982 A1, entitled "Pipeline for Spatial Analysis of Analytes," published May 27, 2021, each of which is hereby incorporated herein by reference in its entirety.

Capture Probes

A "capture probe," also interchangeably referred to herein as a "probe," refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe is a conjugate (e.g., an oligonucleotide-antibody conjugate). In some embodiments, the capture probe includes a barcode (e.g., a spatial barcode and/or a unique molecular identifier (UMI)) and a capture domain.

Figure 6:
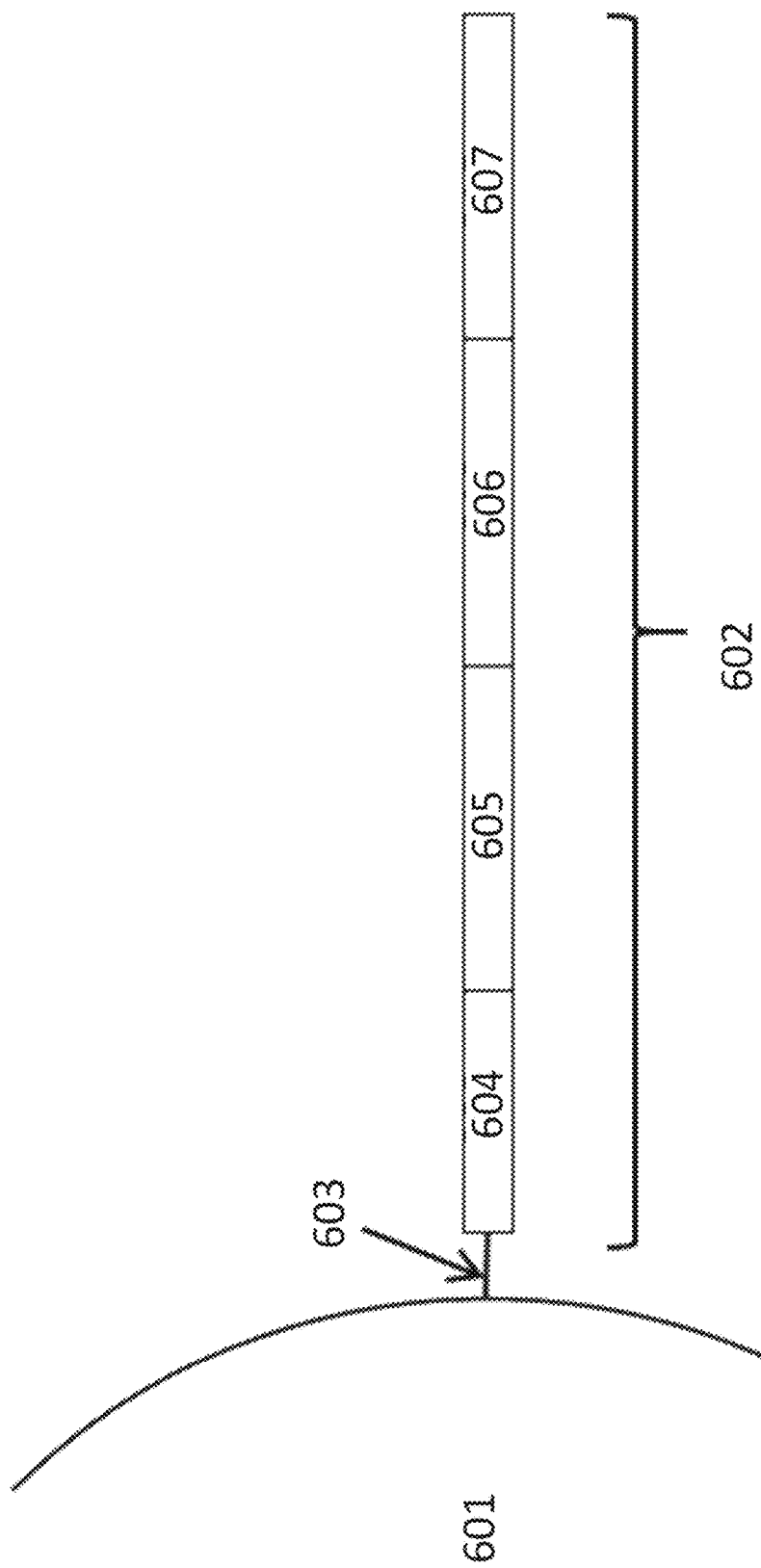
FIG. 6 is a schematic diagram showing an example of a barcoded capture probe, as described herein in accordance with an embodiment of the present disclosure.

FIG. 6 is a schematic diagram showing an example of a capture probe, as described herein. As shown, the capture probe 602 is optionally coupled to a capture spot 601 by a cleavage domain 603, such as a disulfide linker. The capture probe 602 can include functional sequences that are useful for subsequent processing, such as functional sequence 604, which can include a sequencer specific flow cell attachment sequence, e.g., a P5 sequence, as well as functional sequence 606, which can include sequencing primer sequences, e.g., a R1 primer binding site, an R2 primer binding site, etc. In some embodiments, sequence 604 is a P7 sequence and sequence 606 is a R2 primer binding site.

A barcode (e.g., a spatial barcode) 605 can be included within the capture probe for use in barcoding the target analyte. The functional sequences can be selected for compatibility with a variety of different short-read and long-read sequencing systems, e.g., 454 Sequencing, Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the barcode 605, functional sequences 604 (e.g., flow cell attachment sequence) and 606 (e.g., sequencing primer sequences) can be common to all of the probes attached to a given capture spot. The spatial barcode can also include a capture domain 607 to facilitate capture of a target analyte.

Figure 7:
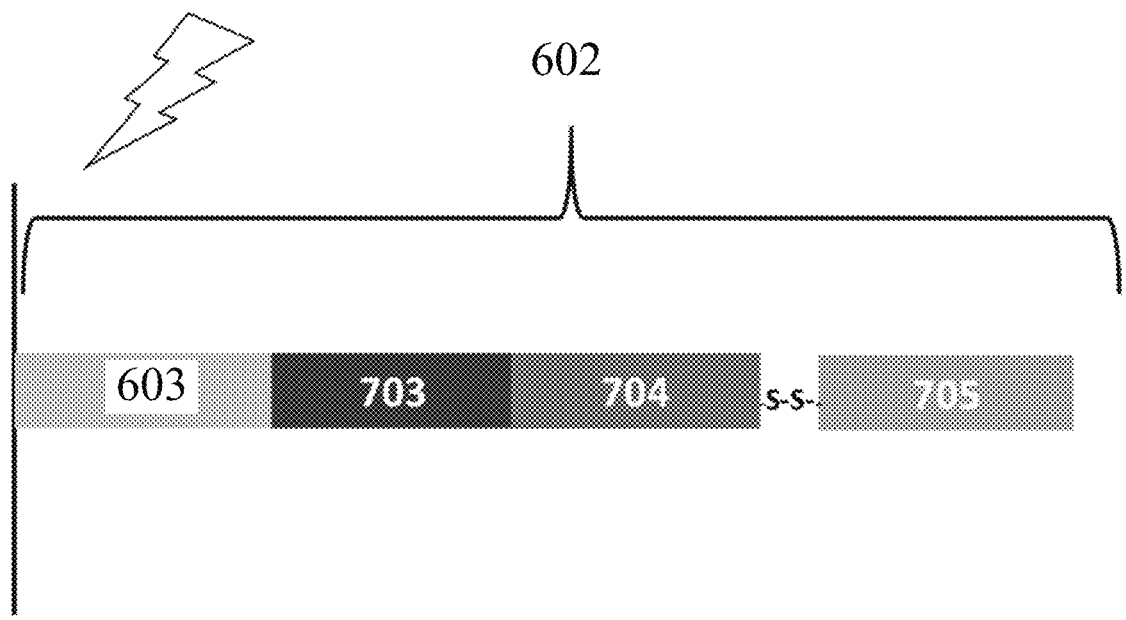
FIG. 7 is a schematic illustrating a cleavable capture probe, in accordance with an embodiment of the present disclosure.

Each capture probe can optionally include at least one cleavage domain 603. The cleavage domain represents the portion of the probe that is used to reversibly attach the probe to a capture spot, such as an array capture spot, as will be described further below. Further, one or more segments or regions of the capture probe can optionally be released from the array capture spot by cleavage of the cleavage domain. FIG. 7 is a schematic illustrating a cleavable capture probe, where the cleaved capture probe can enter into a non-permeabilized cell and bind to target analytes within the sample. The capture probe 602 contains a cleavage domain 603, a cell penetrating peptide 703, a reporter molecule 704, and a disulfide bond (—S—S—). 705 represents all other parts of a capture probe, for example, a spatial barcode and a capture domain.

The capture probe can include one or more (e.g., two or more, three or more, four or more, five or more) unique molecular identifiers (UMIs). A unique molecular identifier is a contiguous nucleic acid segment or two or more non-contiguous nucleic acid segments that function as a label or identifier for a particular analyte, or for a capture probe that binds a particular analyte (e.g., via the capture domain). A UMI can be unique. A UMI can include one or more specific polynucleotides sequences, one or more random nucleic acid and/or amino acid sequences, and/or one or more synthetic nucleic acid and/or amino acid sequences. In some embodiments, the UMI is a nucleic acid sequence that does not substantially hybridize to analyte nucleic acid molecules in a biological sample. In some embodiments, the UMI has less than 80% sequence identity (e.g., less than 70%, 60%, 50%, or less than 40% sequence identity) to the nucleic acid sequences across a substantial portion (e.g., 80% or more) of the nucleic acid molecules in the biological sample. In some embodiments, a UMI is attached to an analyte in a reversible or irreversible manner. In some embodiments, a UMI is added to, for example, a fragment of a DNA or RNA sample before, during, and/or after sequencing of the analyte. In some embodiments, a UMI allows for identification and/or quantification of individual sequencing-reads.

In some embodiments, after analytes from the sample have hybridized or otherwise been associated with capture probes, analyte capture agents, or other barcoded oligonucleotide sequences according to any of the methods described herein in connection with the general spatial cell-based analytical methodology, the barcoded constructs that result from hybridization/association are analyzed via sequencing to identify the analytes.

In some embodiments, where a tissue sample is barcoded directly via hybridization with capture probes or analyte capture agents hybridized, bound, or associated with either cell surfaces, or introduced into cells of the tissue sample, as described above, sequencing can be performed on the tissue sample.

A wide variety of different sequencing methods can be used to analyze barcoded analyte constructs. In general, sequenced polynucleotides can be, for example, nucleic acid molecules such as deoxyribonucleic acid (DNA) or ribonucleic acid (RNA), including variants or derivatives thereof (e.g., single stranded DNA or DNA/RNA hybrids, and nucleic acid molecules with a nucleotide analog).

Sequencing of polynucleotides can be performed by various commercial systems. More generally, sequencing can be performed using nucleic acid amplification, polymerase chain reaction (PCR) (e.g., digital PCR and droplet digital PCR (ddPCR), quantitative PCR, real time PCR, multiplex PCR, PCR-based singleplex methods, emulsion PCR), and/or isothermal amplification.

Other examples of methods for sequencing genetic material include, but are not limited to, DNA hybridization methods (e.g., Southern blotting), restriction enzyme digestion methods, Sanger sequencing methods, next-generation sequencing methods (e.g., single-molecule real-time sequencing, nanopore sequencing, and Polony sequencing), ligation methods, and microarray methods. Additional examples of sequencing methods that can be used include targeted sequencing, single molecule real-time sequencing, exon sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, co-amplification at lower denaturation temperature-PCR (COLD-PCR), sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and any combinations thereof.

Sequence analysis of the nucleic acid molecules (including barcoded nucleic acid molecules or derivatives thereof) can be direct or indirect. Thus, the sequence analysis substrate (which can be viewed as the molecule which is subjected to the sequence analysis step or process) can directly be the barcoded nucleic acid molecule or it can be a molecule which is derived therefrom (e.g., a complement thereof). Thus, for example, in the sequence analysis step of a sequencing reaction, the sequencing template can be the barcoded nucleic acid molecule, or it can be a molecule derived therefrom. For example, a first and/or second strand DNA molecule can be directly subjected to sequence analysis (e.g., sequencing), i.e., can directly take part in the sequence analysis reaction or process (e.g., the sequencing reaction or sequencing process, or be the molecule which is sequenced or otherwise identified). Alternatively, the barcoded nucleic acid molecule can be subjected to a step of second strand synthesis, or amplification, before sequence analysis (e.g., sequencing or identification by another technique). The sequence analysis substrate (e.g., template) can thus be an amplicon or a second strand of a barcoded nucleic acid molecule.

In some embodiments, the sequencing of the nucleic acid molecule sequences a captured analyte capture moiety, such as an intermediate agent. In some embodiments, the sequencing determines a sequence for a captured ligation product derived from a set of probes upon hybridization of the set of probes to a target analyte. In some embodiments, the sequencing determines a sequence for a ligation product obtained from RNA-templated ligation.

Examples of RNA-templated ligation suitable for use in the present disclosure are described in U.S. Pat. Nos. 11,332, 790; 11,505,828; and 11,560,593; and PCT Publication No. WO2021/133849; each of which is hereby incorporated herein by reference in its entirety.

Other aspects of capture probes contemplated for use in the present disclosure are known in the art. For instance, example suitable cleavage domains are described in further detail in PCT publication 202020176788A1, entitled "Profiling of biological analytes with spatially barcoded oligonucleotide arrays," the entire contents of which is incorporated herein by reference. Example suitable functional domains are described in further detail in U.S. Patent Application Publication No. US2021-0062272, entitled "Systems and Methods for Using the Spatial Distribution of Haplotypes to Determine a Biological Condition," published Mar. 4, 2021, as well as PCT publication 202020176788A1, entitled "Profiling of biological analytes with spatially barcoded oligonucleotide arrays," each of which is hereby incorporated herein by reference. Example suitable spatial barcodes and unique molecular identifiers are described in further detail in U.S. Patent Application Publication No. US2021-0062272, entitled "Systems and Methods for Using the Spatial Distribution of Haplotypes to Determine a Biological Condition," published Mar. 4, 2021, and PCT publication 202020176788A1, entitled "Profiling of biological analytes with spatially barcoded oligonucleotide arrays," each of which is hereby incorporated herein by reference.

Capture probes contemplated for use in the present disclosure are further described in U.S. Pat. No. 11,501,440, entitled "SYSTEMS AND METHODS FOR SPATIAL ANALYSIS OF ANALYTES USING FIDUCIAL ALIGNMENT," U.S. Patent Application Publication No. US2021-0150707, entitled "SYSTEMS AND METHODS FOR TISSUE CLASSIFICATION," published May 20, 2021; U.S. Pat. No. 11,514,575, entitled "Systems and Methods for Identifying Morphological Patterns in Tissue Samples," published Apr. 1, 2021; and U.S. Patent Application Publication No. US2021-0155982 A1, entitled "Pipeline for Spatial Analysis of Analytes," published May 27, 2021, each of which is hereby incorporated herein by reference in its entirety.

Capture Spots

As used interchangeably herein, the terms "capture spot," "probe spot," "capture feature," "feature," or "capture probe plurality" refer to an entity that acts as a support or repository for various molecular entities used in sample analysis. Examples of capture spots include, but are not limited to, a bead, a spot of any two- or three-dimensional geometry (e.g., an ink jet spot, a masked spot, a square on a grid), a well, and a hydrogel pad. In some embodiments, a capture spot is an area on a substrate at which capture probes with spatial barcodes are clustered (e.g., placed in groups). Specific non-limiting embodiments of capture spots and substrates are further described below in the present disclosure.

In some embodiments, capture spots are directly or indirectly attached or fixed to a substrate (e.g., of a chip or a slide). In some embodiments, the capture spots are not directly or indirectly attached or fixed to a substrate, but instead, for example, are disposed within an enclosed or partially enclosed three dimensional space (e.g., wells or divots). In some embodiments, some or all capture spots in an array include a capture probe.

In some embodiments, a capture spot includes different types of capture probes attached to the capture spot. For example, the capture spot can include a first type of capture probe with a capture domain designed to bind to one type of analyte, and a second type of capture probe with a capture domain designed to bind to a second type of analyte. In general, capture spots can include one or more (e.g., two or more, three or more, four or more, five or more, six or more, eight or more, ten or more, 12 or more, 15 or more, 20 or more, 30 or more, 50 or more) different types of capture probes attached to a single capture spot.

Figure 8:
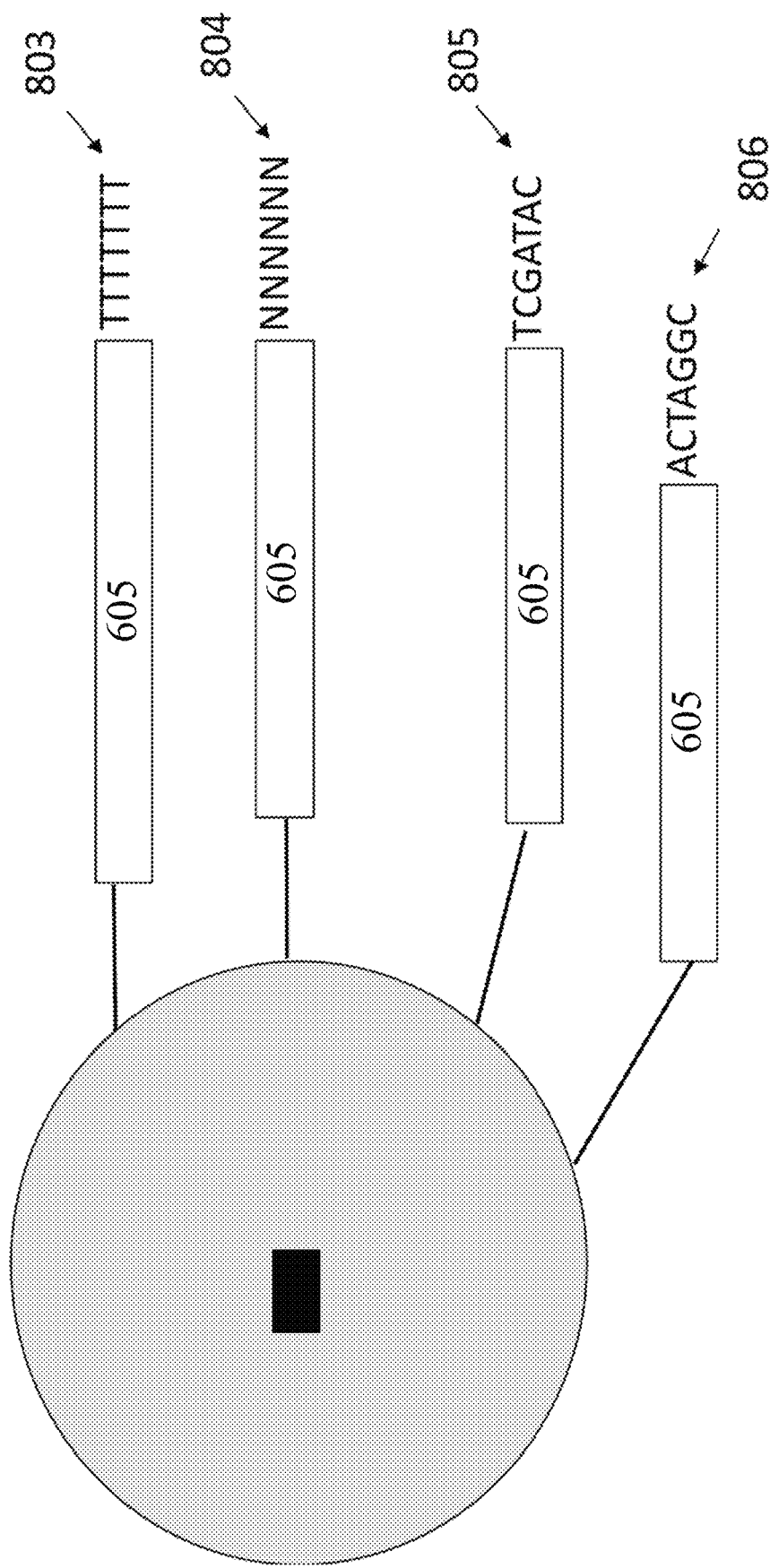
FIG. 8 is a schematic diagram of an exemplary multiplexed spatially-labelled capture spot, in accordance with an embodiment of the present disclosure.

FIG. 8 is a schematic diagram of an exemplary multiplexed spatially-labelled capture spot. In FIG. 8, the capture spot 601 can be coupled to spatially-barcoded capture probes, where the spatially-barcoded probes of a particular capture spot can possess the same spatial barcode 605 but have different capture domains designed to associate the spatial barcode of the capture spot with more than one target analyte. For example, a capture spot may be coupled to four different types of spatially-barcoded capture probes, each type of spatially-barcoded capture probe possessing the spatial barcode 605. One type of capture probe associated with the capture spot includes the spatial barcode 605 in combination with a poly(T) capture domain 803, designed to capture mRNA target analytes. A second type of capture probe associated with the capture spot includes the spatial barcode 605 in combination with a random N-mer capture domain 804 for gDNA analysis. A third type of capture probe associated with the capture spot includes the spatial barcode 605 in combination with a capture domain complementary to the capture domain on an analyte capture agent 805. A fourth type of capture probe associated with the capture spot includes the spatial barcode 605 in combination with a capture probe that can specifically bind a nucleic acid molecule 806 that can function in a CRISPR assay (e.g., CRISPR/Cas9). While only four different capture probe-barcoded constructs are shown in FIG. 8, capture-probe barcoded constructs can be tailored for analyses of any given analyte associated with a nucleic acid and capable of binding with such a construct. For example, the schemes shown in FIG. 8 can also be used for concurrent analysis of other analytes disclosed herein, including, but not limited to: (a) mRNA, a lineage tracing construct, cell surface or intracellular proteins and metabolites, and gDNA; (b) mRNA, accessible chromatin (e.g., ATAC-seq, DNase-seq, and/or MNase-seq) cell surface or intracellular proteins and metabolites, and a perturbation agent (e.g., a CRISPR crRNA/sgRNA, TALEN, zinc finger nuclease, and/or antisense oligonucleotide as described herein); (c) mRNA, cell surface or intracellular proteins and/or metabolites, a barcoded labelling agent (e.g., the MEW multimers described herein), and a V(D)J sequence of an immune cell receptor (e.g., T-cell receptor). In some embodiments, a perturbation agent can be a small molecule, an antibody, a drug, an aptamer, a miRNA, a physical environmental (e.g., temperature change), or any other known perturbation agents.

In some embodiments, each respective probe spot in a plurality of probe spots is a physical probe spot (e.g., on a substrate). In some embodiments, a respective probe spot in a plurality of probe spots is a visual representation of a physical probe spot, such as an image of the probe spot and/or a two-dimensional position of the respective probe spot in a two-dimensional spatial arrangement of the plurality of probe spots.

In some embodiments, each respective probe at each respective probe spot is associated with a unique corresponding barcode. In some embodiments, each probe spot in the plurality of probe spots has a corresponding respective barcode, where each barcode is uniquely identifiable. The location of each barcode is known with regard to each other barcode (e.g., barcodes are spatially coded). An example of such measurement techniques for spatial probe spot based sequencing is disclosed in United States Patent Application Publication Nos. US2021-0062272 A1, entitled "Systems and Methods for Using the Spatial Distribution of Haplotypes to Determine a Biological Condition," published Mar. 4, 2021, and US2021-0155982 A1, entitled "Pipeline for Analysis of Analytes," published May 27, 2021, each of which is hereby incorporated by reference. In some embodiments, each respective probe spot comprises a plurality of corresponding probes with different corresponding barcodes.

In some embodiments, a capture spot on the array includes a bead. In some embodiments, two or more beads are dispersed onto a substrate to create an array, where each bead is a capture spot on the array.

Further details and non-limiting embodiments relating to capture spots are described in U.S. Patent Application Publication No. US2021-0062272, U.S. Patent Publication No. 20110059865A1, U.S. Provisional Patent Application No. 62/839,346, U.S. Pat. No. 9,012,022, and PCT publication No. 202020176788A1, entitled "Profiling of biological analytes with spatially barcoded oligonucleotide arrays"; U.S. Pat. No. 11,501,440, entitled "SYSTEMS AND METHODS FOR SPATIAL ANALYSIS OF ANALYTES USING FIDUCIAL ALIGNMENT," U.S. Patent Application Publication No. US2021-0150707, entitled "SYSTEMS AND METHODS FOR TISSUE CLASSIFICATION," published May 20, 2021; U.S. Pat. No. 11,514,575, entitled "Systems and Methods for Identifying Morphological Patterns in Tissue Samples,"; and U.S. Patent Application Publication No. US2021-0155982 A1, entitled "Pipeline for Spatial Analysis of Analytes," published May 27, 2021, each of which is hereby incorporated herein by reference in its entirety.

Capture Spot Arrays

In some embodiments, capture spots are collectively positioned on a substrate. As used herein, the term "capture spot array" or "array" refers to a specific arrangement of a plurality of capture spots (also termed "features") that is either irregular or forms a regular pattern. Individual capture spots in the array differ from one another based on their relative spatial locations. In general, at least two of the plurality of capture spots in the array include a distinct capture probe (e.g., any of the examples of capture probes described herein).

Arrays can be used to measure large numbers of analytes simultaneously. In some embodiments, oligonucleotides are used, at least in part, to create an array. For example, one or more copies of a single species of oligonucleotide (e.g., capture probe) can correspond to or be directly or indirectly attached to a given capture spot in the array. In some embodiments, a given capture spot in the array includes two or more species of oligonucleotides (e.g., capture probes). In some embodiments, the two or more species of oligonucleotides (e.g., capture probes) attached directly or indirectly to a given capture spot on the array include a common (e.g., identical) spatial barcode.

In some embodiments, a substrate and/or an array (e.g., two-dimensional array) comprises a plurality of capture spots. In some embodiments, a substrate and/or an array includes at least 50, at least 100, at least 200, at least 500, at least 1000, at least 2000, at least 5000, at least 10,000, at least 100,000, at least 500,000, or at least 1 million capture spots. In some embodiments, the two-dimensional array of capture spots comprises no more than 5 million, no more than 1 million, no more than 100,000, no more than 10,000, no more than 1000, or no more than 500 capture spots. In some embodiments, the two-dimensional array of capture spots comprises from 100 to 10,000, from 300 to 5000, from 2000 to 100,000, or from 50,000 to 500,000 capture spots. In some embodiments, the two-dimensional array of capture spots includes a plurality of capture spots that falls within another range starting no lower than 50 capture spots and ending no higher than 5 million capture spots.

Figure 9:
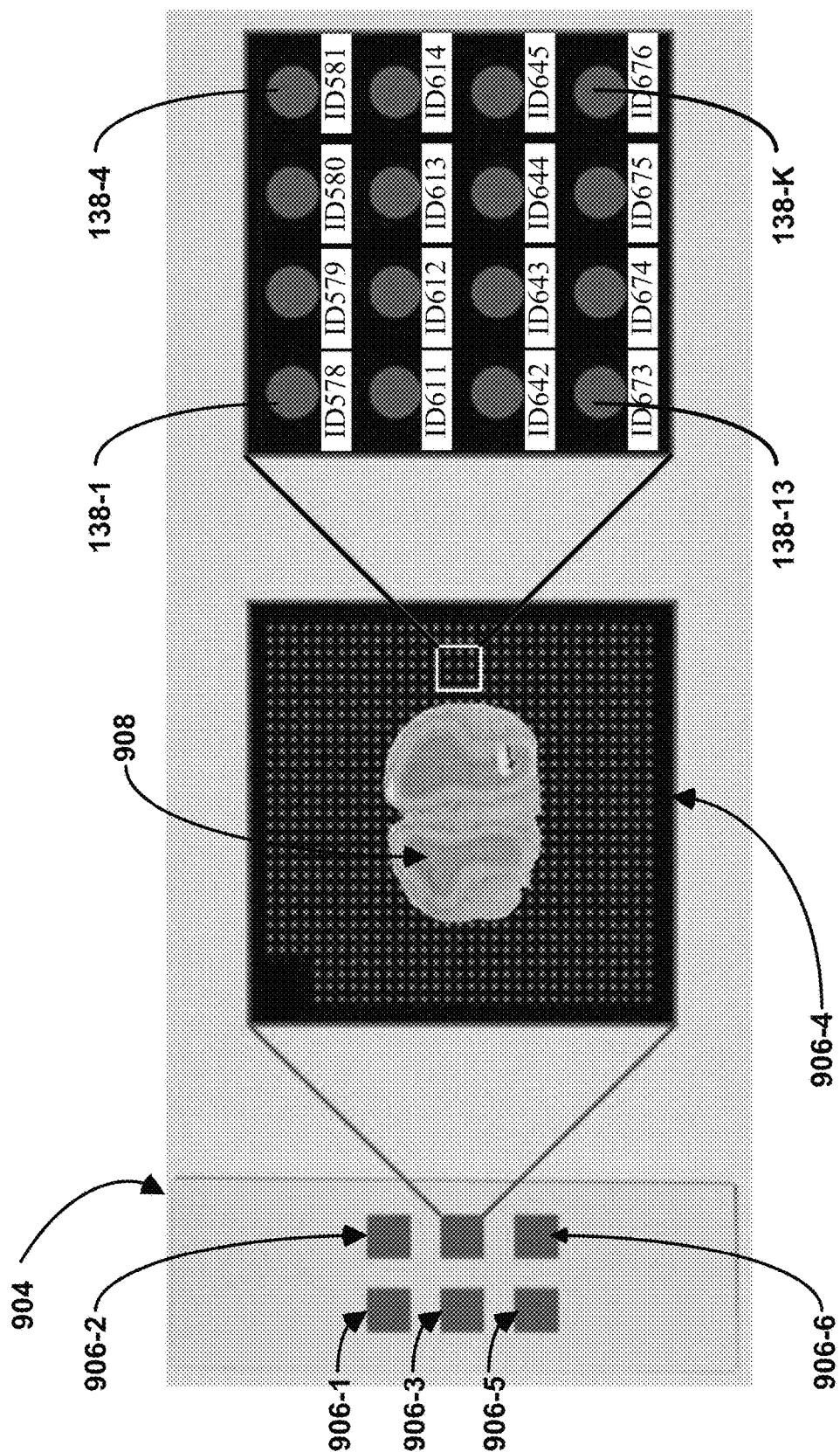
FIG. 9 is a schematic showing the arrangement of barcoded capture spots within a series of arrays, in accordance with an embodiment of the present disclosure.

FIG. 9 depicts an exemplary arrangement of barcoded capture spots within an array. From left to right, FIG. 9 shows (L) a slide 904 including six spatially-barcoded arrays 906 (e.g., 906-1, 906-2, 906-3, 906-4, 906-5, 906-6), (C) an enlarged schematic of one of the six spatially-barcoded arrays 906, showing a grid of barcoded capture spots in relation to a sample 908, and (R) an enlarged schematic of one section of an array, showing the specific identification of multiple capture spots 138 within the array (labelled as ID578, ID579, ID580, etc.).

Arrays suitable for use in the present disclosure are further described in PCT publication 202020176788A1, entitled "Profiling of biological analytes with spatially barcoded oligonucleotide arrays"; U.S. Pat. No. 11,501,440, entitled "SYSTEMS AND METHODS FOR SPATIAL ANALYSIS OF ANALYTES USING FIDUCIAL ALIGNMENT," U.S. Patent Application Publication No. US2021-0150707, entitled "SYSTEMS AND METHODS FOR TISSUE CLASSIFICATION," published May 20, 2021; U.S. Pat. No. 11,514,575, entitled "Systems and Methods for Identifying Morphological Patterns in Tissue Samples," published Apr. 1, 2021; and U.S. Patent Application Publication No. US2021-0155982 A1, entitled "Pipeline for Spatial Analysis of Analytes," published May 27, 2021, each of which is hereby incorporated herein by reference in its entirety.

Contact

As used herein, the terms "contact," "contacted," and/or "contacting" of a biological sample with a substrate comprising capture spots refers to any contact (e.g., direct or indirect) such that capture probes can interact (e.g., capture) with analytes from the biological sample. For example, the substrate may be near or adjacent to the biological sample without direct physical contact, yet capable of capturing analytes from the biological sample. In some embodiments the biological sample is in direct physical contact with the substrate. In some embodiments, the biological sample is in indirect physical contact with the substrate. For example, a liquid layer may be between the biological sample and the substrate. In some embodiments, the analytes diffuse through the liquid layer. In some embodiments the capture probes diffuse through the liquid layer. In some embodiments, reagents may be delivered via the liquid layer between the biological sample and the substrate. In some embodiments, indirect physical contact may be the presence of a second substrate (e.g., a hydrogel, a film, a porous membrane) between the biological sample and the first substrate comprising capture spots with capture probes. In some embodiments, reagents are delivered by the second substrate to the biological sample.

Generally, analytes can be captured when contacting a biological sample with, e.g., a substrate comprising capture probes (e.g., substrate with capture probes embedded, spotted, printed on the substrate or a substrate with capture spots (e.g., beads, wells) comprising capture probes). Capture can be performed using passive capture methods (e.g., gravity or diffusion) and/or active capture methods (e.g., electrophoresis).

In some embodiments, capture of analytes is facilitated by treating the biological sample with permeabilization reagents. If a biological sample is not permeabilized sufficiently, the amount of analyte captured on the substrate can be too low to enable adequate analysis. Conversely, if the biological sample is too permeable, the analyte can diffuse away from its origin in the biological sample, such that the relative spatial relationship of the analytes within the biological sample is lost. Hence, a balance between permeabilizing the biological sample enough to obtain good signal intensity while still maintaining the spatial resolution of the analyte distribution in the biological sample is desired. Methods of preparing biological samples to facilitate capture are known in the art and can be modified depending on the biological sample and how the biological sample is prepared (e.g., fresh frozen, FFPE, PFA, etc.). Examples of analyte capture suitable for use in the present disclosure are further described in U.S. Pat. No. 11,501,440, entitled "SYSTEMS AND METHODS FOR SPATIAL ANALYSIS OF ANALYTES USING FIDUCIAL ALIGNMENT," U.S. Patent Application Publication No. US2021-0150707, entitled "SYSTEMS AND METHODS FOR TISSUE CLASSIFICATION," published May 20, 2021; U.S. Pat. No. 11,514,575, entitled "Systems and Methods for Identifying Morphological Patterns in Tissue Samples," published Apr. 1, 2021; and U.S. Patent Application Publication No. US2021-0155982 A1, entitled "Pipeline for Spatial Analysis of Analytes," published May 27, 2021, each of which is hereby incorporated herein by reference in its entirety.

Fiducials

As used interchangeably herein, the terms "fiducial," "spatial fiducial," "fiducial marker," and "fiducial spot" generally refers to a point of reference or measurement scale. In some embodiments, imaging is performed using one or more fiducial markers, i.e., objects placed in the field of view of an imaging system that appear in the image produced. Fiducial markers can include, but are not limited to, detectable labels such as fluorescent, radioactive, chemiluminescent, calorimetric, and colorimetric labels. The use of fiducial markers to stabilize and orient biological samples is described, for example, in Carter et al., Applied Optics 46:421-427, 2007), the entire contents of which are incorporated herein by reference.

In some embodiments, a fiducial marker can be present on a substrate to provide orientation of the biological sample. In some embodiments, a microsphere can be coupled to a substrate to aid in orientation of the biological sample. In some examples, a microsphere coupled to a substrate can produce an optical signal (e.g., fluorescence). In another example, a microsphere can be attached to a portion (e.g., corner) of an array in a specific pattern or design (e.g., hexagonal design) to aid in orientation of a biological sample on an array of capture spots on the substrate. In some embodiments, a fiducial marker can be an immobilized molecule with which a detectable signal molecule can interact to generate a signal. For example, a fiducial marker nucleic acid can be linked or coupled to a chemical moiety capable of fluorescing when subjected to light of a specific wavelength (or range of wavelengths). Such a fiducial marker nucleic acid molecule can be contacted with an array before, contemporaneously with, or after the tissue sample is stained to visualize or image the tissue section. In some embodiments, it can be advantageous to use a fiducial marker that can be detected using the same conditions (e.g., imaging conditions) used to detect an analyte of interest.

In some embodiments, fiducial markers are included to facilitate the orientation of a tissue sample or an image thereof in relation to an immobilized capture probes on a substrate. Any number of methods for marking an array can be used such that a fiducial marker is detectable only when a tissue section is imaged. For instance, a molecule, e.g., a fluorescent molecule that generates a signal, can be immobilized directly or indirectly on the surface of a substrate. Fiducial markers can be provided on a substrate in a pattern (e.g., an edge, one or more rows, one or more lines, etc.).

In some embodiments, a fiducial marker can be stamped, attached, or synthesized on the substrate and contacted with a biological sample. Typically, an image (e.g., brightfield or fluorescence image) of the sample and the fiducial marker is taken, and the position of the fiducial marker on the substrate can be confirmed by viewing the image.

In some examples, fiducial markers can surround the array. In some embodiments the fiducial markers allow for detection of, e.g., mirroring. In some embodiments, the fiducial markers may completely surround the array (e.g., creating a fiducial board or frame). In some embodiments, the fiducial markers may not completely surround the array. In some embodiments, the fiducial markers identify the corners of the array. In some embodiments, one or more fiducial markers identify the center of the array.

Example fiducial markers suitable for use in the present disclosure are further described in U.S. Pat. No. 11,501,440, entitled "SYSTEMS AND METHODS FOR SPATIAL ANALYSIS OF ANALYTES USING FIDUCIAL ALIGNMENT," U.S. Patent Application Publication No. US2021-0150707, entitled "SYSTEMS AND METHODS FOR TISSUE CLASSIFICATION," published May 20, 2021; U.S. Pat. No. 11,514,575, entitled "Systems and Methods for Identifying Morphological Patterns in Tissue Samples," published Apr. 1, 2021; and U.S. Patent Application Publication No. US2021-0155982 A1, entitled "Pipeline for Spatial Analysis of Analytes," published May 27, 2021, each of which is hereby incorporated herein by reference in its entirety.

Genome

A "genome" generally refers to genomic information from a subject, which can be, for example, at least a portion of, or the entirety of, the subject's gene-encoded hereditary information. A genome can include coding regions (e.g., that code for proteins) as well as non-coding regions. A genome can include the sequences of some or all of the subject's chromosomes. For example, the human genome ordinarily has a total of 46 chromosomes. The sequences of some or all of these can constitute the genome.

Hybridizing, Hybridize, Annealing, and Anneal

The terms "hybridizing," "hybridize," "annealing," and "anneal" are used interchangeably in this disclosure and refer to the pairing of substantially complementary or complementary nucleic acid sequences within two different molecules. Pairing can be achieved by any process in which a nucleic acid sequence joins with a substantially or fully complementary sequence through base pairing to form a hybridization complex. For purposes of hybridization, two nucleic acid sequences are "substantially complementary" if at least 80% of their individual bases are complementary to one another.

Nucleic acid and Nucleotide

As used herein, the terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage including any of a variety of those known in the art. Naturally-occurring nucleic acids generally have a deoxyribose sugar (e.g., found in deoxyribonucleic acid (DNA)) or a ribose sugar (e.g., found in ribonucleic acid (RNA)).

A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Useful non-native bases that can be included in a nucleic acid or nucleotide are known in the art.

Primer

As used herein, a "primer" refers to a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. In general, primers are relatively short nucleic acid sequences, and typically include up to about 25 bases.

Primer Extension

A "primer extension" refers to any method where two nucleic acid sequences (e.g., a constant region from each of two distinct capture probes) become linked (e.g., hybridized) by an overlap of their respective terminal complementary nucleic acid sequences (i.e., for example, 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

Proximity Ligation

A "proximity ligation" is a method of ligating two (or more) nucleic acid sequences that are in proximity with each other through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between two nucleic acid molecules of interest (see, e.g., U.S. Pat. No. 7,264,929, the entire contents of which are incorporated herein by reference).

A wide variety of different methods can be used for proximity ligating nucleic acid molecules, including (but not limited to) "sticky-end" and "blunt-end" ligations. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

Subject

As used herein, the term "subject" refers to an animal, such as a mammal (e.g., human or a non-human simian), avian (e.g., bird), or other organism, such as a plant. Examples of subjects include, but are not limited to, a mammal such as a rodent, mouse, rat, rabbit, guinea pig, ungulate, horse, sheep, pig, goat, cow, cat, dog, primate (e.g., human or non-human primate); a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a Dictyostelium discoideum; a fungi such as *Pneumocystis carinii, Takifugu rubripes*, yeast, *Saccharomyces cerevisiae* or *Schizosaccharomyces pombe*; or a *Plasmodium falciparum*.

Substrates

As used herein, a "substrate" refers to a support that is insoluble in aqueous liquid and that allows for positioning of biological samples, analytes, capture spots, and/or capture probes on the substrate. For instance, a substrate can be any surface onto which a sample and/or capture probes can be affixed (e.g., a chip, solid array, a bead, a slide, a coverslip, a wafer, etc.). For the spatial analytical methods described in this section, a substrate is used to provide support to a biological sample, particularly, for example, a tissue section. In addition, in some embodiments, a substrate (e.g., the same substrate or a different substrate) functions as a support for direct or indirect attachment of capture probes to capture spots of the array.

A wide variety of different substrates can be used for the foregoing purposes. In general, a substrate can be any suitable support material. Exemplary substrates include, but are not limited to, glass, modified and/or functionalized glass, hydrogels, films, membranes, plastics (including e.g., acrylics, polystyrene, copolymers of styrene and other materials, polypropylene, polyethylene, polybutylene, polyurethanes, Teflon", cyclic olefins, polyimides, etc.), nylon, ceramics, resins, Zeonor, silica or silica-based materials including silicon and modified silicon, carbon, metals, inorganic glasses, optical fiber bundles, and polymers, such as polystyrene, cyclic olefin copolymers (COCs), cyclic olefin polymers (COPs), polypropylene, polyethylene and polycarbonate.

The substrate can also correspond to a flow cell. Flow cells can be formed of any of the foregoing materials, and can include channels that permit reagents, solvents, capture spots, and molecules to pass through the flow cell.

The substrate can generally have any suitable form or format. For example, the substrate can be flat, curved, e.g., convexly or concavely curved towards the area where the interaction between a biological sample, e.g., tissue sample, and the substrate takes place. In some embodiments, the substrate is a flat, e.g., planar, chip, die or slide. The substrate can contain one or more patterned surfaces within the substrate (e.g., channels, wells, projections, ridges, divots, etc.). A substrate can be of any desired shape. For example, a substrate can be typically a flat shape (e.g., a square or a rectangle). In some embodiments, a substrate structure has rounded corners (e.g., for increased safety or robustness). In some embodiments, a substrate structure has one or more cut-off corners (e.g., for use with a slide clamp or cross-table). In some embodiments, where a substrate structure is flat, the substrate structure can be any appropriate type of support having a flat surface (e.g., a chip or a slide such as a microscope slide).

In some embodiments, a substrate includes one or more markings on a surface of the substrate, e.g., to provide guidance for correlating spatial information with the characterization of the analyte of interest. For example, a substrate can be marked with a grid of lines (e.g., to allow the size of objects seen under magnification to be easily estimated and/or to provide reference areas for counting objects). In some embodiments, fiducials (e.g., fiducial markers, fiducial spots, or fiducial patterns) can be included on the substrate. Fiducials can be made using techniques including, but not limited to, printing, sand-blasting, etching, and depositing (e.g., chrome or titanium) on the surface. In some embodiments, the substrate (e.g., or a bead or a capture spot on an array) includes a plurality of oligonucleotide molecules (e.g., capture probes). In some embodiments, the substrate includes tens to hundreds of thousands or millions of individual oligonucleotide molecules (e.g., at least about 10,000, 50,000, 100,000, 500,000, 1,000,000, 10,000,000, 100,000,000, 1,000,000,000 or 10,000,000,000 oligonucleotide molecules). In some embodiments, a substrate can include a substrate identifier, such as a serial number.

Further examples of substrates, including for example fiducial markers on such substrates, are disclosed in PCT publication 202020176788A1, entitled "Profiling of biological analytes with spatially barcoded oligonucleotide arrays"; U.S. Pat. No. 11,501,440, entitled "SYSTEMS AND METHODS FOR SPATIAL ANALYSIS OF ANALYTES USING FIDUCIAL ALIGNMENT," U.S. Patent Application Publication No. US2021-0150707, entitled "SYSTEMS AND METHODS FOR TISSUE CLASSIFICATION," published May 20, 2021; U.S. Pat. No. 11,514,575, entitled "Systems and Methods for Identifying Morphological Patterns in Tissue Samples," published Apr. 1, 2021; and U.S. Patent Application Publication No. US2021-0155982 A1, entitled "Pipeline for Spatial Analysis of Analytes," published May 27, 2021, each of which is hereby incorporated herein by reference in its entirety.

Spatial Analyte Data

As used herein, "spatial analyte data" refers to any data measured, either directly, from the capture of analytes on capture probes, or indirectly, through intermediate agents disclosed herein that bind to analytes in a sample, e.g., connected probes disclosed herein, analyte capture agents or portions thereof (such as, e.g., analyte binding moieties and their associated analyte binding moiety barcodes). Spatial analyte data thus may, in some aspects, include two different labels from two different classes of barcodes. One class of barcode identifies the analyte, while the other class of barcodes identifies the specific capture probe in which an analyte was detected.

Template Switching Oligonucleotide

As used herein, the term "template switching oligonucleotide" refers to an oligonucleotide that hybridizes to untemplated poly(C) nucleotides added by a reverse transcriptase (e.g., enzyme with terminal transferase activity) during reverse transcription. In some embodiments, the template switching oligonucleotide adds a common 5' sequence to full-length cDNA that is used for cDNA amplification. In some embodiments, a template switching oligonucleotide is added before, contemporaneously with, or after a reverse transcription, or other terminal transferase-based reaction. In some embodiments, a template switching oligonucleotide is included in the capture probe. In certain embodiments, methods of sample analysis using template switching oligonucleotides can involve the generation of nucleic acid products from analytes of the tissue sample, followed by further processing of the nucleic acid products with the template switching oligonucleotide.

Template switching oligonucleotides can include a hybridization region and a template region. The hybridization region can include any sequence capable of hybridizing to the target. In some embodiments, the hybridization region includes a series of G bases to complement the overhanging C bases at the 3' end of a cDNA molecule. The series of G bases can include 1 G base, 2 G bases, 3 G bases, 4 G bases, 5 G bases, or more than 5 G bases. The template sequence can include any sequence to be incorporated into the cDNA. In some embodiments, the template region includes at least 1 (e.g., at least 2, 3, 4, 5 or more) tag sequences and/or functional sequences. In some embodiments, the template region and hybridization region are separated by a spacer.

In some embodiments, the template regions include a barcode sequence. The barcode sequence can act as a spatial barcode and/or as a unique molecular identifier. Template switching oligonucleotides can include deoxyribonucleic acids; ribonucleic acids; modified nucleic acids including 2-aminopurine, 2,6-diaminopurine (2-amino-dA), inverted dT, 5-methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' fluoro bases (e.g., Fluoro C, Fluoro U, Fluoro A, and Fluoro G), or any combination of the foregoing.

In some embodiments, the length of a template switching oligonucleotide can be at least about 2, 10, 20, 50, 75, 100, 150, 200, or 250 nucleotides or longer. In some embodiments, the length of a template switching oligonucleotide can be at most about 2, 10, 20, 50, 100, 150, 200, or 250 nucleotides or longer.

Template switching is described, for example, in U.S. Pat. No. 11,501,440, entitled "SYSTEMS AND METHODS FOR SPATIAL ANALYSIS OF ANALYTES USING FIDUCIAL ALIGNMENT," U.S. Patent Application Publication No. US2021-0150707, entitled "SYSTEMS AND METHODS FOR TISSUE CLASSIFICATION," published May 20, 2021; U.S. Pat. No. 11,514,575, entitled "Systems and Methods for Identifying Morphological Patterns in Tissue Samples," published Apr. 1, 2021; and U.S. Patent Application Publication No. US2021-0155982 A1, entitled "Pipeline for Spatial Analysis of Analytes," published May 27, 2021, each of which is hereby incorporated herein by reference in its entirety.

Methods for Spatial Analysis of Analytes.

Array-based spatial analysis methods involve the capture of one or more analytes and/or proxies from a biological sample to an array of capture spots on a substrate, each of which is associated with a unique spatial location on the array. Subsequent analysis of the captured analytes and/or proxies includes determining the identity of the analytes and the spatial location of each analyte within the sample. The spatial location of each analyte within the sample is determined based on the capture spot to which each analyte is bound in the array, and the capture spot's relative spatial location within the array.

The spatial analysis methodologies disclosed herein provide for the detection of differences in analyte levels between different cells in a tissue of a mammal or between single cells in a population of cells. For example, spatial analysis methodologies can be used to detect the differences in analyte levels between different cells in histological slide samples, the data from which can be reassembled to generate a three-dimensional map of analyte levels of a sample (e.g., a tissue sample) obtained from a mammal, with a degree of spatial resolution such as single-cell resolution.

There are several general methods to associate a spatial barcode with a region of a sample (e.g., one or more neighboring cells in a tissue section), such that the spatial barcode identifies the region of the sample, and/or the contents thereof, as associated with a particular spatial location. One general method is to promote analytes or analyte proxies (e.g., intermediate agents and/or ligation products) out of a cell and towards a spatially-barcoded array (e.g., including spatially-barcoded capture probes). In some instances, the spatially-barcoded array populated with capture probes (as described further herein) is contacted with a biological sample, and the biological sample is permeabilized, allowing the analyte to migrate away from the sample and toward the array. The analyte interacts with a capture probe on the spatially-barcoded array. Once the target analyte and/or proxy is captured by the capture probe, the sample is optionally removed from the array and the capture probes are analyzed in order to obtain spatially-resolved analyte information.

Another general method is to cleave spatially-barcoded capture probes from an array and promote the spatially-barcoded capture probes towards and/or into or onto the sample. In an exemplary embodiment of this general method, the spatially-barcoded array populated with capture probes (as described further herein) can be contacted with a sample. The spatially-barcoded capture probes are cleaved from the array, and subsequently interact with cells within the provided sample. The interaction can be a covalent or non-covalent cell-surface interaction. The interaction can be an intracellular interaction facilitated by a delivery system or a cell penetration peptide. Once the spatially-barcoded capture probe is associated with a particular cell, the sample can be optionally removed for analysis. The sample can be optionally dissociated before analysis. Once the tagged cell is associated with the spatially-barcoded capture probe, the capture probes can be analyzed to obtain spatially-resolved information about the tagged cell.

For instance, one exemplary workflow utilizes a spatially-barcoded array on a substrate (e.g., chip), where spatially-barcoded capture probes are clustered at areas called capture spots. The spatially-labelled capture probes can include a cleavage domain, one or more functional sequences, a spatial barcode, a unique molecular identifier, and a capture domain. The spatially-labelled capture probes can also include a 5' end modification for reversible attachment to the substrate. The spatially-barcoded array is contacted with a sample, and the sample is permeabilized through application of permeabilization reagents. Permeabilization reagents may be administered by placing the array/sample assembly within a bulk solution. Alternatively, permeabilization reagents may be administered to the sample via a diffusion-resistant medium and/or a physical barrier such as a lid, where the sample is sandwiched between the diffusion-resistant medium and/or barrier and the array-containing substrate. The analytes can migrate toward the spatially-barcoded capture array, or the cleaved spatially-barcoded capture probes migrate toward the sample, using any number of techniques disclosed herein. For example, analyte, proxy, and/or capture probe migration can occur using a diffusion-resistant medium lid and passive migration. As another example, analyte and/or capture probe migration can be active migration, using an electrophoretic transfer system, for example. Once the analytes and/or proxies are in close proximity to the spatially-barcoded capture probes, the capture probes can hybridize or otherwise bind a target analyte and/or proxy. The sample can be optionally removed from the array.

In some embodiments, once the analytes and/or proxies are captured by the capture probes, the captured analytes and/or proxies can be spatially-barcoded by performing a reverse transcriptase first strand cDNA reaction. A first strand cDNA reaction can be optionally performed using template switching oligonucleotides. For example, a template switching oligonucleotide can hybridize to a poly(C) tail added to a 3' end of the cDNA by a reverse transcriptase enzyme. The original mRNA template and template switching oligonucleotide can then be denatured from the cDNA, allowing the spatially-barcoded capture probe to hybridize with the cDNA and a complement of the cDNA to be generated. The first strand cDNA can then be purified and collected for downstream amplification steps. The first strand cDNA can be optionally amplified using PCR, where forward and reverse primers flank the spatial barcode and target analyte or proxy regions of interest, generating a nucleic acid library associated with a particular spatial barcode. In some embodiments, the nucleic acid library preparation can be quantified and/or subjected to quality control to verify the success of the library preparation steps. In some embodiments, the cDNA comprises a sequencing by synthesis (SBS) primer sequence. The nucleic acid library amplicons are sequenced and analyzed to decode spatial information.

In some embodiments, the sample is removed from the spatially-barcoded array and the spatially-barcoded capture probes are removed from the array for barcoded analyte amplification and library preparation. Another embodiment includes performing first strand synthesis using template switching oligonucleotides on the spatially-barcoded array without cleaving the capture probes from the array. In some such embodiments, sample preparation and permeabilization are performed as described elsewhere herein. Once the capture probes capture the target analyte(s), first strand cDNA created by template switching and reverse transcriptase is then denatured, and the second strand is then extended. The second strand cDNA is then denatured from the first strand cDNA and transferred off of the array (e.g., to a microtube). cDNA quantification and amplification can be performed using standard techniques discussed herein. The cDNA can then be subjected to library preparation and indexing, including fragmentation, end-repair, and A-tailing, and indexing PCR steps. The library can also be optionally tested for quality control (QC).

Yet another general method for spatial analysis comprises detecting multiple oligonucleotides that hybridize to an analyte. In some instances, for example, spatial analysis can be performed using RNA-templated ligation (RTL). Methods of RTL have been described previously. See, e.g., Credle et al., Nucleic Acids Res. 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., T4DNA ligase or SplintR ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNAse H). The released ligation product can then be captured by capture probes (e.g., instead of direct capture of an analyte) on an array, optionally amplified, and sequenced, thus determining the location and optionally the abundance of the analyte in the biological sample. Advantageously, this method allows for detection of analytes in cases where analyte transfer is difficult. For instance, biological samples prepared using fixed formalin paraffin embedding (FFPE) can experience crosslinking of RNA analytes, which can further undergo degradation over time. In some cases, such cross-linked RNA molecules migrate poorly or not at all, thus hindering analyte capture. The use of intermediate agents such as probes allows indirect capture of the RNA analytes via the migration of probes into the sample and subsequent migration of ligation products to capture probes. See, for example, the sections entitled "Definitions: Analytes" and "Definitions: Capture Probes," above.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes or proxies they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that, at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes, analytes, and/or proxies during analysis of spatial information, the locations of the capture probes and/or analytes can be determined by referring to the stored information that uniquely associates each spatial barcode with an array feature location. In this manner, specific capture probes and captured analytes and/or proxies are associated with specific locations in the array of features. Each array feature location represents a position relative to a coordinate reference point (e.g., an array location, a fiducial marker) for the array. Accordingly, each feature location has an "address" or location in the coordinate space of the array.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. patent application Ser. No. 16/951,864.

For example, in some instances, sample preparation may include placing the sample on a slide, fixing the sample, and/or staining the sample for imaging. The stained sample can be then imaged on the array using both brightfield (to image the sample stain) and/or fluorescence (to image features) modalities. Optionally, the sample can be destained prior to permeabilization. As described above, in some embodiments, analytes are captured by any means disclosed herein. The biological sample and array are then optionally imaged a second time in one or both modalities while the analytes are reverse transcribed into cDNA, and an amplicon library is prepared and sequenced. Images are then spatially-overlaid in order to correlate spatially-identified biological sample information. When the sample and array are not imaged a second time, a spot coordinate file can be supplied instead, where the spot coordinate file replaces the second imaging step.

In some cases, a map of analyte data (e.g., a presence and/or an amount of analytes) can be aligned to an image of a biological sample using one or more fiducial markers, e.g., objects placed in the field of view of an imaging system which appear in the image produced, as described in WO 2020/123320, PCT Application No. 2020/061066, and/or U.S. patent application Ser. No. 16/951,843. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

For instance, in some embodiments, a respective image is aligned to a plurality of features on a substrate by a procedure that comprises analyzing an array of pixel values in the respective image to identify a plurality of fiducial markers of the respective image. The fiducial markers are aligned with a corresponding plurality of reference fiducial markers using an alignment algorithm to obtain a transformation between the plurality of fiducial markers of the respective image and the corresponding plurality of reference fiducial markers. The transformation and a coordinate system corresponding to the plurality of reference fiducial markers are then used to locate a corresponding position in the respective image of each feature in a plurality of features.

Depending on the biological sample and the nature of analyte expression within the biological sample, morphological patterns obtained from spatial analysis of analytes can provide valuable insight into the underlying biological sample. For instance, the morphological patterns can be used to determine a disease state of the biological sample. As another example, the morphological pattern can be used to recommend a therapeutic treatment for the donor of the biological sample.

Specifically, in some embodiments, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder. Furthermore, in some embodiments, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Non-limiting aspects of spatial analysis methodologies and compositions are described in U.S. Pat. Nos. 10,774,374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodrigues et al., Science 363(6434):1463-1467, 2019; Lee et al., Nat. Protoc. 10(3):442-458, 2015; Trejo et al., PLoS ONE 14(2): e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10X Genomics Support Documentation website, and can be used herein in any combination. Further non-limiting aspects of spatial analysis methodologies and compositions are described herein.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments. These embodiments are non-limiting and do not preclude any alternatives, variations, changes, and substitutions that can occur to those skilled in the art from the scope of this disclosure.

Exemplary System Embodiments.

FIG. 1 is a block diagram illustrating an exemplary, non-limiting system for spatial analysis of analytes in accordance with some implementations. The system 100 in some implementations includes one or more processing units CPU(s) 102 (also referred to as processors), one or more network interfaces 104, a user interface 106, a memory 112, and one or more communication buses 114 for interconnecting these components. The communication buses 114 optionally include circuitry (sometimes called a chipset) that interconnects and controls communications between system components. The memory 112 typically includes high-speed random access memory, such as DRAM, SRAM, DDR RAM, ROM, EEPROM, flash memory, CD-ROM, digital versatile disks (DVD) or other optical storage, magnetic cassettes, magnetic tape, magnetic disk storage or other magnetic storage devices, other random access solid state memory devices, or any other medium which can be used to store desired information; and optionally includes non-volatile memory, such as one or more magnetic disk storage devices, optical disk storage devices, flash memory devices, or other non-volatile solid state storage devices. The memory 112 optionally includes one or more storage devices remotely located from the CPU(s) 102. The memory 112, or alternatively the non-volatile memory device(s) within the memory 112, comprises a non-transitory computer readable storage medium. It will be appreciated that this memory 112 can be distributed across one or more computers. In some implementations, the memory 112 or alternatively the non-transitory computer readable storage medium stores the following programs, modules and data structures, or a subset thereof:

- an optional operating system 116, which includes procedures for handling various basic system services and for performing hardware dependent tasks;
- an optional network communication module (or instructions) 118 for connecting the device 100 with other devices, or a communication network;
- a data structure 120 comprising an image 122 of a sample on a substrate, where the image includes a plurality of pixel values 124 (e.g., 124-1, . . . 124-N), each respective pixel value in the plurality of pixel values corresponding to a pixel in an array of pixels, and a first plurality of fiducial markers 126 (e.g., 126-1, . . . 126-L), where each respective fiducial marker in the first plurality of fiducial markers has a respective location 128 (e.g., 128-1) obtained by analyzing the plurality of pixel values and encodes a different N-digit code 130 (e.g., 130-1);
- a template repository 132 comprising at least a first template 134 (e.g., 134-1) that includes a location for each reference fiducial marker 136 in a plurality of reference fiducial markers (e.g., 136-1-1, . . . 136-1-P), a location for each capture spot 138 in a set of capture spots on the substrate (e.g., 138-1-1, . . . 138-1-K), and a coordinate system 140 for registering the image 122 to the set of capture spots 138;
- a pixel analysis module 142 for analyzing the plurality of pixel values 124 to identify the respective location 128 of each fiducial marker 126 in the first plurality of fiducial markers;
- an alignment module 144 for aligning the respective location 128 of each fiducial marker 126 in the first plurality of fiducial markers within the image 122 with the location of each reference fiducial marker 136 in the plurality of reference fiducial markers of the first template 134 to obtain a final transformation between the first plurality of fiducial markers of the image and the plurality of reference fiducial markers of the first template; and
- an analyte data store 146 comprising spatial analyte data 148 (e.g., 148-1, . . . 148-K) for each respective capture spot in the set of capture spots on the substrate that is used for analyzing the image after registration.

In some implementations, the user interface 106 includes an input device (e.g., a keyboard, a mouse, a touchpad, a track pad, and/or a touch screen) 110 for a user to interact with the system 100 and a display 108.

In some implementations, one or more of the above identified elements are stored in one or more of the previously mentioned memory devices, and correspond to a set of instructions for performing a function described above. The above identified modules or programs (e.g., sets of instructions) need not be implemented as separate software programs, procedures or modules, and thus various subsets of these modules may be combined or otherwise re-arranged in various implementations. In some implementations, the memory 112 optionally stores a subset of the modules and data structures identified above. Furthermore, in some embodiments, the memory stores additional modules and data structures not described above. In some embodiments, one or more of the above identified elements is stored in a computer system, other than that of system 100, that is addressable by system 100 so that system 100 may retrieve all or a portion of such data when needed.

Although FIG. 1 shows an exemplary system 100, the figure is intended more as functional description of the various features that may be present in computer systems than as a structural schematic of the implementations described herein. In practice, and as recognized by those of ordinary skill in the art, items shown separately could be combined and some items could be separated.

Embodiments for Spatial Analysis of Analytes Using Fiducial Alignment.

FIGS. 2A-I collectively illustrate a method 200 for spatial analysis of analytes. In some embodiments, the method takes place at a computer system 100 having one or more processors 102, and memory 112 storing one or more programs for execution by the one or more processors 102. It will be appreciated that the memory can be on a single computer, distributed across several computers, in one or more virtual machines and/or in a cloud computing architecture.

Referring to Block 202, the method includes obtaining a data structure, in electronic form, comprising an image 122 of a sample on a substrate. The substrate includes a plurality of border regions, where each respective border region in the plurality of border regions intersects another border region in the plurality of border regions. In some embodiment the substrate includes, one, two, three or four border regions.

In some such embodiments, the substrate includes at least a first plurality of fiducial markers 126. In some embodiments, the first plurality of fiducial markers is 2, 3, 4, 5, 6, 7, 8, 9, 10, 11, 12, 13, 14, 15, 16, 17, 18, 19, 20, or more fiducial markers. In some embodiments, the first plurality of fiducial markers is between 2 and 200 fiducial markers.

In some embodiments one or more fiducial markers in the plurality of fiducial markers is in a first border region, one or more fiducial markers in the plurality of fiducial markers is in a second border region, and one or more fiducial markers in the plurality of fiducial markers is in a third border region in the plurality of border regions.

In some embodiments one or more fiducial markers in the plurality of fiducial markers is in a first border region, one or more fiducial markers in the plurality of fiducial markers is in a second border region, one or more fiducial markers in the plurality of fiducial markers is in a third border region, and one or more fiducial markers in the plurality of fiducial markers is in a fourth border region in the plurality of border regions.

In some embodiments two or more fiducial markers in the plurality of fiducial markers is in a first border region, two or more fiducial markers in the plurality of fiducial markers is in a second border region, and two or more fiducial markers in the plurality of fiducial markers is in a third border region in the plurality of border regions.

In some embodiments two or more fiducial markers in the plurality of fiducial markers is in a first border region, two or more fiducial markers in the plurality of fiducial markers is in a second border region, two or more fiducial markers in the plurality of fiducial markers is in a third border region, and two or more fiducial markers in the plurality of fiducial markers is in a fourth border region in the plurality of border regions.

In some embodiments, the first plurality of fiducial markers 126 comprises at least three fiducial markers.

In some embodiments, each respective fiducial marker 126 in the first plurality of fiducial markers encodes a different N-digit code 130, in a plurality of N-digit codes, where N is an integer greater than 3.

In some embodiments at least two different border regions in the plurality of border regions includes a respective fiducial marker 126 in the first plurality of fiducial markers.

In some such embodiments, the substrate includes a set of capture spots (e.g., where the set of capture spots comprises at least 1000 capture spots). In some embodiments the set of capture spots comprises at least 500 capture spots, at least 1000 capture spots, at least 2000 capture spots, at least 5000 capture spots, or at least 10,000 capture spots.

In some embodiments, the image 122 comprises a plurality of pixel values 124, each respective pixel value in the plurality of pixel values corresponding to a pixel in an array of pixels (e.g., where the array of pixels comprises at least 100,000 pixels). In some embodiments, the array of pixels comprises at least 1000 pixels, at least 10,000 pixels, at least 100,000 pixels, at least 500,000 pixels or at least $1 \times 10^6$ pixels. In some embodiments, each such pixel is a RGB pixel. In some embodiments, each such pixel is a grey-scaled pixel.

In some implementations, an image is obtained in any electronic image file format, including but not limited to JPEG/JFIF, TIFF, Exif, PDF, EPS, GIF, BMP, PNG, PPM, PGM, PBM, PNM, WebP, HDR raster formats, HEIF, BAT, BPG, DEEP, DRW, ECW, FITS, FLIF, ICO, ILBM, IMG, PAM, PCX, PGF, JPEG XR, Layered Image File Format, PLBM, SGI, SID, CD5, CPT, PSD, PSP, XCF, PDN, CGM, SVG, PostScript, PCT, WMF, EMF, SWF, XAML, and/or RAW.

Referring to Block 204, in some embodiments, the image is acquired using transmission light microscopy or fluorescent microscopy.

For example, in some embodiments the image is acquired using transmission light microscopy. In some embodiments, the sample is stained prior to imaging using, e.g., fluorescent, radioactive, chemiluminescent, calorimetric, or colorimetric detectable markers. In some embodiments, the sample is stained using live/dead stain (e.g., trypan blue). In some embodiments, samples are stained by any of the methods disclosed herein (see, e.g., the section entitled "Biological Samples," above). In some embodiments, the image is acquired using optical microscopy (e.g., bright field, dark field, dispersion staining, phase contrast, differential interference contrast, interference reflection, fluorescence, confocal, single plane illumination, wide-field multiphoton, deconvolution, transmission electron microscopy, and/or scanning electron microscopy). In some embodiments, the image is acquired after staining the tissue section. In some embodiments, the image is acquired prior to or during analyte capture (e.g., of a plurality of analytes, as further described in the section entitled "Analytes," above). In some embodiments, the sample is subjected to immunohistochemistry prior to image acquisition and fluorescence microscopy is used to acquire the image. In some such embodiments, the image is acquired using Epi-illumination mode, where both the illumination and detection are performed from one side of the sample. In some such embodiments, the image is acquired using confocal microscopy, two-photon imaging, wide-field multiphoton microscopy, single plane illumination microscopy or light sheet fluorescence microscopy. See, for example, *Adaptive Optics for Biological Imaging*, 2013, Kubby ed., CRC Press, Boca Raton, Florida; and *Confocal and Two-Photon Microscopy: Foundations, Applications and Advances*, 2002, Diaspro ed., Wiley Liss, New York, New York; and *Handbook of Biological Confocal Microscopy*, 2002, Pawley ed., Springer Science+Business Media, LLC, New York, New York each of which is hereby incorporated by reference.

In some embodiments, the image is a color image (e.g., 3×8 bit, 2424×2424 pixel resolution). In some embodiments, the image is a monochrome image (e.g., 14 bit, 2424×2424 pixel resolution). In some embodiments, the image is obtained in any electronic color mode, including but not limited to grayscale, bitmap, indexed, RGB, CMYK, HSV, lab color, duotone, and/or multichannel. In some embodiments, the image is manipulated (e.g., stitched, compressed and/or flattened). In some embodiments, the image file size is between 1 KB and 1 MB, between 1 MB and 0.5 GB, between 0.5 GB and 5 GB, between 5 GB and 10 GB, or greater than 10 GB.

In some embodiments, the image is represented as an array (e.g., matrix) comprising a plurality of pixels, such that the location of each respective pixel in the plurality of pixels in the array (e.g., matrix) corresponds to its original location in the image. In some embodiments, the image is represented as a vector comprising a plurality of pixels, such that each respective pixel in the plurality of pixels in the vector comprises spatial information corresponding to its original location in the image.

In some embodiments, the array of pixels comprises at least 100, at least 1000, at least 10,000, at least 50,000, at least 100,000, at least 500,000, at least $1 \times 10^6$, at least $2 \times 10^6$, at least $3 \times 10^6$, at least $5 \times 10^6$, at least $8 \times 10^6$, at least $1 \times 10^7$, or at least $1.5 \times 10^7$ pixels. In some embodiments, the array of pixels comprises no more than $2 \times 10^7$, no more than $1 \times 10^7$, no more than $5 \times 10^6$, no more than $1 \times 10^6$, no more than 500,000, no more than 100,000, or no more than 10,000 pixels. In some embodiments, the array of pixels comprises from 1000 to 500,000, from 10,000 to $1 \times 10^6$, from 100,000 to $3 \times 10^6$, or from $1 \times 10^6$ to $1 \times 10^7$ pixels. In some embodiments, the array of pixels comprises another range of pixels starting no lower than 100 pixels and ending no higher than $1 \times 10^7$ pixels.

In some embodiments, the image of the sample on the substrate is obtained using any suitable substrate, as disclosed herein (see, e.g., the section entitled "Substrates," above). As described above, substrates are generally used to provide support to a sample, such as a thin tissue section. In some embodiments, a substrate is a support that allows for positioning of samples, analytes, capture spots, and/or capture probes.

In some embodiments, the substrate is a wafer, or subset thereof (e.g., die) or a glass slide. In some embodiments, a substrate comprises any suitable support material, including, but not limited to, glass, modified and/or functionalized glass, hydrogels, films, membranes, plastics (including e.g., acrylics, polystyrene, copolymers of styrene and other materials, polypropylene, polyethylene, polybutylene, polyurethanes, TEFLON®, cyclic olefins, polyimides, etc.), nylon, ceramics, resins, Zeonor, silica or silica-based materials including silicon and modified silicon, carbon, metals, inorganic glasses, optical fiber bundles, and polymers, such as polystyrene, cyclic olefin copolymers (COCs), cyclic olefin polymers (COPs), polypropylene, polyethylene and polycarbonate. In some embodiments, a substrate is printed, patterned, or otherwise modified to comprise capture spots that allow association with analytes upon contacting a sample (e.g., a tissue section). In some embodiments, the substrate comprises a capture area, where the capture area comprises a plurality of barcoded capture spots. In some embodiments, the substrate comprises 2, 3, 4, 5, 6, 7, 8, 9, 10, 11, 12, 13, 14, 15, 16, 17, 18, 19, 20, more than 20, more than 30, more than 40, or more than 50 capture areas.

In some embodiments, the sample is obtained from a subject. As defined above, in some embodiments, a subject is a mammal such as a rodent, mouse, rat, rabbit, guinea pig, ungulate, horse, sheep, pig, goat, cow, cat, dog, primate (e.g., human or non-human primate); a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a Dictyostelium discoideum; a fungi such as *Pneumocystis carinii*, *Takifugu rubripes*, yeast, *Saccharomyces cerevisiae* or *Schizosaccharomyces pombe*; or a *Plasmodium falciparum*. These examples are non-limiting and do not preclude substitution of any alternative subjects that will occur to one skilled in the art.

In some embodiments, the sample is a tissue sample, and the tissue sample is obtained from any tissue and/or organ derived from any subject, including but not limited to those subjects listed above. In some embodiments, a tissue sample is obtained from, e.g., heart, kidney, ovary, breast, lymph node, adipose, brain, small intestine, stomach, liver, quadriceps, lung, testes, thyroid, eyes, tongue, large intestine, spleen, and/or mammary gland, skin, muscle, diaphragm, pancreas, bladder, prostate, among others. Tissue samples can be obtained from healthy or unhealthy tissue (e.g., inflamed, tumor, carcinoma, or other). In some embodiments, the sample comprises a plurality of individual cells (e.g., a cell suspension and/or a plurality of disaggregated cells). In some embodiments, the sample consists of a plurality of individual cells (e.g., a cell suspension and/or a plurality of disaggregated cells). Other suitable samples that are contemplated for use in the present disclosure are described, for instance, in the section entitled "Biological samples," above.

In some embodiments, the sample is a sectioned tissue sample. In some such embodiments, the sectioned tissue is prepared by tissue sectioning, as described above (see, e.g., the section entitled "Biological samples," above). Referring to Block 206, in some embodiments, the sample is a sectioned tissue sample, and the sectioned tissue sample has a depth of 30 microns or less. In some embodiments, the sample is a sectioned tissue sample having a depth of 100 microns or less, 80 microns or less, 70 microns or less, 60 microns or less, 50 microns or less, 40 microns or less, 30 microns or less, 20 microns or less, 15 microns or less, 10 microns or less, 5 microns or less, or 1 micron or less. In some embodiments, the sectioned tissue sample has a depth of from 10 microns to 20 microns, from 3 microns to 50 microns, from 5 microns to 10 microns, or from 10 microns to 100 microns. In some embodiments, the sectioned tissue sample has a depth that falls within another range starting no lower than 1 micron and ending no higher than 100 microns.

In some embodiments, a tissue section is a similar size and shape to the substrate on which it is placed. In some embodiments, a tissue section is a different size and shape from the substrate on which it is placed. In some embodiments, a tissue section overlays all or a portion of the substrate. In some embodiments, a tissue section on a substrate is a single uniform section. In some alternative embodiments, multiple tissue sections are on a substrate. In some such embodiments, a single capture area on a substrate can contain multiple tissue sections, where each tissue section is obtained from either the same sample and/or subject or from different samples and/or subjects. In some embodiments, a tissue section is a single tissue section that comprises one or more regions where no cells are present (e.g., holes, tears, or gaps in the tissue). Thus, in some embodiments such as the above, an image of a tissue section on a substrate can contain regions where tissue is present and regions where tissue is not present.

Referring to Block 208, in some embodiments, the sample is a sectioned tissue sample. In some such embodiments, each respective capture spot in the set of capture spots is (i) at a different position in a two-dimensional array and (ii) associates with one or more analytes from the sectioned tissue sample. In some such embodiments each respective capture spot in the set of capture spots is characterized by at least one unique spatial barcode in a plurality of spatial barcodes.

In some embodiments, referring to Block 210, the one or more analytes are nucleic acids, RNA, DNA, proteins, or carbohydrates.

In some embodiments, the one or more analytes is a plurality of analytes. For instance, referring to Block 212, in some embodiments, the one or more analytes comprise five or more analytes, ten or more analytes, fifty or more analytes, one hundred or more analytes, five hundred or more analytes, 1000 or more analytes, 2000 or more analytes, or between 2000 and 10,000 analytes. In some embodiments, the one or more analytes comprises at least 2000, at least 5000, at least 10,000, at least 100,000, at least 500,000, at least 1 million, at least 2 million, or at least 5 million analytes. In some embodiments, the one or more analytes includes no more than 10 million, no more than 5 million, no more than 1 million, no more than 100,000, no more than 10,000 or no more than 1000 analytes. In some embodiments, the one or more analytes comprises from 1000 to 10,000, from 5000 to 100,000, from 10,000 to 500,000, or from 20,000 to 5 million analytes. In some embodiments, the one or more analytes falls within another range starting no lower than 10 analytes and ending no higher than 10 million analytes.

Generally, as described above, the at least one unique spatial barcode for each respective capture spot in the set of capture spots is used to spatially resolve the location of the one or more analytes associated with the respective capture spot. See, for example, the sections entitled "Barcodes," "Capture probes," and "Methods for Spatial Analysis of Analytes," above. In some embodiments, referring to Block 214, the unique spatial barcode encodes a unique predetermined value selected from the set {1, . . . , 1024}, {1, . . . , 4096}, {1, . . . , 16384}, {1, . . . , 65536}, {1, . . . , 262144}, {1, . . . , 1048576}, {1, . . . , 4194304}, {1, . . . , 16777216}, {1, . . . , 67108864}, or {1, . . . , $1 \times 10^{12}$}.

In an example embodiment, referring to Block 216, the one or more analytes is a plurality of analytes, a respective capture spot in the set of capture spots includes a plurality of capture probes, each probe in the plurality of capture probes including a capture domain that is characterized by a capture domain type in a plurality of capture domain types, and each respective capture domain type in the plurality of capture domain types is configured to bind to a different analyte in the plurality of analytes. Thus, in some such embodiments, each capture domain type corresponds to a specific analyte (e.g., a specific oligonucleotide or binding moiety for a specific analyte). In some embodiments, each capture domain type in the plurality of capture domain types is configured to bind to the same analyte (e.g., specific binding complementarity to a single analyte) or to different analytes (e.g., specific binding complementarity to a plurality of analytes).

In some embodiments, referring to Block 220, the one or more analytes is a plurality of analytes, and a respective capture spot in the set of capture spots includes a plurality of capture probes, each capture probe in the plurality of capture probes including a capture domain that is characterized by a single capture domain type configured to bind to each analyte in the plurality of analytes in an unbiased manner. Thus, in some such embodiments, the capture domain comprises a non-specific capture moiety (e.g., an oligo-dT binding moiety).

As described above, in some embodiments, capture spots can include one or more (e.g., two or more, three or more, four or more, five or more, six or more, eight or more, ten or more, 12 or more, 15 or more, 20 or more, 30 or more, 50 or more, 100 or more, 1000 or more, or 10,000 or more) different types of capture probes attached to a single capture spot. For instance, referring to Block 218, the plurality of capture domain types comprises between 5 and 15,000 capture domain types and the respective capture spot includes at least five, at least 10, at least 100, or at least 1000 capture probes for each capture domain type in the plurality of capture domain types. In some embodiments, the respective capture spot includes at least 5000, at least 10,000, at least 50,000, at least 100,000, or at least 500,000 capture probes for each capture domain type in the plurality of capture domain types. In some embodiments, the respective capture spot includes no more than 1,000,000, no more than 100,000, no more than 10,000, no more than 1000, or no more than 100 capture probes for each capture domain type in the plurality of capture domain types. In some embodiments, the respective capture spot includes from 100 to 1000, from 1000 to 100,000, from 500 to 2000, or from 5000 to 500,000 capture probes for each capture domain type in the plurality of capture domain types. In some embodiments, the respective capture spot includes, for each capture domain type in the plurality of capture domain types, another range of capture probes that starts no lower than 5 capture probes and ending no higher than 1,000,000 capture probes.

In some embodiments, each respective capture spot in the set of capture spots is contained within a 100 micron by 100 micron square on the substrate (e.g., on the substrate of the substrate). In some embodiments, each respective capture spot in the set of capture spots is contained within a 50 micron by 50 micron square on the substrate. Referring to Block 222, in some embodiments, each respective capture spot in the set of capture spots is contained within a 10 micron by 10 micron square on the substrate. In some embodiments, each respective capture spot in the set of capture spots is contained within a 1 micron by 1 micron square, a 0.5 micron by 0.5 micron square, a 0.3 micron by 0.3 micron square, or a 0.2 micron by 0.2 micron square on the substrate.

Referring to Block 224, in some embodiments, a distance between a center of each respective capture spot to a neighboring capture spot in the set of capture spots on the substrate is between 4 microns and 8 microns. In some embodiments, a distance between a center of each respective capture spot to a neighboring capture spot in the set of capture spots on the substrate is between 300 nanometers and 300 microns, between 300 nanometers and 15 microns, between 800 nanometers and 10 microns, or between two microns and seven microns. In some embodiments, a distance between a center of each respective capture spot to a neighboring capture spot in the set of capture spots on the substrate is at least 100 nanometers, at least 500 nanometers, at least 1 micron, at least 2 microns, at least 5 microns, at least 10 microns, or at least 20 microns. In some embodiments, a distance between a center of each respective capture spot to a neighboring capture spot in the set of capture spots on the substrate is no more than 500 microns, no more than 100 microns, no more than 10 microns, or no more than 1 micron. In some embodiments, a distance between a center of each respective capture spot to a neighboring capture spot in the set of capture spots on the substrate falls within another range starting no lower than 100 nanometers and ending no higher than 500 microns.

Referring to Block 226, in some embodiments, a shape of each capture spot in the set of capture spots on the substrate is a closed-form shape. In some embodiments, the closed-form shape is circular, elliptical, or an N-gon, where N is a value between 1 and 20. In some embodiments, the closed-form shape is hexagonal. Referring to Block 228, in some such embodiments, the closed-form shape is circular and each capture spot in the set of capture spots has width of between 3 microns and 7 microns. In some embodiments, the closed-form shape is circular and each capture spot in the set of capture spots has a diameter of at least 0.03, at least 0.1, at least 0.5, at least 1, at least 2, at least 3, at least 5, at least 10, at least 20, at least 50, or at least 100 microns. In some embodiments, the closed-form shape is circular and each capture spot in the set of capture spots has a diameter of no more than 200, no more than 100, no more than 50, no more than 10, or no more than 5 microns. In some embodiments, the closed-form shape is circular and each capture spot in the set of capture spots has a diameter of between 30 nanometers and 200 microns, between 30 microns and 200 microns, or between 0.5 microns and 60 microns. In some embodiments, the closed-form shape is circular and each capture spot in the set of capture spots has a diameter that falls within another range starting no lower than 30 nanometers and ending no higher than 200 microns.

In some embodiments, the set of capture spots on the substrate are positioned as an array (e.g., a capture spot array). For example, in some embodiments, the set of capture spots in a capture spot array are arranged hexagonally or in a grid.

Referring to Block 230, in some embodiments, a capture spot in the set of capture spots comprises a capture domain. Referring to Block 232, in some embodiments, a capture spot in the set of capture spots comprises a cleavage domain. Referring to Block 234, in some embodiments, each capture spot in the set of capture spots is attached directly or attached indirectly to the substrate. See, for example, characteristics of capture spots as described in the sections entitled "Capture probes," "Capture spots," and "Capture spot arrays," above.

Referring to Block 236, in some embodiments, the set of capture spots comprises at least 10,000 capture spots, at least 100,000 capture spots, at least 500,000 capture spots, at least $1 \times 10^6$ capture spots, at least at least $2 \times 10^6$ capture spots, at least at least $3 \times 10^6$ capture spots, or at least at least $4 \times 10^6$ capture spots. For instance, in some embodiments, the set of capture spots includes at least 50, at least 100, at least 200, at least 500, at least 1000, at least 2000, at least 5000, at least 10,000, at least 100,000, at least 500,000, at least 1 million, at least 2 million, at least 3 million, or at least 4 million capture spots. In some embodiments, the set of capture spots comprises no more than 5 million, no more than 1 million, no more than 100,000, no more than 10,000, no more than 1000, or no more than 500 capture spots. In some embodiments, the set of capture spots comprises from 100 to 10,000, from 300 to 5000, from 2000 to 100,000, or from 50,000 to 500,000 capture spots. In some embodiments, the set of capture spots includes a plurality of capture spots that falls within another range starting no lower than 50 capture spots and ending no higher than 5 million capture spots.

Referring to Block 238, in some embodiments, each respective capture spot in the set of capture spots includes 1000 or more capture probes, 2000 or more capture probes, 10,000 or more capture probes, 100,000 or capture more probes, $1 \times 10^6$ or more capture probes, $2 \times 10^6$ or more capture probes, $5 \times 10^6$ capture probes, or $1 \times 10^7$ or more capture probes. In some embodiments, each respective capture spot includes no more than 50 million, no more than 5 million, no more than 1 million, no more than 100,000, no more than 10,000 or no more than 5000 capture probes. In some embodiments, each respective capture spot comprises from 1000 to 10,000, from 5000 to 100,000, from 10,000 to 500,000, or from 20,000 to 5 million capture probes. In some embodiments, each respective capture spot includes a plurality of capture probes that falls within another range starting no lower than 1000 capture probes and ending no higher than 50 million capture probes.

Referring to Block 240, in some embodiments, each capture probe in the respective capture spot includes a poly-A sequence or a poly-T sequence and a unique spatial barcode that characterizes the respective capture spot. Referring to Block 242, in some embodiments, each capture probe in the respective capture spot includes the same spatial barcode from the plurality of spatial barcodes. Referring to Block 244, in some embodiments, each capture probe in the respective capture spot includes a different spatial barcode from the plurality of spatial barcodes.

Numerous alternative embodiments for capture domain types, capture spot sizes, arrays, probes, spatial barcodes analytes, and/or other characteristics of capture spots including but not limited to dimensions, designs, and modifications are also possible, as discussed in further detail herein, as well as any substitutions, modifications, additions, deletions, and/or combinations thereof, as will be apparent to one skilled in the art.

In some embodiments, the plurality of border regions comprises at least 2, at least 3, at least 4, at least 5, at least 10, or at least 20 border regions. In some embodiments, the plurality of border regions comprises no more than 50, no more than 20, no more than 10, or no more than 5 border regions. In some embodiments, the plurality of border regions comprises from 2 to 5, from 3 to 10, or from 2 to 20 border regions. In some embodiments, the plurality of border regions falls within another range starting no lower than 2 border regions and ending no higher than 50 border regions.

Figure 5:
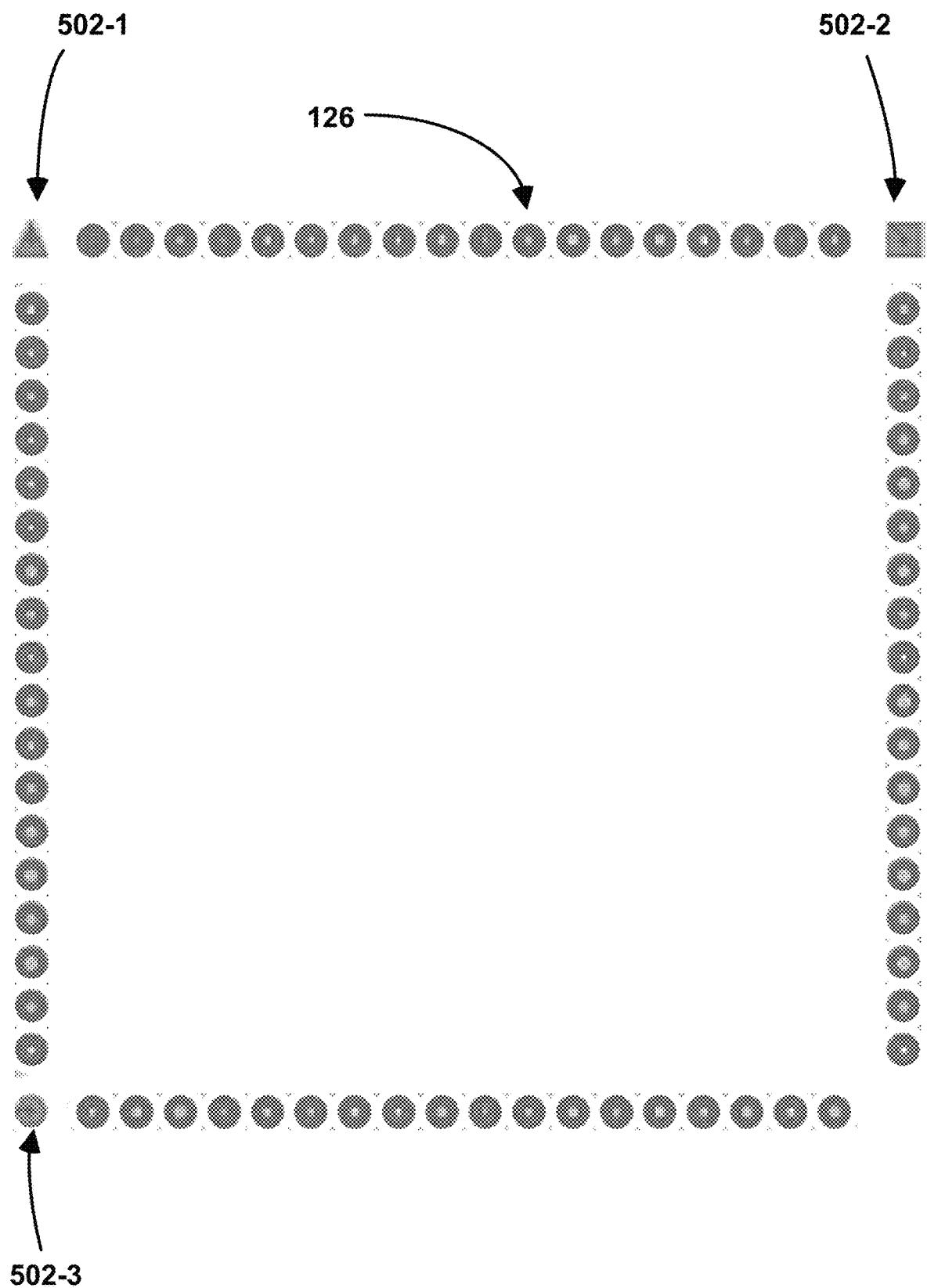
FIG. 5 illustrates a substrate that has a plurality of fiducial markers and a plurality of glyphs, in accordance with an embodiment of the present disclosure.
Figure 12:
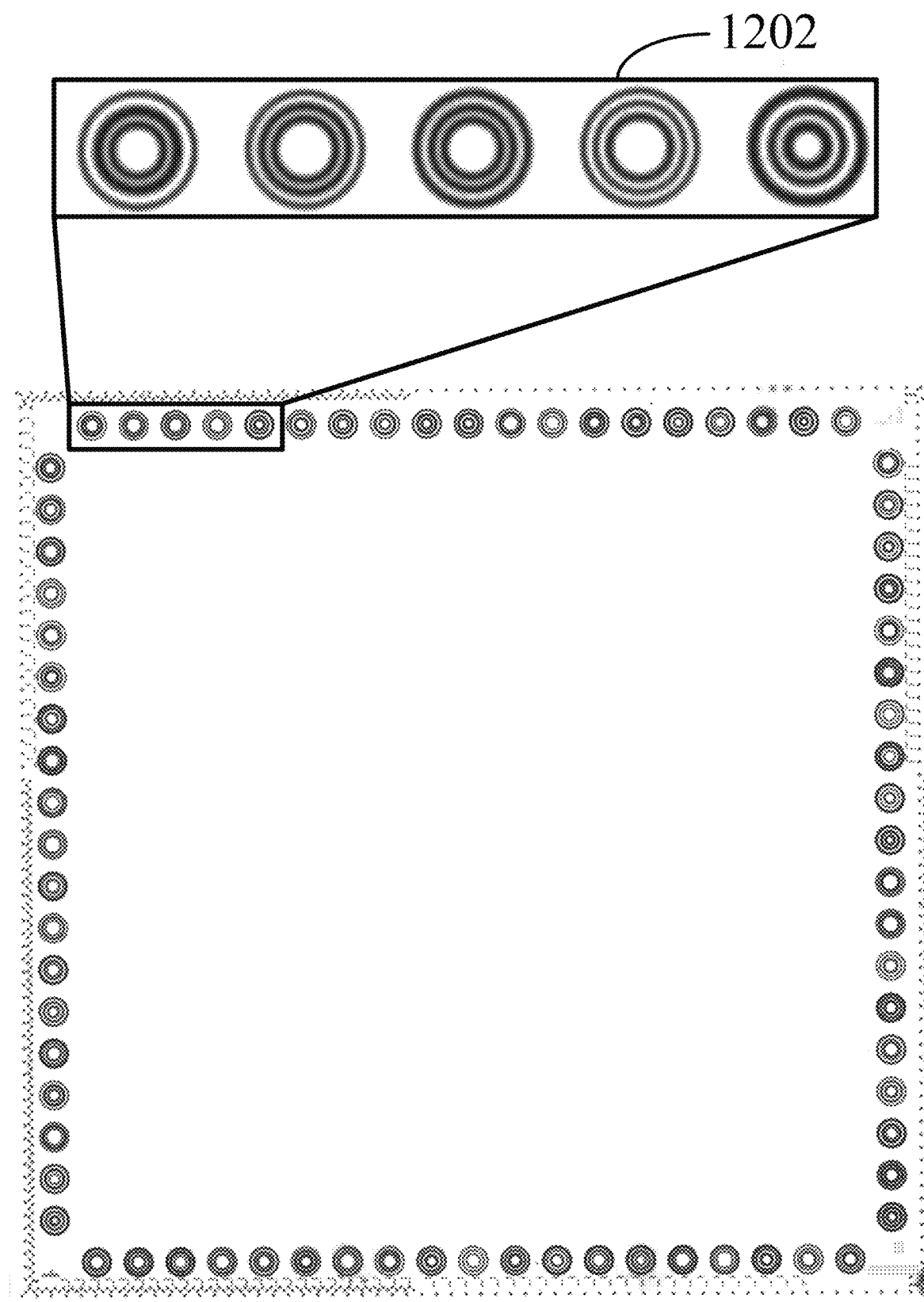
FIG. 12 illustrates a substrate that has a plurality of fiducial markers, with five of the markers expanded in an inset, in accordance with an embodiment of the present disclosure.

In some embodiments, the intersection of each respective border region in the plurality of border regions generates a frame (e.g., bordering a region of interest). For example, in some embodiments, the plurality of intersecting border regions frames a region of a substrate. In some embodiments, the plurality of intersecting border regions frames the set of capture probes on the substrate (e.g., a capture probe array). In some embodiments, the plurality of intersecting border regions creates a frame of any closed-form shape (e.g., circular, elliptical, or an N-gon, where N is a value between 1 and 20). In an example embodiment, the plurality of border regions consists of four border regions that intersect to create a square frame surrounding a capture probe array on the substrate. FIG. 5 illustrates an example of four border regions that generate a square frame, where each respective border region comprises a respective plurality of fiducial markers 126. FIG. 12 illustrates another example of four border regions that generate a square frame, where each respective border region comprises a respective plurality of fiducial markers 126. In FIG. 12, five of the fiducial markers in one border region have been expanded in inset box 1202 for visualization of the ring patterns.

Referring to Block 246, in some embodiments, the substrate comprises one or more glyphs at a first corner of the substrate.

In some embodiments, the substrate comprises one or more glyphs in a first corner and one or more glyphs in a second corner in a plurality of corners of the substrate. In some such embodiments, the one or more glyphs in the first corner are different than the one or more glyphs in the second corner.

In some embodiments, the substrate comprises a respective one or more glyphs on at least 2, at least 3, or at least 4 corners of the substrate. In some embodiments, at least one corner of the substrate does not include a glyph. In some embodiments, the glyphs at each respective corner are unique with respect to other glyphs at other corners of the substrate.

In some embodiments, a respective corner of a substrate is positioned at a corner between two intersecting edges of the substrate (e.g., a corner between two intersecting edges of a glass slide). For example, referring to Block 248, in some embodiments, the substrate is rectangular and further comprises one or more glyphs at each corner of the substrate. In some embodiments, a respective corner of a substrate is positioned at a corner between two intersecting border regions on the substrate (e.g., a corner between two intersecting border regions framing a capture probe array on a substrate, as illustrated in FIG. 5).

In some embodiments, the one or more glyphs at a respective corner of the substrate is a plurality of glyphs. In some such embodiments, the plurality of glyphs at a respective corner of the substrate comprises at least 2, at least 3, at least 4, at least 5, at least 10, or at least 15 glyphs. In some embodiments, the plurality of glyphs at a respective corner of the substrate comprises no more than 20, no more than 10, or no more than 5 glyphs. In some embodiments, the plurality of glyphs at a respective corner of the substrate comprises from 2 to 10, from 3 to 20, or from 2 to 5 glyphs. In some embodiments, the plurality of glyphs at a respective corner of the substrate falls within another range starting no lower than 2 glyphs and ending no higher than 20 glyphs.

In some implementations, a glyph comprises any distinguishing shape, icon, or symbol that can be visually represented on the substrate. In some implementations, a glyph comprises any closed-form shape (e.g., circular, elliptical, or an N-gon, where N is a value between 1 and 20) having any texture or pattern that can be visually represented on the substrate (e.g., dashes, cross-hatching, shading, fill, etc.). For instance, as illustrated in FIG. 5, in an exemplary embodiment, the substrate comprises a respective glyph at three corners positioned between intersecting border regions on the substrate, where the respective glyph at the first corner is a triangle 502-1, the respective glyph at the second corner is a square 502-2, the respective glyph at the third corner is a hexagon 502-3, and the fourth corner is empty. In some embodiments, each respective glyph at a corresponding one or more corners of the substrate is the same or a different glyph. For instance, in another exemplary embodiment, each respective glyph at each respective corner in the one or more corners of a substrate is a triangle. In some embodiments, each respective glyph at a corresponding one or more corners of the substrate has the same or a different orientation. For instance, in the exemplary embodiment above, each respective triangle in the one or more corners of the substrate is oriented in the same direction.

It will be appreciated that the substrate can contain any combination of one or more glyphs (e.g., having any shape, pattern, or fill) and/or blanks (e.g., empty corners), at any one or more corners of the substrate, as disclosed herein, or any substitutions, modifications, additions, deletions, and/or combinations thereof, as will be apparent to one skilled in the art.

In some embodiments, referring again to Block 202, the substrate further includes at least a first plurality of fiducial markers 126. Fiducial markers are described in further detail herein (see, e.g., the section entitled "Fiducials," above). Briefly, in some embodiments, fiducial markers are included on the substrate as one or more markings on the surface of the substrate. In some embodiments, fiducial markers serve as guides for correlating spatial information with the characterization of the analyte of interest.

In some embodiments, the first plurality of fiducial markers 126 comprises at least three fiducial markers. In some embodiments, the first plurality of fiducial markers comprises at least 5, at least 10, at least 15, at least 20, at least 30, at least 50, at least 60, at least 100, or at least 200 fiducial markers. In some embodiments, the first plurality of fiducial markers comprises no more than 500, no more than 200, no more than 100, or no more than 50 fiducial markers. In some embodiments, the first plurality of fiducial markers comprises from 3 to 50, from 10 to 100, from 40 to 80, or from 3 to 10 fiducial markers. In some embodiments, the first plurality of fiducial markers falls within another range starting no lower than 3 fiducial markers and ending no higher than 500 fiducial markers.

In some embodiments, the substrate further includes additional fiducial markers other than the first plurality of fiducial markers. In some such embodiments, the substrate includes at least 10, at least 20, at least 50, at least 100, at least 200, or at least 500 additional fiducial markers other than the first plurality of fiducial markers. In some embodiments, the substrate includes no more than 1000, no more than 500, no more than 100, or no more than 50 additional fiducial markers other than the first plurality of fiducial markers. In some embodiments, the substrate includes from 10 to 100, from 50 to 500, from 200 to 1000, or from 30 to 200 additional fiducial markers. In some embodiments, the substrate includes a plurality of additional fiducial markers that falls within another range starting no lower than 10 additional fiducial markers and ending no higher than 1000 additional fiducial markers. In some embodiments, any of the embodiments disclosed herein for a respective fiducial marker in the first plurality of fiducial markers is similarly contemplated for use for a respective additional fiducial marker in the plurality of additional fiducial markers.

Referring to Block 250, in some embodiments, each fiducial marker in the first plurality of fiducial markers has a width of between 0.001 microns and 25 microns. In some embodiments, a respective fiducial marker has a width (e.g., diameter) of at least 5, at least 10, at least 20, at least 50, at least 100, at least 150, at least 200, or at least 250 microns. In some embodiments, a respective fiducial marker has a width (e.g., diameter) of no more than 500, no more than 250, no more than 200, no more than 100, or no more than 50 microns. In some embodiments, a respective fiducial marker has a width (e.g., diameter) of between 10 and 100 microns, between 50 and 200 microns, between 30 and 250 microns, or between 5 and 40 microns. In some embodiments, a respective fiducial marker has a width (e.g., diameter) that falls within another range starting no lower than 5 microns and ending no higher than 500 microns.

In some embodiments, a respective fiducial marker has a width (e.g., diameter) that is sufficient to be accurately resolved by an imaging system. In some such embodiments, the width (e.g., diameter) of a respective fiducial marker in the first plurality of fiducial markers is determined based on the resolution capability of a respective imaging system used to obtain the sample image. In some embodiments, a respective fiducial marker has a width (e.g., diameter) that is sufficient to be visible to the naked eye.

Referring to Block 252, in some embodiments, the first plurality of fiducial markers is made out of titanium, chromium, platinum, tantalum, gold, silver, a combination thereof, and/or an alloy thereof. In some embodiments, a respective fiducial marker in the first plurality of fiducial markers comprises a fluorescent moiety. In some embodiments, a respective fiducial marker in the first plurality of fiducial markers is made of any suitable high contrast material, as will be apparent to one skilled in the art.

In some embodiments, fiducial markers are prepared on the substrate using any one of the following non-limiting techniques: chrome-deposition on glass, gold nanoparticles, laser-etching, tubewriter-ink, microspheres, Epson 802, HP 65 Black XL, permanent marker, fluorescent oligos, amine iron oxide nanoparticles, amine thulium doped upconversion nanophosphors, and/or amine Cd-based quantum dots. In some embodiments, techniques for fiducial marker preparation include photolithography, sand-blasting, etching, printing, depositing, or physical modification of the substrate surface.

In some embodiments, a respective fiducial marker is printed onto a substrate surface to a respective thickness (e.g., printing depth). For instance, referring to Block 254, in some embodiments, the first plurality of fiducial markers have a thickness of between 10 nm and 50 nm. Referring to Block 256, in some embodiments, the first plurality of fiducial markers have a thickness of between 40 nm and 300 nm. In some embodiments, a respective fiducial marker in the first plurality of fiducial markers has a thickness of at least 5, at least 10, at least 20, at least 30, at least 40, at least 50, at least 100, at least 200, or at least 300 nm. In some embodiments, a respective fiducial marker in the first plurality of fiducial markers has a thickness of no more than 500, no more than 300, no more than 100, no more than 50, or no more than 20 nm. In some embodiments, a respective fiducial marker in the first plurality of fiducial markers has a thickness of from 5 to 100, from 20 to 60, from 50 to 200, or from 100 to 400 nm. In some embodiments, a respective fiducial marker in the first plurality of fiducial markers has a thickness that falls within another range starting no lower than 5 nm and ending no higher than 500 nm.

In some embodiments, the fiducial markers are non-transiently attached to the outer boundary of the substrate (e.g., the outer boundary of a respective capture area on the substrate) and the sample is overlayed within the boundary of the fiducial markers. In some embodiments, the fiducial markers are transiently attached to the outer boundary of the substrate (e.g., by attachment of an adaptor, a slide holder, and/or a cover slip). In some embodiments, the fiducial markers are transiently attached to the outer boundary of the substrate before or after the sample is on the substrate. In some embodiments, the fiducial markers are transiently or non-transiently attached to the substrate after the sample is on but prior to obtaining the image.

In some embodiments, one or more fiducial markers in the first plurality of fiducial markers are present on at least 3, at least 4, at least 5, or at least 10 border regions in the plurality of border regions on the substrate. In some embodiments, all or a subset of the plurality of border regions on the substrate comprises a respective fiducial marker in the first plurality of fiducial markers, including any number of border regions as described above.

In some embodiments, the first plurality of fiducial markers is positioned such that they surround (e.g., frame) the set of capture spots on the substrate (e.g., a capture spot array). Accordingly, in some embodiments, the first plurality of fiducial markers is arranged along an external border of the substrate and/or the set of capture spots, such that they surround (e.g., frame) the set of capture spots and/or all or a portion of the sample.

In some embodiments, the method comprises using at least the first plurality of fiducial markers to visually position the sample on the substrate (e.g., positioned within an area bordered by the first plurality of fiducial markers). In some such embodiments, each respective fiducial marker in the first plurality of fiducial markers has a width (e.g., diameter) that is discernible by the human eye. In some embodiments, visual positioning of the sample on the substrate is assisted by an imaging apparatus, such as a microscope and/or a camera.

In some embodiments, the first plurality of fiducial markers comprises a plurality of subsets of fiducial markers. In some embodiments, the plurality of subsets of fiducial markers includes at least 2, at least 3, at least 4, at least 5, at least 10, or at least 20 subsets of fiducial markers. In some embodiments, the plurality of subsets of fiducial markers comprises no more than 50, no more than 20, no more than 10, or no more than 5 subsets of fiducial markers. In some embodiments, the plurality of subsets of fiducial markers comprises from 2 to 5, from 3 to 10, or from 2 to 20 subsets of fiducial markers. In some embodiments, the plurality of subsets of fiducial markers falls within another range starting no lower than 2 subsets of fiducial markers and ending no higher than 50 subsets of fiducial markers. In some embodiments, each subset of fiducial markers comprises a unique set of fiducial markers. In some embodiments, each fiducial marker in the first plurality of fiducial markers is exclusive to a single subset of fiducial markers, such that no fiducial marker is common to any two subsets of fiducial markers in the plurality of subsets of fiducial markers. In some embodiments, each respective fiducial marker in a respective subset of fiducial markers is unique (e.g., each respective fiducial marker is represented only once in the respective subset of fiducial markers).

In some embodiments, each respective border region in the plurality of border regions includes a respective subset of fiducial markers in the plurality of subsets of fiducial markers. Accordingly, in some embodiments, the plurality of subsets of fiducial markers comprises at least as many subsets of fiducial markers as border regions in the plurality of border regions.

For instance, in an exemplary embodiment, referring to Block 258, the plurality of border regions consists of four border regions, the first plurality of fiducial markers comprises a plurality of subsets of fiducial markers, and each respective border region in the plurality of border regions is associated with a respective subset of fiducial markers in the plurality of subsets of fiducial markers. In some embodiments, each respective fiducial marker in the first plurality of fiducial markers has a different pattern in a plurality of patterns (e.g., where the plurality of patterns consists of between 20 and 1000 patterns), and each pattern in the plurality of patterns encodes a different N-digit code in the plurality of N-digit codes.

In some embodiments, the plurality of patterns comprises at least 3, at least 4, at least 5, at least 10, at least 15, at least 20, at least 30, at least 50, at least 60, at least 100, or at least 200 patterns. In some embodiments, the plurality of patterns comprises no more than 500, no more than 200, no more than 100, or no more than 50 patterns. In some embodiments, the plurality of patterns comprises from 3 to 50, from 10 to 100, from 40 to 80, or from 3 to 10 patterns. In some embodiments, the plurality of patterns falls within another range starting no lower than 3 patterns and ending no higher than 500 patterns. In some embodiments, each respective fiducial marker in the first plurality of fiducial markers corresponds to a unique pattern in the plurality of patterns, and the plurality of patterns comprises at least as many unique patterns as fiducial markers in the first plurality of fiducial markers. Accordingly, in some embodiments, the plurality of N-digit codes comprises at least as many N-digit codes as the number of patterns in the plurality of patterns. In some embodiments, the number of N-digit codes in the plurality of N-digit codes is more or less than the number of patterns in the plurality of patterns.

Figure 3:
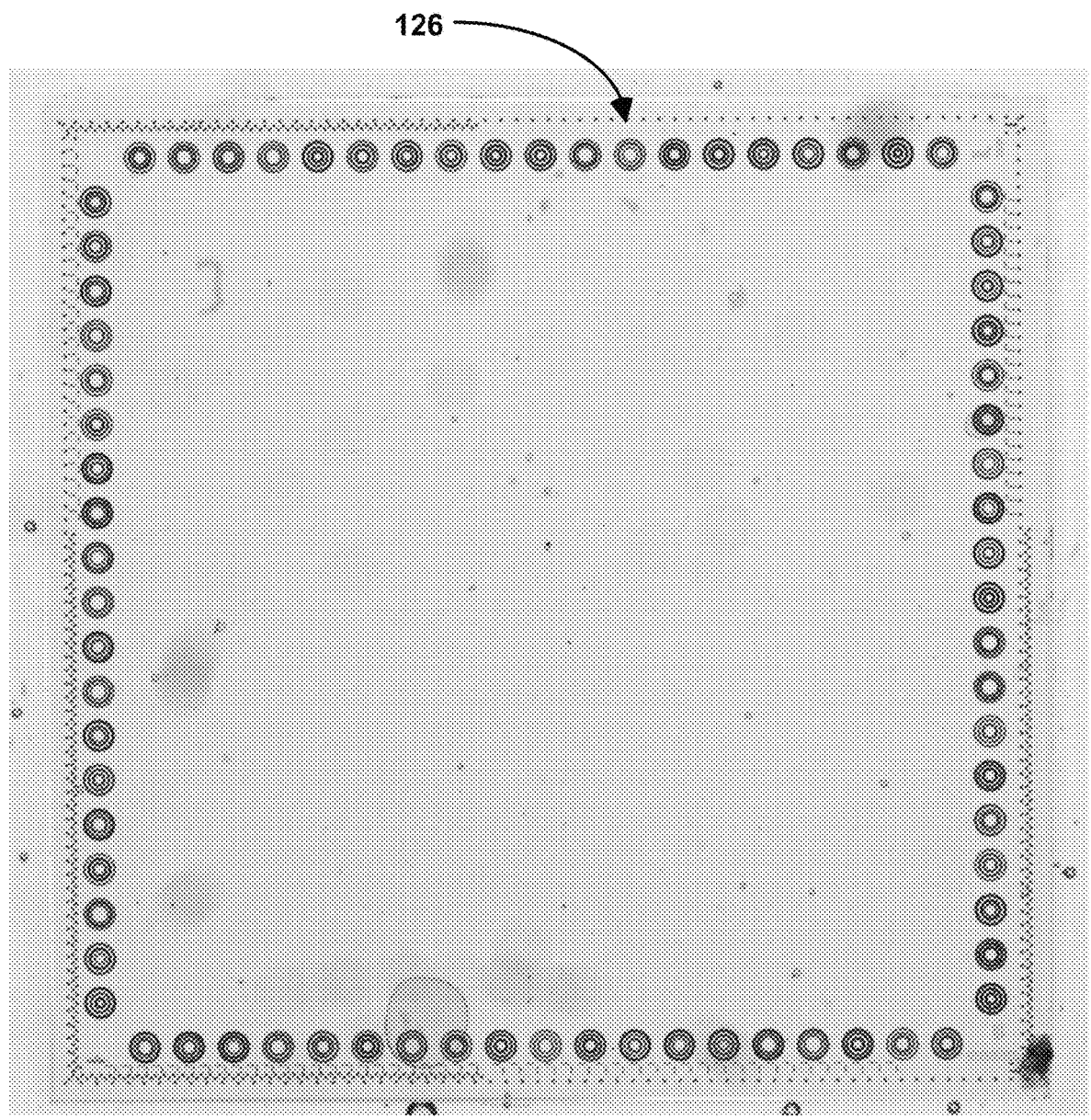
FIG. 3 illustrates a substrate that has a plurality of fiducial markers, in accordance with an embodiment of the present disclosure.

Thus, in an example embodiment, the plurality of border regions consists of four border regions, each respective border region in the plurality of border regions comprising a respective unique subset of fiducial markers in a plurality of subsets of fiducial markers in the first plurality of fiducial markers, where each respective subset of fiducial markers consists of 19 unique fiducial markers each having a different pattern in a plurality of patterns. Accordingly, the substrate comprises 76 unique fiducial markers, each fiducial marker encoding a different N-digit code. FIG. 3 illustrates an example substrate on which unique fiducial markers 126 are positioned along four border regions arranged in a square frame. As described above, in some embodiments, the unique patterns of fiducial markers allow for the accurate alignment of sample images to analyte data even in instances where only three fiducial markers are visible on the substrate and where the fiducial markers are present on at least two different border regions. Advantageously, the use of unique fiducial marker patterns that can be identified by unique N-digit codes allows each respective fiducial marker to be individually localized on the substrate without the uncertainty that arises from the positioning of a respective fiducial marker pattern at two or more locations on the substrate.

In some embodiments, each respective pattern in the plurality of patterns comprises any closed-form shape (e.g., circular, elliptical, or an N-gon, where N is a value between 1 and 20) or any open-form shape (e.g., one or more lines or curves). In some embodiments, each respective pattern in the plurality of patterns has any texture or pattern that can be visually represented on the substrate (e.g., dashes, cross-hatching, shading, fill, etc.). In some embodiments, each respective pattern in the plurality of patterns has one or more linewidths and/or spacing widths corresponding to a respective shape, texture, and/or pattern.

Referring to Block 260, in some embodiments, each respective pattern in the plurality of patterns is a different concentric closed-form arrangement. Referring to Block 262, in some embodiments, each different concentric closed-form arrangement is a different concentric circular pattern. In some such embodiments, a respective concentric closed-form arrangement includes a plurality of concentric rings.

In some such implementations, the plurality of concentric rings includes at least 2, at least 3, at least 4, at least 5, at least 6, at least 7, at least 8, at least 9, at least 10, at least 15, or at least 20 concentric rings. In some implementations, the plurality of concentric rings includes no more than 40, no more than 20, no more than 10, or no more than 5 concentric rings. In some implementations, the plurality of concentric rings includes from 2 to 10, from 2 to 5, from 3 to 8, or from 5 to 15 concentric rings. In some implementations, the plurality of concentric rings falls within another range starting no lower than 2 rings and ending no higher than 40 rings.

In some embodiments, each respective pattern in the plurality of patterns comprises a plurality of concentric rings, and the respective pattern further comprises a respective inter-ring spacing between every two consecutive rings in the plurality of concentric rings.

In some embodiments, each respective ring of a plurality of concentric rings is characterized by a respective linewidth. In some embodiments, each respective inter-ring spacing between two consecutive rings in a plurality of concentric rings is characterized by a respective inter-ring spacing width. In some such implementations, a respective linewidth and/or a respective inter-ring spacing width is at least 5, at least 10, at least 20, at least 30, or at least 50 microns. In some embodiments, a respective linewidth and/or a respective inter-ring spacing width is no more than 100, no more than 50, no more than 20, or no more than 10 microns. In some embodiments, a respective linewidth and/or a respective inter-ring spacing width is between 5 and 10 microns, between 30 and 100 microns, between 3 and 25 microns, or between 10 and 40 microns. In some embodiments, a respective linewidth and/or a respective inter-ring spacing width falls within another range starting no lower than 5 microns and ending no higher than 100 microns. In some such implementations, a respective linewidth and/or a respective inter-ring spacing width is characterized as thin, medium, or thick.

Thus, for example, referring to Block 264, in some embodiments, each respective pattern in the plurality of patterns comprises a different pattern of at least three rings and at least two inter-ring spacings, each ring of each respective pattern in the plurality of patterns is characterized by a respective linewidth in a set of at least three discrete linewidths, each of the at least two inter-ring spacings of each respective pattern in the plurality of patterns is characterized by one of at least three different inter-ring spacing widths, and a respective linewidth of each respective ring in the at least three rings of a respective pattern in the plurality of patterns together with a respective inter-ring spacing of each of the at least two inter-ring spacings of the respective pattern collectively encode at least a five bit ternary code that localizes the corresponding fiducial marker to a particular position on the substrate in accordance with the first template.

In an illustrative example, a respective pattern comprises three rings and two inter-ring spacings, where each ring is characterized by a respective linewidth and each inter-ring spacing is characterized by a respective inter-ring spacing width. A respective linewidth and/or a respective inter-ring spacing width can be selected from thin (e.g., 0), medium (e.g., 1), and thick (e.g., 2) widths. Thus, in the illustrative example, the N-digit code is a five bit ternary code indicating the sequence of selected widths for each of the three rings and the two inter-ring spacings (e.g., 0-1-1-0-2 or 2-2-2-2-2). While the foregoing example uses three rings and two inter-ring spacings, a respective fiducial marker can include any number N of rings and corresponding inter-ring spacings, each of which can be characterized by any corresponding number of possible corresponding widths. The rings and inter-ring spacings can have the same or a different set of possible corresponding widths, the selection of which can be encoded in the N-digit code.

In some embodiments, encodings are determined for a respective linewidth and/or a respective inter-ring spacing width in pixels, micrometers, or any other unit of distance (e.g., for three concentric rings having linewidths and inter-ring spacing widths of 10 μm, 15 μm, and 20 μm, an encoding can generate an N-digit code of 10-10-10-15-20). Other methods for encoding and/or identifying unique patterns for fiducial markers are possible, as will be apparent to one skilled in the art.

Accordingly, in some embodiments, the value for N is determined by the number of concentric circles and intervening spaces. For instance, for a plurality of three rings and two intervening spaces, N is 5, and for a plurality of five rings and four intervening spaces, N is 9.

Figure 10:
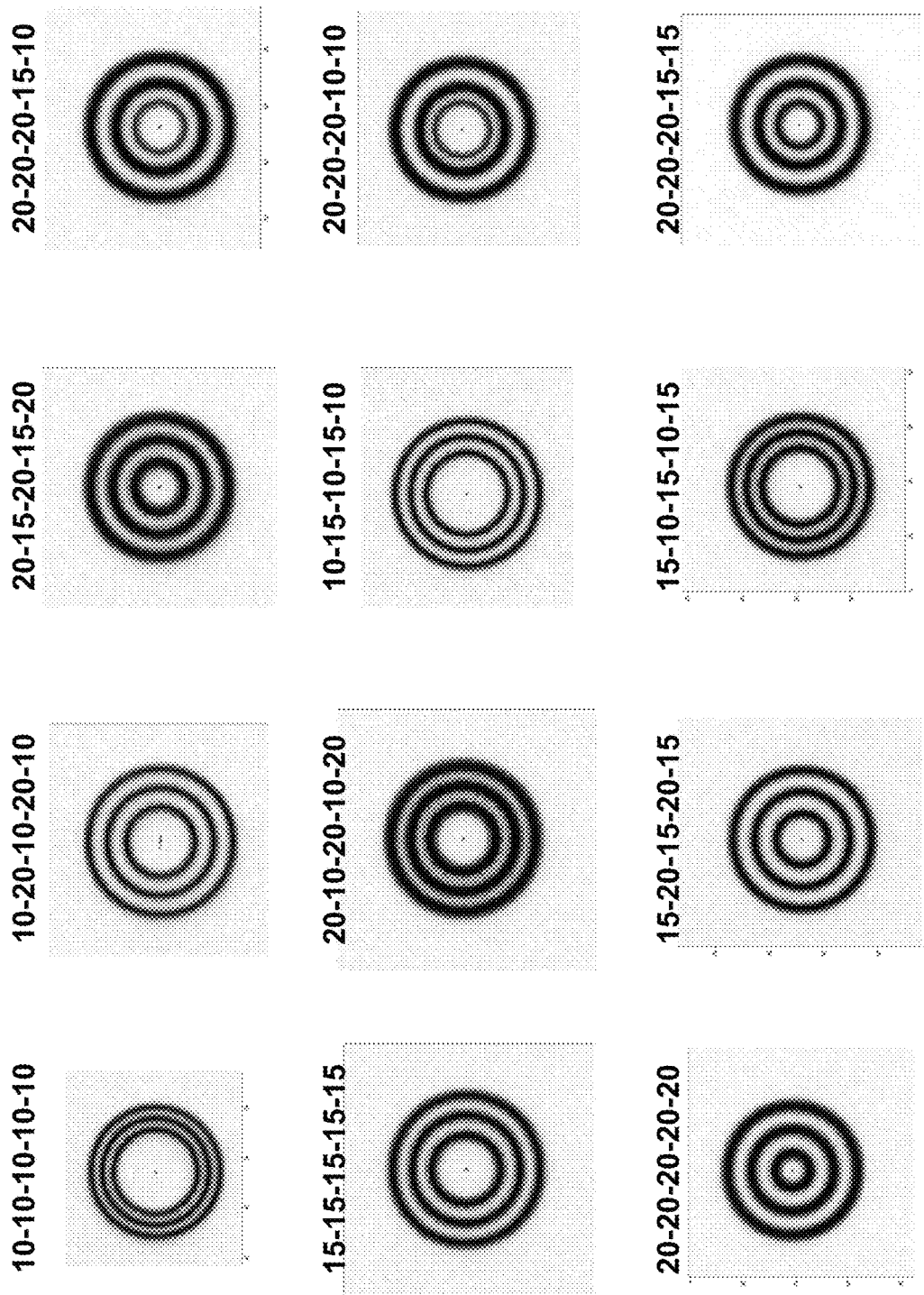
FIG. 10 illustrates example fiducial markers with corresponding N-digit codes, in accordance with an embodiment of the present disclosure.

In some embodiments, a respective N-digit code is generated in any order relative to the linewidths and/or inter-ring spacing widths of a respective fiducial marker (e.g., innermost ring to outermost ring and/or outermost ring to innermost ring). Examples of unique patterns for fiducial markers, characterized by different linewidths and inter-ring spacing widths are shown in FIG. 10.

In some embodiments, a respective ring in a respective fiducial marker has a minimum diameter. In some such embodiments, an innermost ring in a respective fiducial marker has a minimum diameter (e.g., a minimum diameter of 10 μm). In some embodiments, defining a minimum diameter for an innermost ring allows for the identification and subsequent grouping of only those edges extending from a center to an outer perimeter of a fiducial marker (e.g., thus avoiding grouping edges from opposite sides of the same fiducial marker). Accordingly, in some such embodiments, a minimum diameter provides for a sufficient distance between opposing sides of a respective fiducial marker such that edges corresponding to opposite sides of concentric rings within the same fiducial marker are not grouped together. Identification and grouping of edges are described in more detail below. In some embodiments, the minimum diameter for a respective innermost ring of a respective fiducial marker is at least a maximum linewidth and/or a maximum inter-ring spacing width apart. In some embodiments, the minimum diameter for a respective innermost ring of a respective fiducial marker is at least 1, at least 5, at least 10, at least 20, or at least 30 microns. In some embodiments, the minimum diameter is no more than 50, no more than 30, no more than 20, or no more than 10 microns. In some embodiments, the minimum diameter is between 5 and 10 microns, between 30 and 50 microns, between 3 and 25 microns, or between 10 and 40 microns. In some embodiments, the minimum diameter falls within another range starting no lower than 1 micron and ending no higher than 50 microns.

In some embodiments, a respective ring in a respective fiducial marker has a maximum diameter. In some embodiments, an innermost ring in a respective fiducial marker has a maximum diameter (e.g., a maximum diameter of 20 µm). In some embodiments, defining a maximum diameter for an innermost ring allows for the assignment of edges corresponding to a respective fiducial marker to the correct fiducial marker, rather than to a neighboring fiducial marker. Accordingly, in some such embodiments, a maximum diameter for an innermost ring tethers the plurality of edges corresponding to a respective fiducial marker to within a sufficient distance from the center of the fiducial marker such that the plurality of edges can be appropriately assigned. Identification and grouping of edges are described in more detail below. In some embodiments, the maximum diameter for a respective innermost ring of a respective fiducial marker is no more than a minimum distance between two neighboring fiducial markers in the first plurality of fiducial markers. In some embodiments, the maximum diameter for a respective innermost ring of a respective fiducial marker is at least 5, at least 10, at least 20, at least 30, or at least 50 microns. In some embodiments, the maximum diameter is no more than 100, no more than 50, no more than 20, or no more than 10 microns. In some embodiments, the maximum diameter is between 5 and 10 microns, between 30 and 100 microns, between 3 and 25 microns, or between 10 and 40 microns. In some embodiments, the maximum diameter falls within another range starting no lower than 5 microns and ending no higher than 100 microns.

In some embodiments, a distance between two or more fiducial markers includes at least a minimum separation distance. In some embodiments, defining a minimum separation distance for two or more fiducial markers allows for the segregation of edges corresponding to neighboring fiducial markers. Accordingly, in some such embodiments, a minimum separation distance provides for a sufficient distance between neighboring fiducial markers such that edges corresponding to two different fiducial markers are not grouped together. Identification and grouping of edges are described in more detail below. In some embodiments, a minimum separation distance between two neighboring fiducial markers in the first plurality of fiducial markers is at least a width (e.g., diameter) of each respective fiducial marker in the first plurality of fiducial markers. In some embodiments, a minimum separation distance between two neighboring fiducial markers in the first plurality of fiducial markers is at least a maximum linewidth and/or a maximum inter-ring spacing width for each respective fiducial marker in the first plurality of fiducial markers. In some embodiments, a minimum separation distance between two neighboring fiducial markers in the first plurality of fiducial markers is at least a maximum diameter for each respective innermost ring for each respective fiducial marker in the first plurality of fiducial markers.

In some embodiments, the minimum separation distance is at least 5, at least 10, at least 20, at least 30, or at least 50 microns. In some embodiments, the minimum separation distance is no more than 100, no more than 50, no more than 20, or no more than 10 microns. In some embodiments, the minimum separation distance is between 5 and 10 microns, between 30 and 100 microns, between 3 and 25 microns, or between 10 and 40 microns. In some embodiments, the minimum separation distance falls within another range starting no lower than 5 microns and ending no higher than 100 microns.

Referring to Block 266, the method further includes analyzing the plurality of pixel values 124 to identify a respective location 128 of each fiducial marker 126 in the first plurality of fiducial markers within the image 122.

For example, referring to Block 268, in some embodiments, the analyzing the plurality of pixel values 124 to identify a respective location 128 of each fiducial marker 126 in the first plurality of fiducial markers within the image 122 comprises: identifying a first plurality of edges 404 in the plurality of pixel values; filtering the first plurality of edges to identify a second plurality of edges from the first plurality of edges, where each edge in the second plurality of edges is a member of an edge-group 406 of length six in a plurality of edge-groups of length six in the second plurality of edges; identifying a respective fiducial center candidate using a circle Hough transform of each respective edge-group of length six in the plurality of edge-groups of length six, thereby identifying a plurality of fiducial center candidates, where each respective fiducial center candidate in the plurality of fiducial center candidates is associated with a pixel in the array of pixels; identifying a plurality of fiducial centers 410 from the plurality of fiducial center candidates by applying a threshold requirement to each fiducial center candidate in the plurality of fiducial center candidates; associating each respective edge-group 406 of length six in the plurality of edge-groups of length six with a corresponding fiducial center 410 in the plurality of fiducial centers based at least on a proximity of the respective edge-group of length six to the corresponding fiducial center; arranging, for each respective edge-group 406 of length six in the plurality of edge-groups of length six, each edge 404 in the respective edge-group of length six with respect to the fiducial center 410 associated with the respective edge-group to form a corresponding ordered set of edges for each fiducial marker in the first plurality of fiducial markers, thereby forming a respective ordered set of concentric circles 412 about each respective fiducial center in the plurality of fiducial centers; and determining, for each respective fiducial marker in the plurality of fiducial markers, at least a five bit ternary code of the fiducial marker from a radius of each concentric circle in the respective ordered set of concentric circles about the fiducial center of the respective fiducial marker. FIGS. 4A-K illustrate.

Figure 4A:
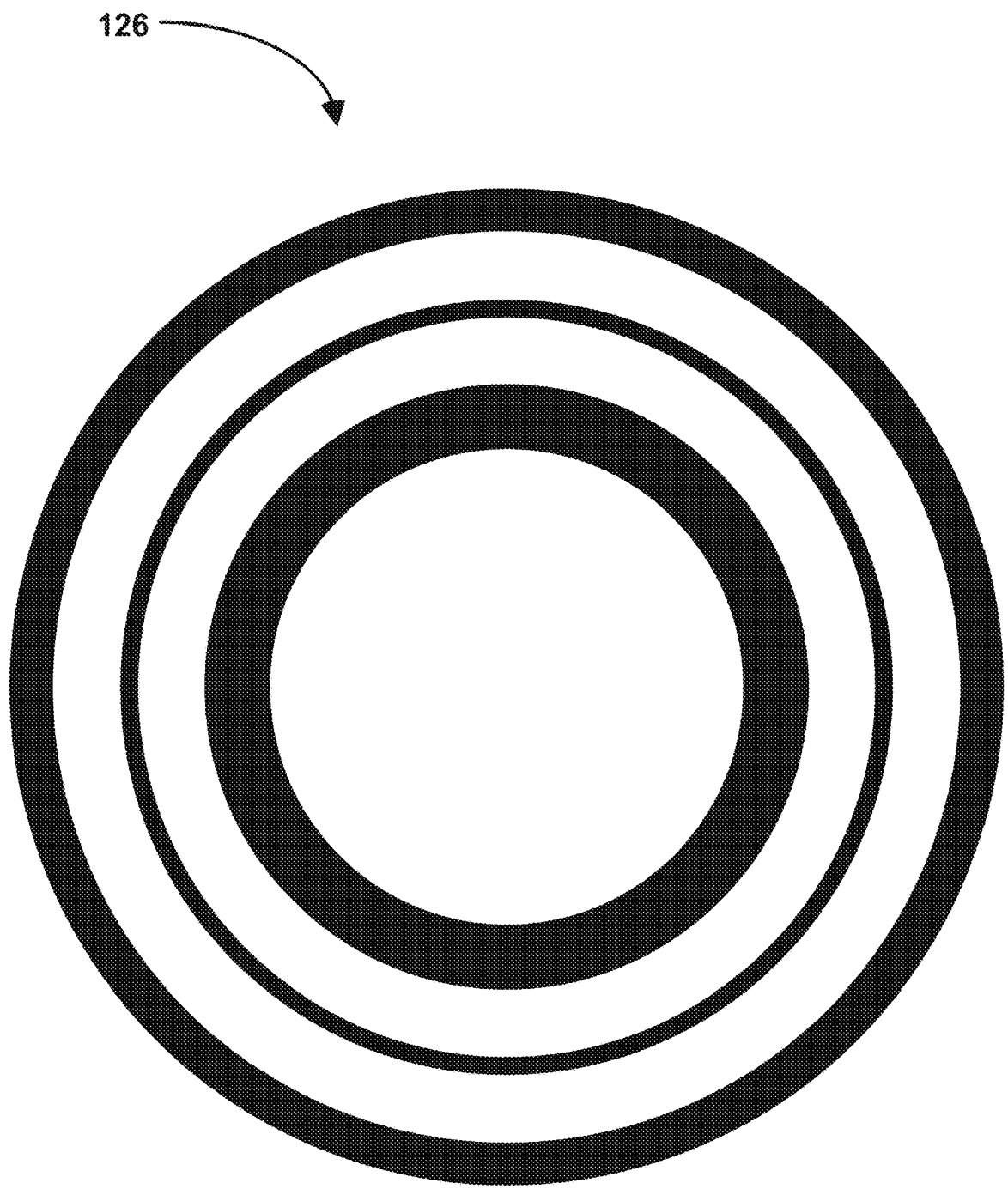
Figure 4B:
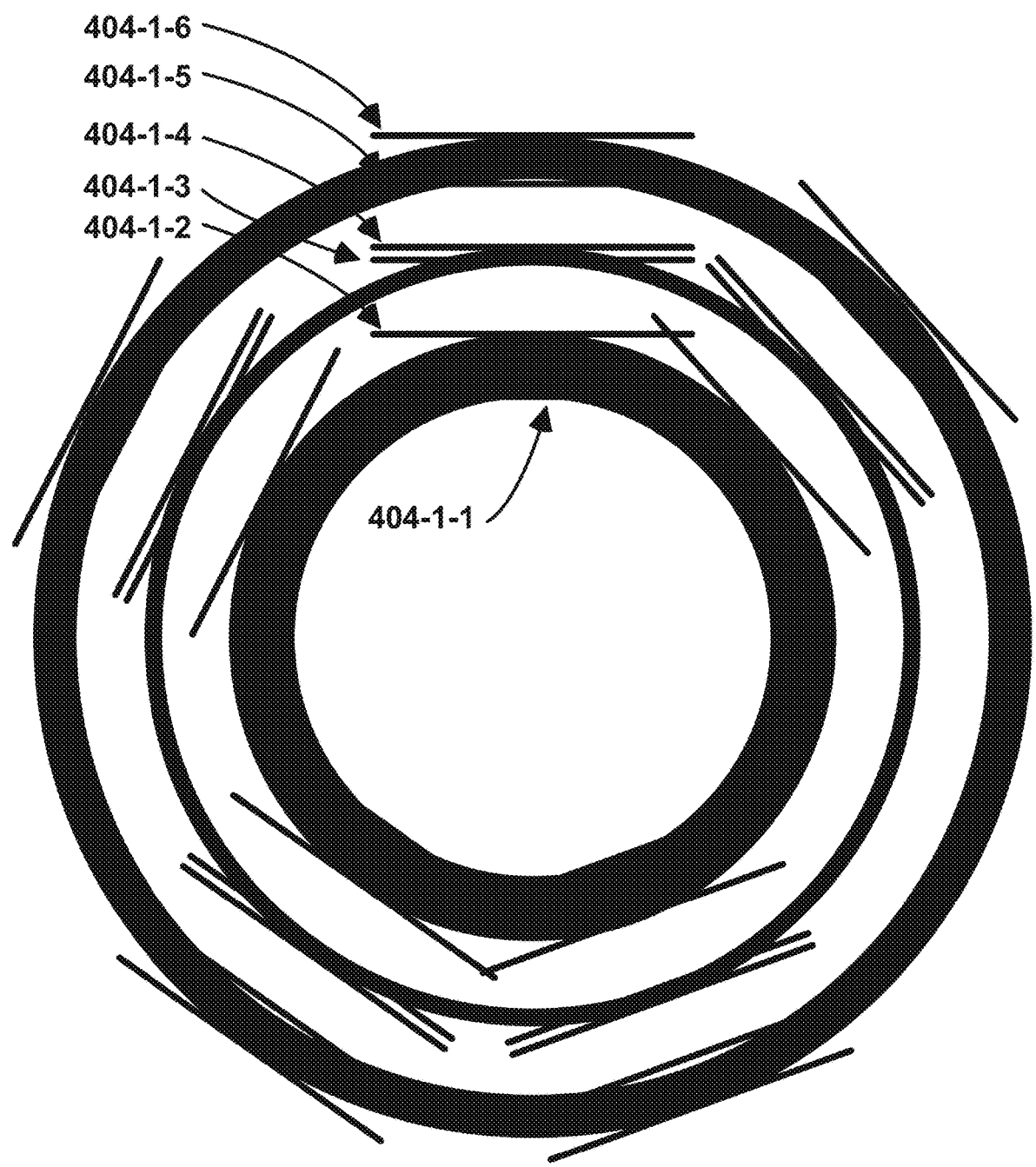

FIG. 4A illustrates a respective fiducial marker 126. In some such embodiments, the analyzing the plurality of pixel values to identify a respective location 128 of the respective fiducial marker 126 includes identifying a first plurality of edges 404 in the plurality of pixel values for the respective fiducial marker. The first plurality of edges can include both inner and outer edges of concentric rings in a concentric circular pattern, as illustrated in FIG. 4B. In addition, the first plurality of edges can include additional edges that are not specific to any fiducial markers, such as noise, sample edges, and/or other markings on the substrate.

Figure 4C:
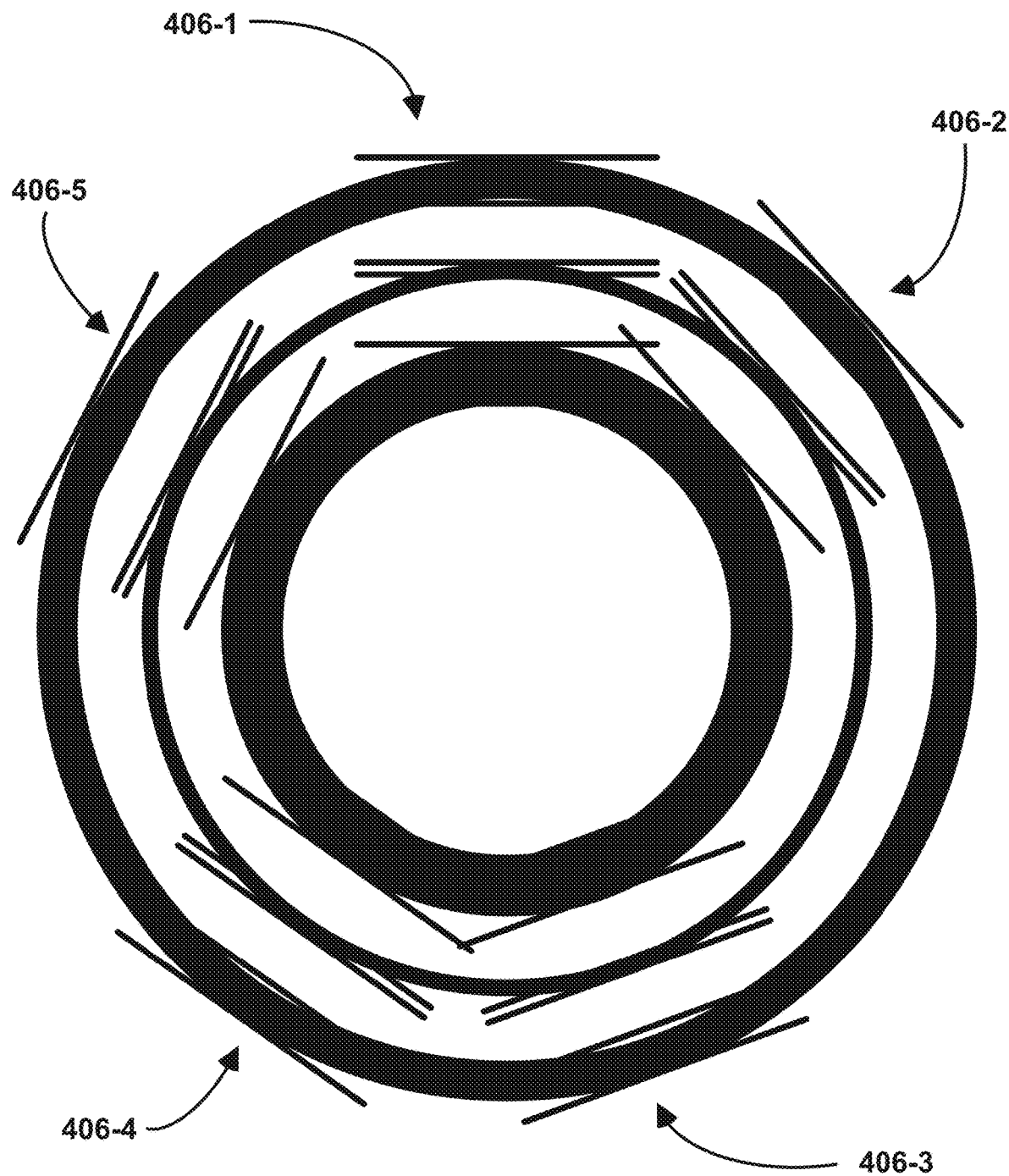
Figure 4D:
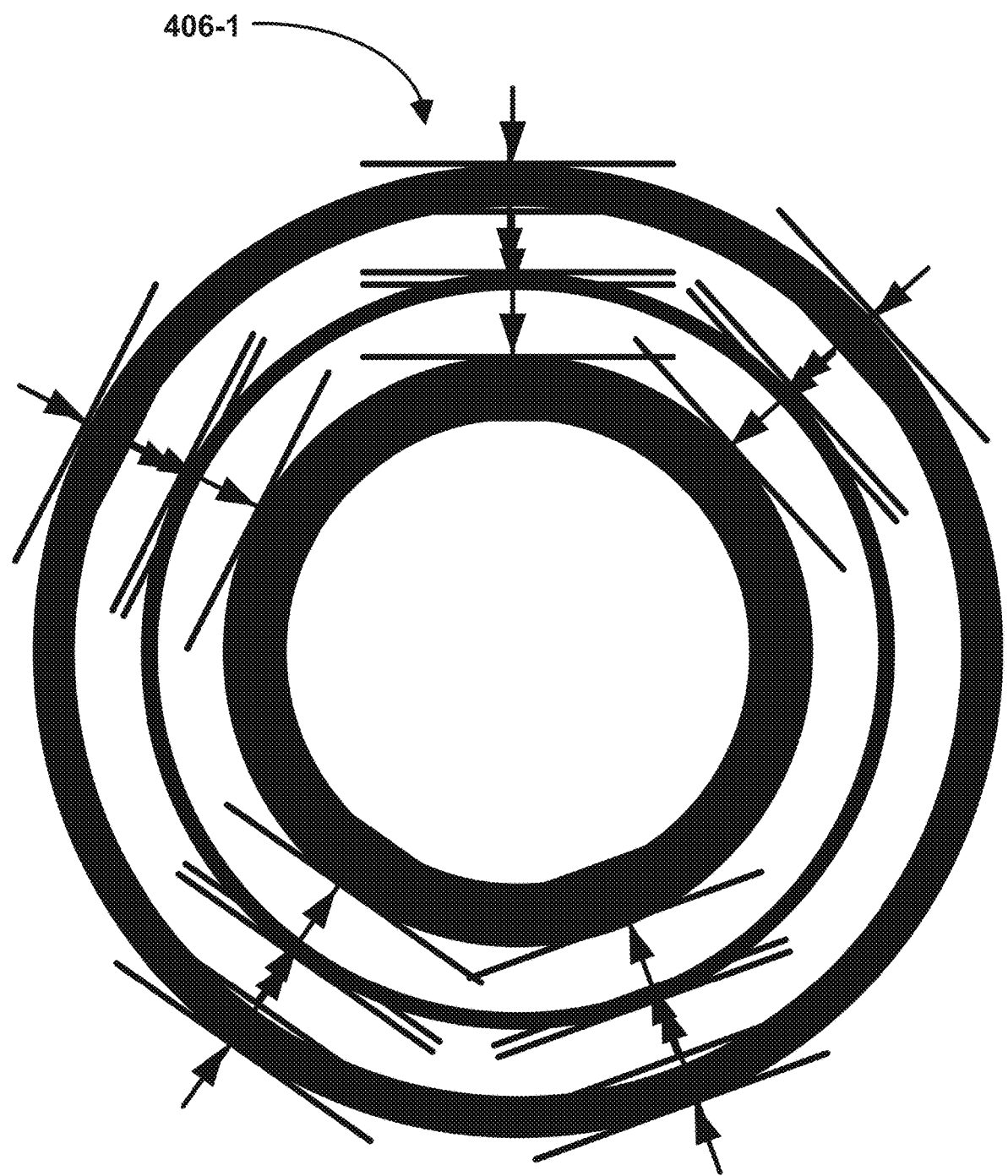
Figure 4E:
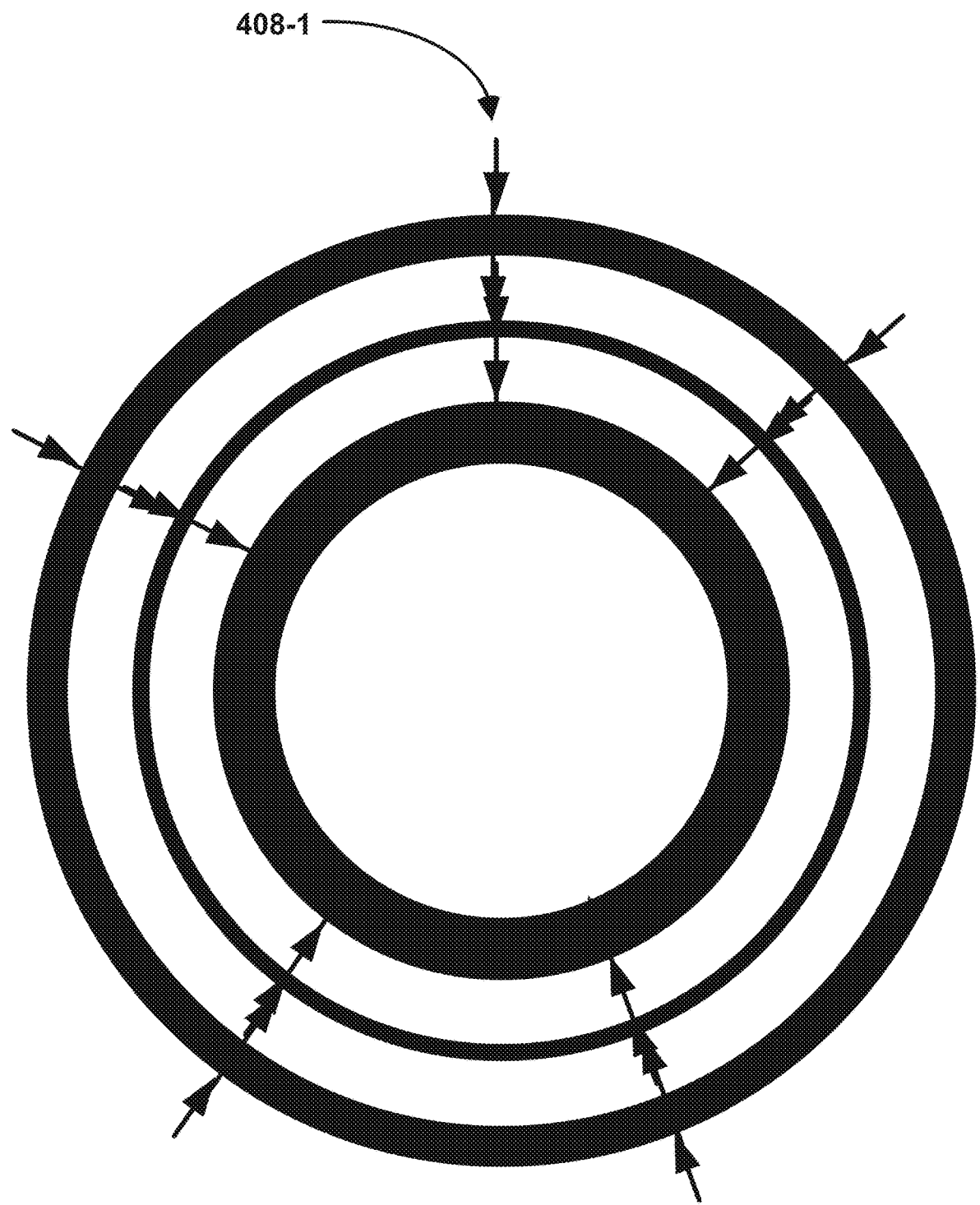

In some embodiments, the identifying the first plurality of edges includes identifying, for each respective edge in the first plurality of edges, a corresponding subpixel edge position and a corresponding normal direction (e.g., indicated by the arrows in FIG. 4D). In some embodiments, the corresponding subpixel edge position and the corresponding normal direction is identified using a subpixel edge detection algorithm. In some embodiments, the identifying the first plurality of edges in the array of pixel values is performed using Sobel edge detection.

In some embodiments, the method further includes constructing a plurality of edge-groups 406 of length M, based on the normal direction of each identified edge position. For instance, as illustrated in FIG. 4C, a plurality of edge-groups 406 of length six can be constructed from the first plurality of edges (e.g., 406-1, 406-2, 406-3, 406-4, and 406-5). The normal direction of each identified edge position in example edge-group 406-1 is indicated by the arrows in FIG. 4D.

Accordingly, an edge-group of length M is defined as a set of M edges in which a corresponding normal of a tangent of one of the edges in the edge-group intersects the remaining edges in the edge-group, and where the normal direction of each identified edge position in a respective edge-group can be visualized together as a perpendicular line (e.g., 408-1 in FIG. 4E) passing through all of the edges in the respective edge-group (e.g., 406-1). In some embodiments, M is a positive integer. In some embodiments, M is 4, 5, 6, 7, 8, 9, 10, 11, 12, 13, 14, 15, 16, 17, 18, 19, or 20. Moreover, in some such embodiments, the combined normal corresponding to all of the edges in the respective edge-group has a length that is less than a minimum innermost ring width, such that the respective edge-group does not include edges corresponding to opposing sides of the respective fiducial marker. In some embodiments, the corresponding combined normal corresponding to all of the edges in the respective edge-group has a length that is less than a minimum width of the fiducial marker. In some embodiments, the combined normal corresponding to all of the edges in the respective edge-group has a length that is less than a minimum separation distance between two neighboring fiducial markers in the first plurality of fiducial markers, such that the respective edge-group does not include edges corresponding to more than one fiducial markers.

In some implementations, the number of edges M used to construct each edge-group is based on the number of expected edges in a respective fiducial marker; for instance, a fiducial marker comprising three concentric rings defines an edge-group of length six, and a fiducial marker comprising five concentric rings defines an edge-group of length 10.

In some embodiments, the method further includes, for each respective first edge-group in a plurality of edge-groups of length M, identifying a parallel second edge-group of length M, where the parallel second edge-group has the opposite normal direction from the respective edge-group. In some such embodiments, a first edge-group and a parallel second edge-group corresponds to opposing sides of a respective fiducial marker.

In some implementations, referring again to Block 268, the method further includes filtering the first plurality of edges to identify a second plurality of edges from the first plurality of edges, where each edge in the second plurality of edges is a member of an edge-group 406 of length M (e.g., length six) in a plurality of edge-groups of length M (e.g., length six) in the second plurality of edges. Thus, in some such embodiments, the filtering the first plurality of edges is performed by excluding any edge in the first plurality of edges that does not correspond to an edge-group of length M. In some embodiments, the filtering the first plurality of edges is performed by excluding any edge-group, from the plurality of edge-groups, having a length that is shorter or longer than M.

In some embodiments, the filtering the first plurality of edges includes (i) for each respective edge in the first plurality of edges, determining a count of the number of edge-groups of length M of which the respective edge is a member, and (ii) removing, from the plurality of edge-groups, any edge-group that does not contain at least an edge that satisfies a threshold count. In some embodiments, the threshold count is 2 or more, 3 or more, 4 or more, or 5 or more. Thus, in some implementations, the filtering the first plurality of edges removes any edge-link that does not contain edges that are included in multiple edge-groups (e.g., having a count of 2 or greater).

In some embodiments, the first plurality of edges includes at least 100, at least 1000, at least 2000, at least 5000, at least 10,000, at least 100,000, or at least 1 million edges. In some embodiments, the first plurality of edges includes no more than 5 million, no more than 100,000, no more than 10,000, or no more than 5000 edges. In some embodiments, the first plurality of edges includes from 100 to 1000, from 500 to 10,000, or from 5000 to 500,000 edges. In some embodiments, the first plurality of edges falls within another range starting no lower than 100 edges and ending no higher than 5 million edges. In some embodiments, the filtering the first plurality of edges comprises removing noise and/or edges that are not related to fiducial markers. Accordingly, in some embodiments, the second plurality of edges includes at least 10, at least 100, at least 1000, at least 2000, at least 5000, at least 10,000, at least 100,000, or at least $1 \times 10^6$ edges. In some embodiments, the second plurality of edges includes no more than 1 million, no more than 100,000, no more than 10,000, or no more than 5000 edges. In some embodiments, the second plurality of edges includes from 100 to 1000, from 500 to 10,000, or from 5000 to 500,000 edges. In some embodiments, the second plurality of edges falls within another range starting no lower than 10 edges and ending no higher than 1 million edges.

In some embodiments, the filtering the first plurality of edges comprises removing an edge-group having two or more edges that fail to satisfy a minimum inter-ring spacing width threshold. In some embodiments, the filtering the first plurality of edges comprising removing an edge-group having two or more edges that fail to satisfy a maximum inter-ring spacing width threshold. In some embodiments, the minimum inter-ring spacing width threshold and/or the maximum inter-ring spacing width threshold is any of the values for linewidths and/or inter-ring spacing widths disclosed herein.

Referring to Block 270, in some embodiments, the identifying the first plurality of edges in the array of pixel values is performed using Sobel edge detection, and the filtering the first plurality of edges comprises determining a corresponding normal of a tangent 408 of a respective edge 404 in the first plurality of edges by fitting the respective edge with a polynomial line and using a corresponding normal of the polynomial line to identify edges 404 in the first plurality of edges that are a member of an edge-group 406 common to the respective edge. Generally, Sobel edge detection performs a two-dimensional spatial gradient measurement on an image, thereby emphasizing regions of high spatial frequency that correspond to edges. In some embodiments, Sobel edge detection is used to find an approximate absolute gradient magnitude at each point in an input image (e.g., a grayscale image). Methods for Sobel edge detection are known in the art, as described in Kaur and Kant, 2014, "A Review on Comparison and Analysis of Edge Detection Techniques," IJRECE 2(1): 38-41, which is hereby incorporated herein by reference in its entirety.

Referring to Block 272, in some such embodiments, the fitting the respective edge with a polynomial line is performed at sub-pixel resolution. For instance, in some embodiments, a Sobel edge detection is performed using a sub-pixel measurement algorithm based on intensity integration threshold (IIT). The proposed method can be used to localize the sub-pixel edges in an inexpensive way by calculating the integration of the intensity across the edge and finding the point where the integration reaches the threshold. See, e.g., Chu et al., 2020, "Sub-pixel dimensional measurement algorithm based on intensity integration threshold," OSA Continuum 3(10): 2912, which is hereby incorporated herein by reference in its entirety.

Other methods for edge detection are contemplated for use in the present disclosure, as will be apparent to one skilled in the art. For instance, in some embodiments, the edge detection is performed using Sobel operator, Robert's cross operator, Prewitt operator, Laplacian of Gaussian (LoG), Canny edge detector, Laplace edge detection, Marr-Hildreth, and/or Haralick. See, e.g., Kaur and Kant, 2014, "A Review on Comparison and Analysis of Edge Detection Techniques," IJRECE 2(1): 38-41, which is hereby incorporated herein by reference in its entirety.

In some embodiments, the method includes, for each respective edge-group in the plurality of edge-groups of length M, determining a respective center for the respective edge-group. In some such embodiments, the respective center for the respective edge-group is obtained by averaging over all M edge points within the edge-group.

In some embodiments, referring again to Block 268, the method further includes identifying a respective fiducial center candidate using a circle Hough transform of each respective edge-group of length M (e.g., length six) in the plurality of edge-groups of length M (e.g., length six), thereby identifying a plurality of fiducial center candidates, where each respective fiducial center candidate in the plurality of fiducial center candidates is associated with a pixel in the array of pixels. The method further includes identifying a plurality of fiducial centers 410 from the plurality of fiducial center candidates by applying a threshold requirement to each fiducial center candidate in the plurality of fiducial center candidates.

For example, in some such embodiments, a circle Hough transform (CHT) is performed using the identified edge-group centers, assisted by the normal directions corresponding to the identified centers. In brief, as described above, for each respective edge-group center, CHT simulates candidate circles using the edge-group center to define candidate circle perimeters. The plurality of fiducial centers 410 is identified from the plurality of candidate circles at points (e.g., pixels) within the image where the number of intersecting candidate circle perimeters for one or more identified edge-group centers exceed a threshold value (e.g., reach a local maximum). Thus, a vote is performed to determine likely fiducial centers based on the number of intersecting candidate circle perimeters generated by the identified edge-group centers.

In some embodiments, the threshold value for intersecting candidate circle perimeters is a local maximum for each region of the image. In some embodiments, the threshold value for intersecting candidate circle perimeters is at least 2, at least 3, at least 4, at least 5, at least 10, at least 15, or at least 20 intersecting candidate circle perimeters.

Methods for circle Hough transform are known in the art, as described, for example, in Pedersen, 2009, "Circular Hough Transform," Encyclopedia of Biometrics; and Hassanein et al., 2015, "A Survey of Hough Transform, Theory, Techniques and Applications," ArXiv:1502.02160, each of which is hereby incorporated by reference.

Other methods of identifying fiducial centers are possible, as will be apparent to one skilled in the art. For instance, more generally, a Hough transform is used to detect lines, but can be applied to specific instances such as imperfect lines and shapes, including circles and curved edges. The Hough transform receives, as input, an image comprising edges and attempts to locate edges placed as straight lines. A vote is performed, in which every edge point in the image is transformed to all possible lines that could pass through that point, and points that exceed a threshold value of possible intersecting lines are identified as detected lines. See, e.g., 2009, "Line Detection by Hough transformation," available on the Internet at web.ipac.caltech.edu/staff/fmasci/home/astro_refs/HoughTrans_lines_09.pdf, which is hereby incorporated by reference.

Figure 4F:
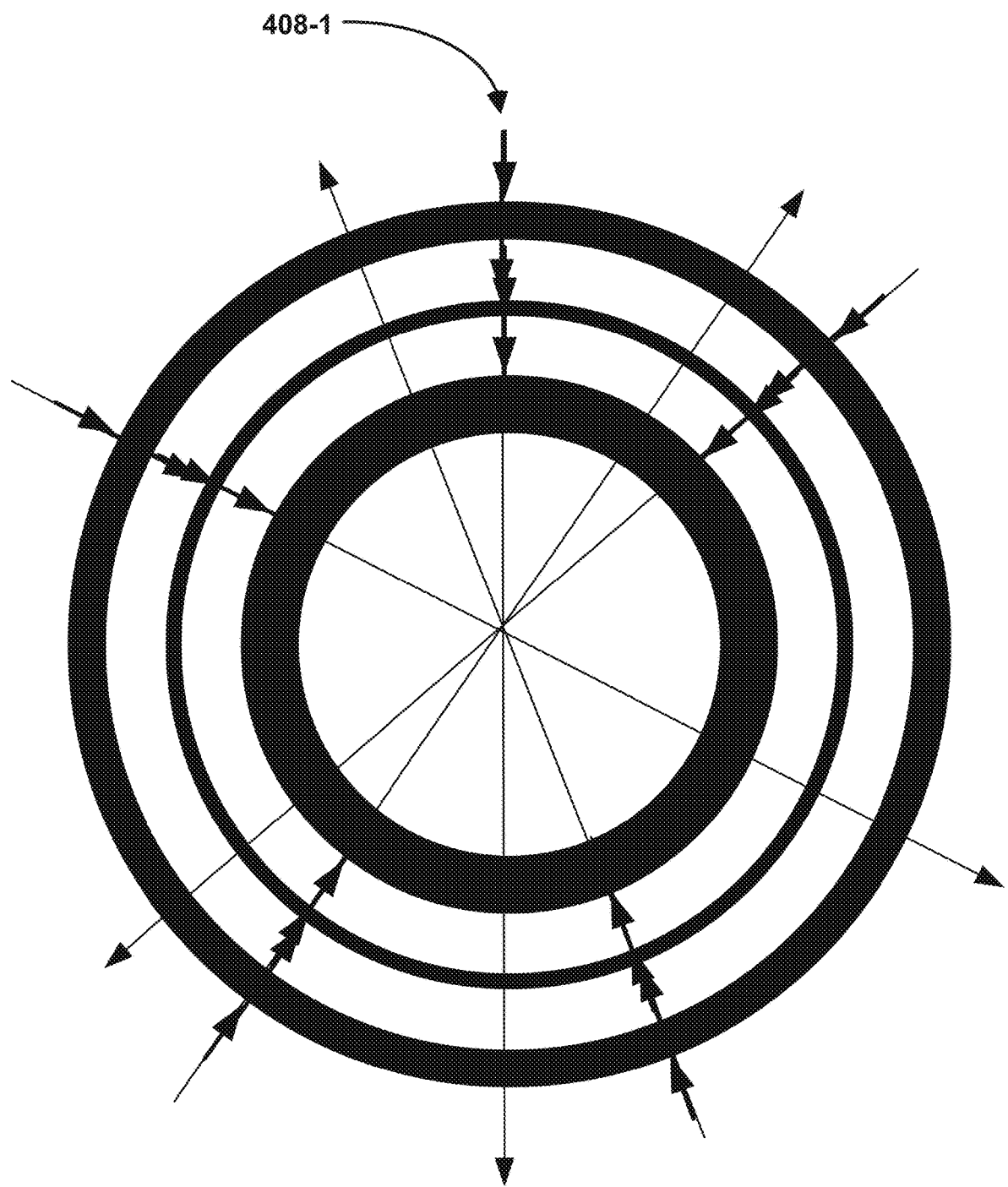
Figure 4G:
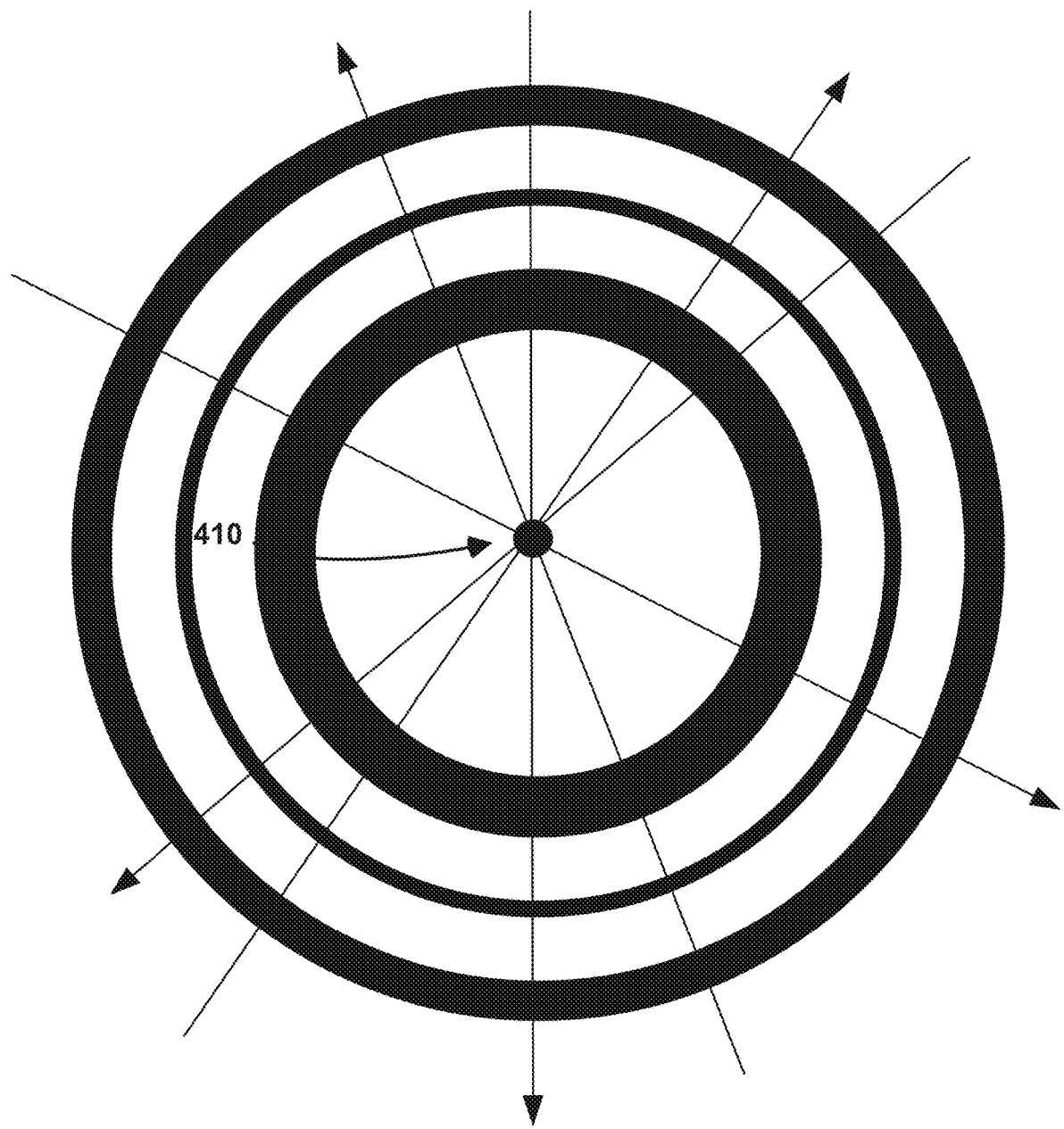
Figure 4H:
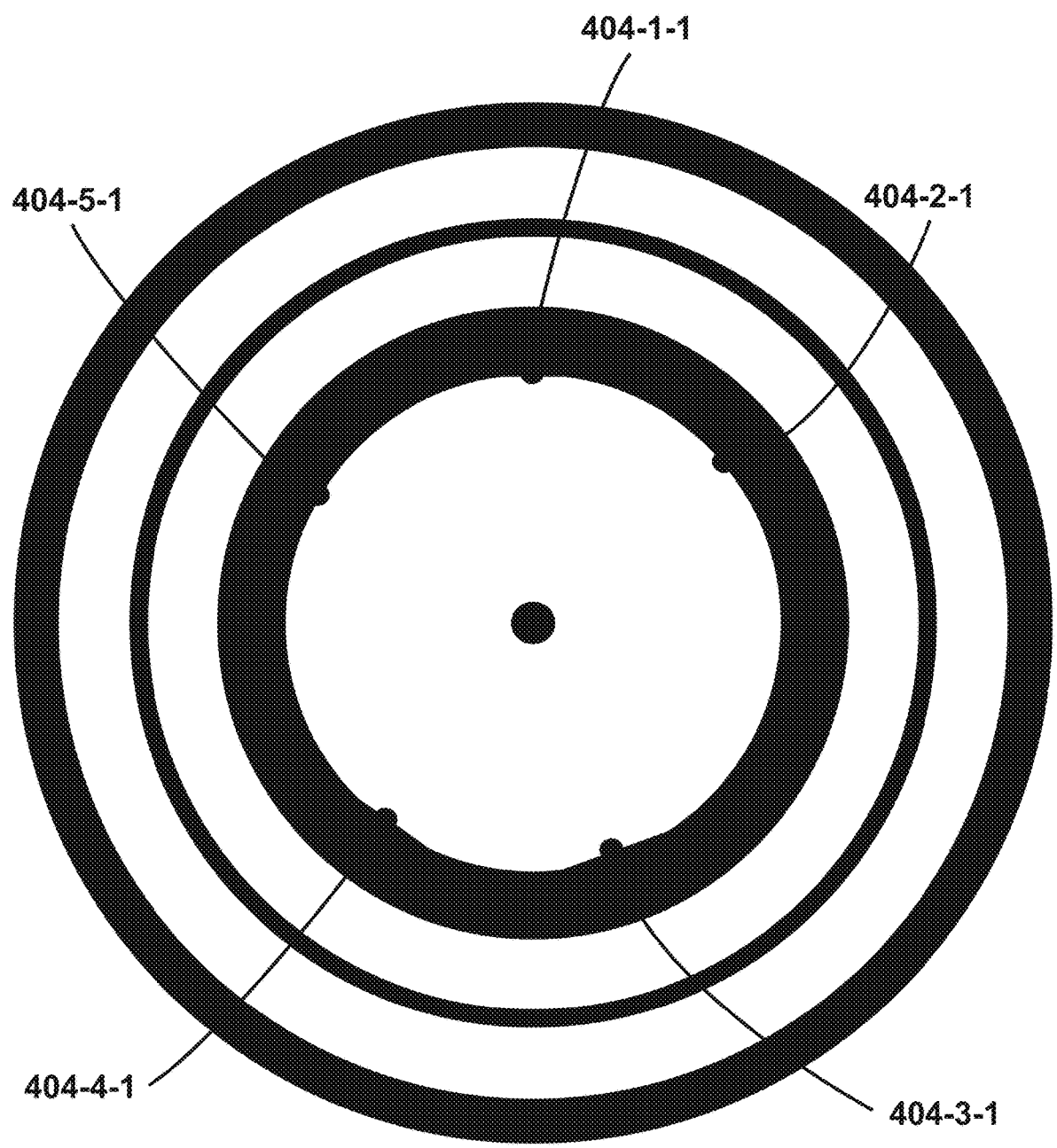

In some embodiments, the identifying a respective fiducial center candidate comprises applying a threshold requirement, for each pixel in the array of pixels, of a number of intersecting lines generated by an extension of the corresponding normal direction for each edge-group in the plurality of edge-groups. An example extended normal direction is illustrated in FIG. 4F (e.g., 408-1). Pixels that satisfy the threshold requirement are deemed fiducial centers (e.g., 410 in FIG. 4G). In some embodiments, the threshold requirement is at least 2, at least 3, at least 4, at least 5, at least 10, at least 15, or at least 20 intersecting lines.

In some embodiments, referring again to Block 268, the method further includes associating each respective edge-group 406 of length M (e.g., length six) in the plurality of edge-groups of length M (e.g., length six) with a corresponding fiducial center 410 in the plurality of fiducial centers based at least on a proximity of the respective edge-group of length M (e.g., length six) to the corresponding fiducial center. In other words, each respective edge-group in the plurality of edge-groups of length M are grouped according to their proximity to one or more fiducial centers. In some embodiments, each respective edge-group in the plurality of edge-groups of length M are associated with the closest fiducial center. Accordingly, as illustrated in FIG. 4C, edge-groups 406-1, 406-2, 406-3, 406-4, and 406-5 are associated with a closest located fiducial center 410.

Figure 4I:
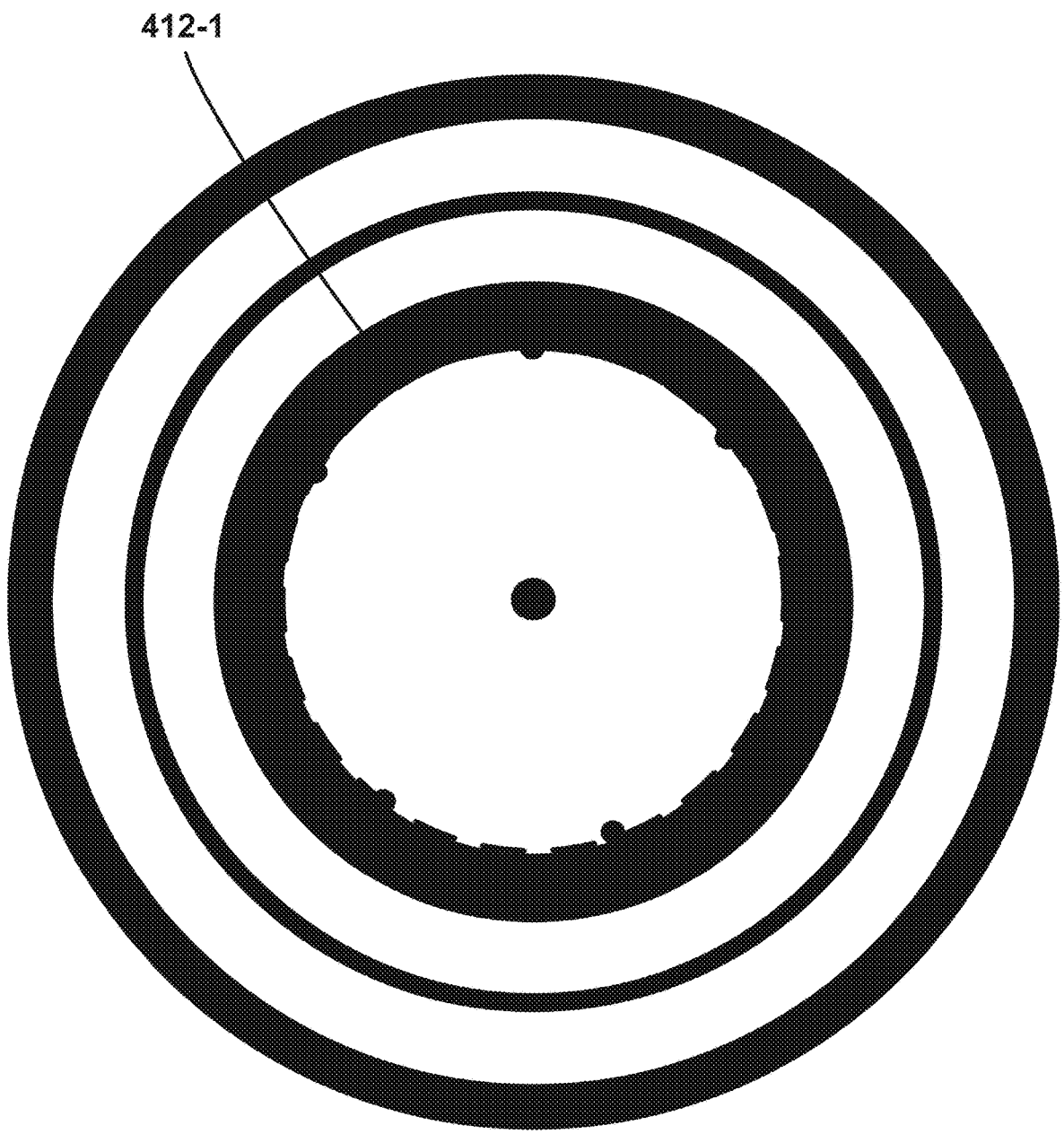
Figure 4J:
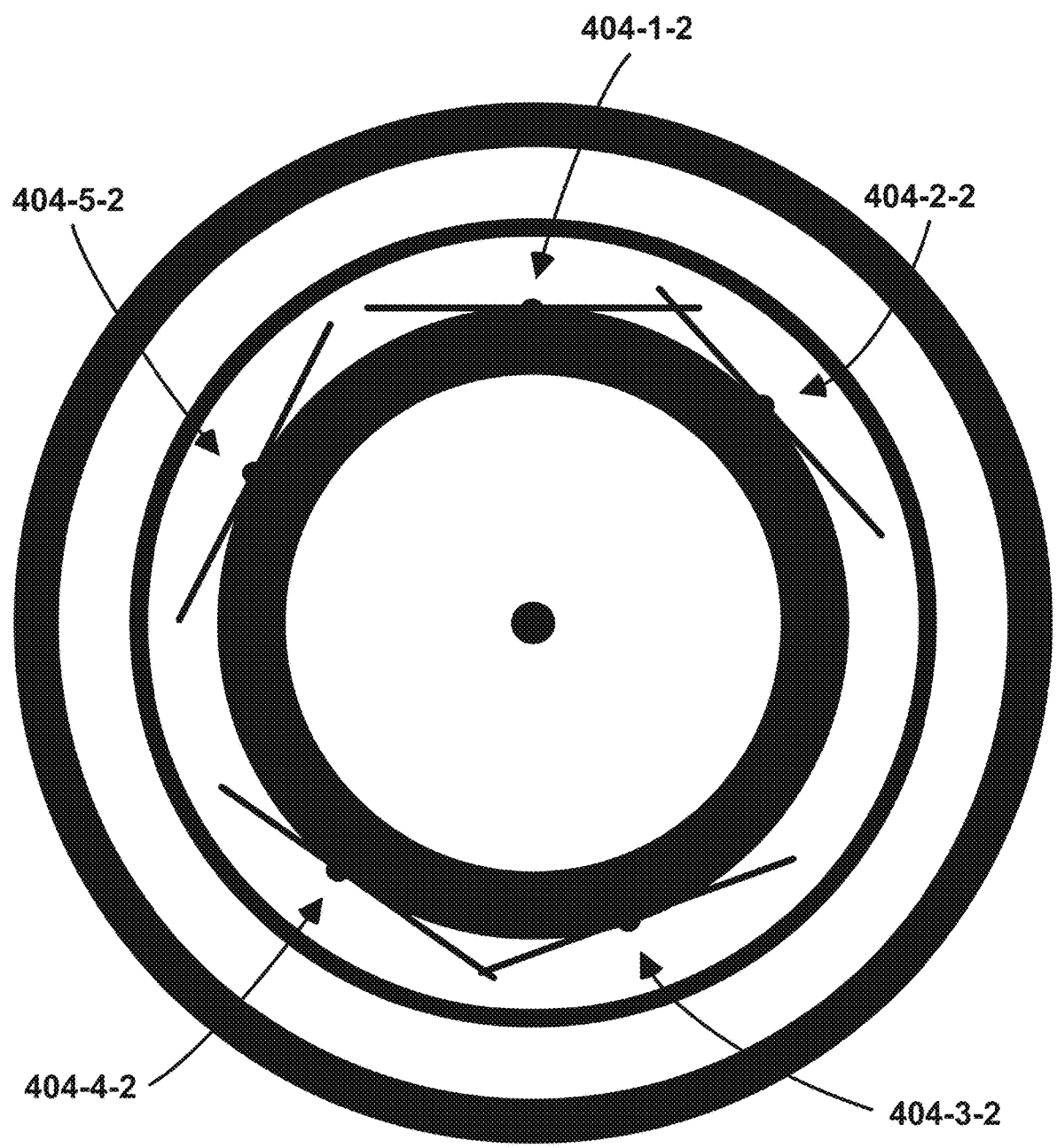
Figure 4K:
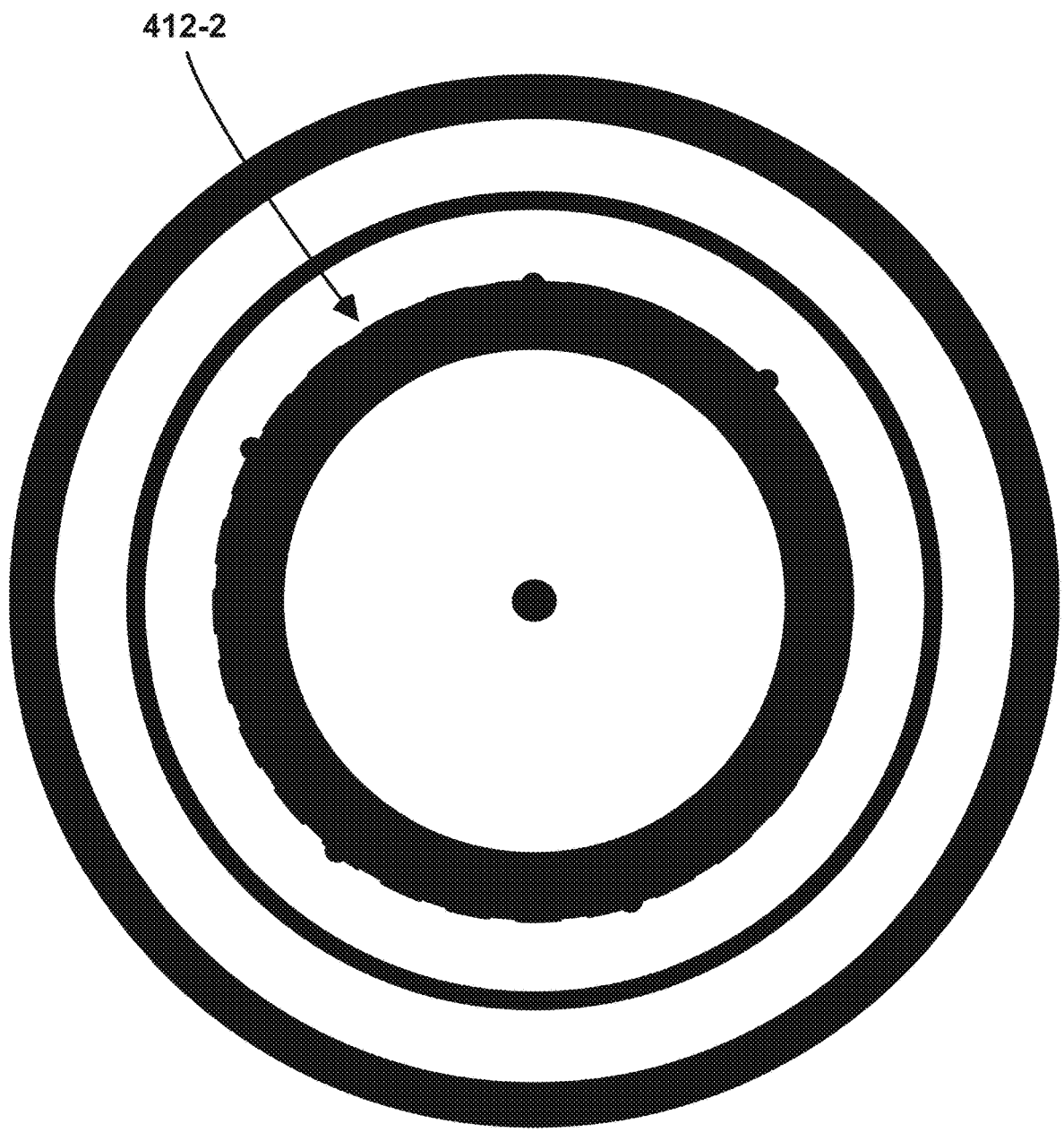

In some embodiments, the method includes arranging, for each respective edge-group 406 of length M (e.g., length six) in the plurality of edge-groups of length M (e.g., length six), each edge 404 in the respective edge-group of length M (e.g., length six) with respect to the fiducial center 410 associated with the respective edge-group to form a corresponding ordered set of edges for each fiducial marker in the first plurality of fiducial markers, thereby forming a respective ordered set of concentric circles 412 about each respective fiducial center in the plurality of fiducial centers. In some such implementations, each edge in each respective edge-group is ordered such that the first edge corresponds to a first perimeter, a second edge corresponds to a second perimeter, and so on, using the distance between each edge point and the associated fiducial center. For an example edge-group of length six 406-1, each respective edge in the respective edge-group is ordered such that edge 404-1-1 is assigned to a first order (e.g., order 1), edge 404-1-2 is assigned to a second order (e.g., order 2), edge 404-1-3 is assigned to a third order (e.g., order 3), edge 404-1-4 is assigned to a fourth order (e.g., order 4), edge 404-1-5 is assigned to a fifth order (e.g., order 5), and edge 404-1-6 is assigned to a sixth order (e.g., order 6). When this ordering is performed for each respective edge-group of length six that is assigned to the associated fiducial center 410 (e.g., 406-1, 406-2, 406-3, 406-4, and 406-5), each respective edge that is assigned to a respective order forms a respective concentric circle about the fiducial center. Thus, as illustrated in FIGS. 4I1 and 4I, each respective edge that is assigned to the first order (e.g., 404-1-1, 404-2-1, 404-3-1, 404-4-1, and 404-5-1) forms a first concentric circle 412-1 about the fiducial center. Similarly, as illustrated in FIGS. 4J and 4K, each respective edge that is assigned to the second order (e.g., 404-1-2, 404-2-2, 404-3-2, 404-4-2, and 404-5-2) forms a second concentric circle 412-2 about the fiducial center.

In some embodiments, the edges of each edge-group are then ordered based on the distance between each edge and its corresponding fiducial center, from the closest edge (e.g., order 1) to the farthest edge from the fiducial center. Thus, for a fiducial marker comprising three concentric rings, the edge closest to the fiducial center in an edge-group of length six would correspond to the inner edge of the innermost circle (e.g., order 1), and the edge farthest from the fiducial center would correspond to the outer edge of the outermost circle (e.g., order 6).

In some embodiments, the edges of each edge-group are ordered based on the distance between each edge and its corresponding fiducial center, from the farthest edge (e.g., order 1) to the closest edge from the fiducial center.

In some embodiments, the method further includes refining the fiducial center by fitting the center against the plurality of edges in each respective order of edges corresponding to each respective concentric circle 412 about the fiducial center. Thus, a fitted fiducial center is generated for each respective order in a plurality of orders, thereby obtaining a plurality of fitted fiducial centers. In some such embodiments, the plurality of fitted fiducial centers is averaged, thus obtaining a refined fiducial center. The distance between the refined fiducial center and each respective edge in each respective edge-group is determined, and, for each respective order in the plurality of orders, the distances between the edges assigned to the respective order are averaged. Accordingly, the average distance between the edges assigned to a first order determines a corresponding first radius from the refined fiducial center for a corresponding first concentric circle 412-1, and the average distance between the edges assigned to a second order determines a corresponding second radius from the refined fiducial center for a corresponding second concentric circle 412-2.

As described above, the generated radii can be used to determine the respective linewidths and inter-ring spacing widths for each ring and inter-ring spacing of each respective fiducial marker identified using the foregoing procedure. When encoded into an N-digit code (e.g., a five bit ternary code), the identity of the fiducial marker can be elucidated (e.g., based on the unique assignment of N-digit codes).

Thus, referring again to Block 268, in some embodiments, the method includes determining, for each respective fiducial marker in the plurality of fiducial markers, at least a five bit ternary code of the fiducial marker from a radius of each concentric circle in the respective ordered set of concentric circles about the fiducial center of the respective fiducial marker.

In some embodiments, other methods of identifying the location of fiducial markers in the first plurality of fiducial markers are used.

For example, in some implementations, the analyzing the plurality of pixel values to identify a respective location of each fiducial marker in the first plurality of fiducial markers within the image comprises identifying a first plurality of edges in the plurality of pixel values. The first plurality of edges is filtered to identify a second plurality of edges from the first plurality of edges. Each edge in the second plurality of edges is a member of an edge-group (e.g., of length six) in a plurality of edge-groups (e.g., of length six) in the second plurality of edges. A corresponding center of each respective edge-group (e.g., of length six) in the plurality of edge-groups (e.g., of length six) is used to form a plurality of edge-links. Each respective edge-link in the plurality of edge-links comprises a corresponding set of edge-groups in the plurality of edge-groups. A respective center of each respective edge-group in the corresponding set of edge-groups is within a threshold distance of another edge-group in the corresponding set of edge-groups and comprises a corresponding set of six edges determined from the corresponding set of edge-groups. For each respective edge-link in the plurality of edge-links, the corresponding set of six edges of the respective edge-link is arranged with respect to a center of the edge-link to form a corresponding ordered set of six edges defining three corresponding concentric rings and two corresponding inter-ring spacings for the respective edge-link. For each respective edge-link in the plurality of edge-links, the respective pattern in the plurality of patterns for the respective edge-link is determined from a linewidth of each concentric ring in the corresponding three concentric rings and two corresponding inter-ring spacings of the respective edge-link in the image. For each respective edge-link in the plurality of edge-links, a respective location of the fiducial marker corresponding to the respective edge-link from a center of the corresponding three concentric rings of the respective edge-link is determined. For each respective edge-link in the plurality of edge-links, at least a five bit ternary code of the fiducial marker corresponding to the respective edge-link is determined from the respective pattern in the plurality of patterns corresponding to the respective edge-link.

In some such embodiments, each respective edge-group of length six in the plurality of edge-groups of length six defines a corresponding edge-group center in a plurality of edge-group centers, where the using a corresponding center of each edge-group of length six in the second plurality of edges to form a plurality of edge-links comprises building a Kd-tree using the plurality of edge-group centers. The Kd-tree is queried for pairs of edge-groups having a center within a cut-off distance of each other thereby identifying a plurality of valid edge-group pairs. A graph having a plurality of nodes connected by a plurality of edges is built. Each respective node in the plurality of nodes defines an edge-group center in the plurality of edge-group centers. Each edge in the plurality of edges defines a valid edge-group pair in the plurality of valid edge-group pairs. A plurality of edge-links is determined from the graph, where each edge-link in the plurality of edge-links consists of a corresponding set of edge-groups represented by the graph that are linked to each other in the graph by edges in the plurality of edges.

In some embodiments, fiducial markers are located manually (e.g., by user selection of fiducial markers using a graphical user interface).

Referring to Block 274, in some embodiments, the method includes aligning the respective location 128 of each fiducial marker 126 in the first plurality of fiducial markers within the image 122 with a location of each reference fiducial marker 136 in a plurality of reference fiducial markers of a first template 134 using an alignment algorithm to obtain a final transformation between the first plurality of fiducial markers of the image and the plurality of reference fiducial markers of the first template.

In some embodiments, the first template is selected from a plurality of templates using a substrate identifier of the substrate. For instance, in some embodiments, the plurality of templates is found in a template repository. In some such embodiments, each template in the plurality of templates includes at least reference positions (e.g., coordinates) for the corresponding plurality of reference fiducial markers 136 and a corresponding coordinate system 140. In some embodiments, the coordinate system is inferred from the reference positions. In some embodiments, the coordinate system comprises the location (coordinates) of capture spots 138 on the substrate. In some embodiments, the plurality of templates comprises 2, 3, 4, 5, 6, 7, 8, 9, 10, 11, 12, 13, 14, 15, 16, 17, 18, 19, 20 or more templates. In some embodiments, the plurality of templates comprises 25 or more, 30 or more 50 or more or 100 or more templates. In some embodiments, the plurality of templates comprises 1000 or more templates.

In some embodiments, a template is formed from a substrate printing instruction file that specifies how to print the capture spots on the substrate. In some such embodiments, the substrate printing instruction file is analyzed to create a template for each substrate and this template is provided when the substrate identifier is provided. For information on example substrate printing instruction files, see, e.g., Zhai, 2001, "Making GenePix Array List (GAL) Files," GenePix Application Note, Molecular Devices, pp. 1-9, which is hereby incorporated by reference.

In some embodiments, the corresponding plurality of reference fiducial spots 136 of the first template 134 comprises between 100 fiducial markers and 1000 fiducial markers, between 200 fiducial markers and 800 fiducial markers, between 300 fiducial markers and 700 fiducial markers or between 500 and 600 fiducial markers. In some embodiments, the first template has at least as many reference fiducial markers as the number of fiducial markers on the substrate. In some embodiments, the template and/or the corresponding substrate have less than 100 fiducial markers, less than 50 fiducial markers or less than 25 fiducial markers. In some embodiments, the template and/or the corresponding substrate have more than 1000 fiducial markers, more than 1500 fiducial markers or more than 3000 fiducial markers. In some embodiments, each capture spot has been printed with the same capture probes. In other embodiments, each capture spot is printed with an independent set of capture probes and the template tracks not only the position on the substrate of each respective capture spot, but also the independent set of capture probes that have been printed on the respective capture spot. In some embodiments, the coordinate system provides an explicit location of each capture spot on the substrate. In some embodiments, the coordinate system provides an orientation of the substrate relative to the fiducial markers and the orientation is used to reference a list of capture spot locations in a data source that is external to the template. One of skill in the art will appreciate that there are a number of ways to implement the template coordinate system based on the present disclosure (e.g., as an explicit list of capture spot locations, an orientation derived from the fiducial spots coupled with an external list of capture spot locations, etc.) and all such methods are encompassed by the present disclosure.

In some embodiments, the aligning the respective location 128 of each fiducial marker 126 in the first plurality of fiducial markers within the image 122 with a location of each reference fiducial marker 136 in a plurality of reference fiducial markers of a first template 134 comprises a point set registration problem, the goal of which is to assign correspondences between two sets of points (the plurality of the fiducial markers of the image and the plurality of reference fiducial markers of the first template) and/or to recover the transformation that maps one point set to the other. In some embodiments, in order to determine which of the eight possible orientations a substrate is in (four 90 degree rotations plus reflection), all eight orientations are concurrently run and the orientation with the lowest residual error is chosen, as long as the second lowest residual error is significantly higher. Referring to Block 276, in some embodiments, the alignment algorithm is a linear regression.

Referring to Block 278, in some embodiments, the analyzing is performed on (i) a two-dimensional affine transformation of the array of pixel values and (ii) the two-dimensional affine transformation taking mirroring into consideration. In some such embodiments, the alignment algorithm computes a first residual value based on the respective location of each fiducial marker in the first plurality of fiducial markers within the two-dimensional affine transformation of the array of pixel values and a second residual value based on the respective location of each fiducial marker in the first plurality of fiducial markers within the two-dimensional affine transformation taking mirroring into consideration, and the alignment algorithm selects between the image and a mirror image of the image to compute the final transformation based on a comparison of the first and second residual value.

For instance, in some embodiments, the obtaining the transformation includes determining whether the image has been flipped. Accordingly, the method includes fitting a 2-dimensional affine transformation to estimate the reflection matrix. When a mirroring has been deemed to occur, the 2-dimensional affine transformation is discarded, and the method includes fitting a 2-dimensional similarity transform taking mirroring into consideration. When a mirroring has been deemed not to occur, the 2-dimensional affine transformation is discarded, and the method includes fitting a 2-dimensional similarity transform without mirroring.

Referring to Block 280, in some embodiments, the final transformation includes a similarity transform that comprises rotation, translation, and/or isotropic scaling of the first plurality of fiducial markers of the image to minimize a residual error between the first plurality of fiducial markers of the image and the corresponding plurality of reference fiducial markers.

In some embodiments, the final transformation is a similarity transform. A similarity transformation allows only for translation, rotation and isotropic scaling. Thus, when a similarity transformation is used, the plurality of fiducial markers of the image are rotated, translated, and/or isotropically scaled to minimize a residual error between the plurality of fiducial markers and the corresponding plurality of reference fiducial markers.

In some embodiments, the final transformation is a rigid transform. A rigid transformation allows only for translation and rotation. Thus, when a rigid transformation is used, the plurality of fiducial markers of the image are rotated and/or translated to minimize a residual error between the plurality of fiducial markers and the corresponding plurality of reference fiducial markers.

In some embodiments, the transformation is a non-rigid transform that comprises anisotropic scaling and skewing of the plurality of fiducial markers of the image to minimize a residual error between the plurality of fiducial markers and the corresponding plurality of reference fiducial markers. In some embodiments, the non-rigid transform is an affine transformation. In some embodiments, the alignment algorithm is a coherent point drift algorithm. See, e.g., Myronenko et al., 2007, "Non-rigid point set registration: Coherent Point Drift," NIPS, 1009-1016; and Myronenko and Song, "Point Set Registration: Coherent Point Drift," arXiv:0905.2635v1, 15 May 2009, each of which is hereby incorporated by reference, for disclosure on the coherent point drift algorithm. In some embodiments, the coherent point drift algorithm that is used is an implementation in Python called pycpd." See, Gatti and Khallaghi, 2022, "PyCPD: Pure NumPy Implementation of the Coherent Point Drift Algorithm," Journal of Open Source Software 7(80), p. 4681, which is hereby incorporated herein by reference.

In some embodiments, the alignment algorithm is an iterative closest point algorithm. See, for example, Chetverikov et al., 2002, "The Trimmed Iterative Closest Point Algorithm," Object recognition supported by user interaction for service robots, Quebec City, Quebec, Canada, ISSN: 1051-4651; and Chetverikov et al., 2005, "Robust Euclidean alignment of 3D point sets; the trimmed iterative closest point algorithm," Image and Vision Computing 23(3), pp. 299-309, each of which is hereby incorporated herein by reference in its entirety.

In some embodiments, the alignment algorithm is a robust point matching algorithm (see, for example, Chui and Rangarajanb, 2003, "A new point matching algorithm for non-rigid registration," Computer Vision and Image Understanding 89(2-3), pp. 114-141, which is hereby incorporated herein by reference in its entirety) or a thin-plate-spline robust point matching algorithm (see, for example, Yang, 2011, "The thin plate spline robust point matching (TPS-RPM) algorithm: A revisit," Pattern Recognition Letters 32(7), pp. 910-918, which is hereby incorporated herein by reference in its entirety).

Referring to Block 282, in some embodiments, the final transformation includes a perspective transform. In some such embodiments, a perspective transform takes tilting into consideration (e.g., for a substrate mounted onto an imaging platform).

Referring to Block 284, the method further includes using the final transformation and a coordinate system 140 of the first template 134 to register the image 122 to the set of capture spots 138. In some implementations, the alignment uses the transformation to map the fiducial markers on the substrate in the image onto the reference fiducial markers of the template. In some such implementations, upon such mapping, it is possible to determine the location of each capture spot in the image.

Referring to Block 286, in some embodiments the image 122 is analyzed, after the using the final transformation, in conjunction with spatial analyte data 148 associated with each capture spot, thereby performing spatial analysis of analytes. Example methods for spatial analysis of analytes are described in further detail herein (see, for example, the section entitled, "Methods for Spatial Analysis of Analytes," above).

For instance, in some embodiments, analysis of the spatial analyte data provides a classification of one or more capture spots in the set of capture spots, based on the plurality of analytes for the sample. In some embodiments, the classification includes an abundance, a detection (e.g., yes or no, presence or absence, etc.), a biological condition (e.g., a tissue type, cell type, a lineage, a disease status, etc.), and/or an annotation (e.g., of membership in a panel of interest and/or a cluster of analytes determined using clustering analysis) of one or more analytes in the plurality of analytes.

Referring to Block 288, in some embodiments, the spatial analyte data associated with each capture spot is nucleic acid sequencing data associated with each capture spot. Accordingly, in some embodiments, the spatial analyte data provides sequencing information for each analyte in a plurality of analytes from the sample mapping to each capture spot in the set of capture spots. In some embodiments, the sequencing information is for a plurality of nucleic acids (e.g., RNA and/or DNA). In some embodiments, the spatial analyte data provides abundance information for each analyte in a plurality of analytes. In some embodiments, the abundance information is for DNA, RNA, proteins, or a combination thereof.

In some embodiments, the spatial analyte data is obtained by any suitable method. For example, in some embodiments, the spatial analyte data is obtained using a sequencing device such as, without limitation, a sequencing system by Illumina®, Pacific Biosciences (PacBio®), Oxford Nanopore®, or Life Technologies (Ion Torrent®). Alternatively, or in addition, the spatial analyte data may be obtained by sequencing using nucleic acid amplification, polymerase chain reaction (PCR) (e.g., digital PCR, quantitative PCR, or real time PCR), or isothermal amplification. In some examples, such systems provide sequencing reads (also "reads" herein). A read may include a string of nucleic acid bases corresponding to a sequence of a nucleic acid molecule that has been sequenced. Apparatuses suitable for obtaining the sequencing information of spatial analyte data are further described in, e.g., U.S. Patent Application No. 63/080,547, entitled "Sample Handling Apparatus and Image Registration Methods," filed Sep. 18, 2020, U.S. Patent Application Publication No. US 2023-0017773 A1, entitled "Fluid Delivery Methods," published Jan. 19, 2023, International Patent Publication No. WO2022/061150, published Mar. 24, 2022, entitled "Sample Handling Apparatus and Image Registration Methods," and PCT Application No. US2019/065100, entitled "Imaging system hardware," filed Dec. 6, 2019, each of which is hereby incorporated by reference herein in its entirety.

In some embodiments, the method further comprises using the spatial analyte data to characterize a biological condition in a subject. For instance, in some embodiments, the spatial analyte data is used to determine whether or not the subject has a disease or a stage of a disease. In some embodiments, the spatial analyte data is used to determine a probability or likelihood that the subject has a disease or a stage of a disease. In some embodiments, it is known that the subject has a disease and the spatial analyte data is used to determine a prognosis for the subject regarding the disease. In some embodiments, the disease is cancer or diabetes. In some embodiments, the disease is a cancer, hematologic disorder, autoimmune disease, inflammatory disease, immunological disorder, metabolic disorder, neurological disorder, genetic disorder, psychiatric disorder, gastroenterological disorder, renal disorder, cardiovascular disorder, dermatological disorder, respiratory disorder, or a viral infection.

In some embodiments, the spatial analyte data is used to associate one or more different species of analytes (e.g., polynucleotides, polypeptides, etc.) from the sample with one or more physical properties of the sample. For example, the one or more different species of analytes can be associated with locations of the analytes in the sample. Such information (e.g., proteomic information when the analyte binding moiety(ies) recognizes a polypeptide(s)) can be used in association with other spatial information (e.g., genetic information from the sample, such as DNA sequence information, transcriptome information such as sequences of transcripts, or both). For example, a cell surface protein of a cell can be associated with one or more physical properties of the cell (e.g., a shape, size, activity, or a type of the cell). The one or more physical properties can be characterized by imaging the cell. The cell can be bound by an analyte capture agent comprising an analyte binding moiety that binds to the cell surface protein and an analyte binding moiety barcode that identifies that analyte binding moiety, and the cell can be subjected to spatial analysis (e.g., any of the variety of spatial analysis methods described herein). For example, an analyte capture agent bound to a cell surface protein (or a portion of such analyte capture agent, e.g., a portion comprising the analyte binding moiety barcode) can be bound to a capture probe (e.g., a capture probe on an array), where the capture probe includes a capture domain that interacts with an analyte capture sequence present on the capture agent barcode domain of the analyte capture agent. In some embodiments, profiles of individual cells or populations of cells in spatial analyte data can be compared to profiles from other cells, e.g., 'normal' cells, to identify variations in analytes, which can provide diagnostically relevant information. In some embodiments, these profiles can be useful in the diagnosis of a variety of disorders that are characterized by variations in cell surface receptors, such as cancer and other disorders.

In some embodiments, method further comprises visualizing, on a visualization system (e.g., a computer with a display), the image of the sample overlayed onto spatial analyte data for the plurality of analytes of the sample. In some embodiments, the visualization system comprises a display on the computer system comprising one or more processing cores and a memory. In some embodiments, the visualization system is a display on a device, such as a sample handling apparatus.

In some embodiments, method further comprises visualizing, on a visualization system (e.g., a computer with a display), a first image of the sample overlayed onto one or more of spatial analyte data for the plurality of analytes of the sample and one or more additional (e.g., second) images of the sample.

In some embodiments, the visualization system includes visualization tools that can be configured to provide the first image, the one or more second images, the spatial dataset, and/or any features or overlays thereof as described herein, in one or more visual formats. In some embodiments, the first image, the second image, the spatial dataset, and/or any features or overlays thereof as described herein, are provided in a GUI of a display of the sample handling apparatus. In some embodiments, the visualization tools can be configured on a remote computing device that is communicatively coupled to the sample handling apparatus, such that the first image, the second image, the spatial dataset, and/or any features or overlays thereof as described herein, can be visualized and/or manipulated on the remote computing device.

In some embodiments, the visualization tools are configured to provide a user input system and user interface, such as a desktop application that provides interactive visualization functionality to perform any of the workflows or processes described herein. In some embodiments, the visualization tools include a browser that can be configured to enable users to evaluate and interact with different views of the spatial analyte data to quickly gain insights into the underlying biology of the samples being analyzed. The browser can be configured to evaluate significant analytes (e.g., genes), characterize and refine clusters of data, and to perform differential analysis (e.g., expression analysis) within the spatial context of an image and/or a spatial dataset.

In some embodiments, the visualization tools are configured to read from and write to files generated by a spatial analyte analysis and/or image analysis workflow. The files can be configured to include filed and unfiled versions of images and analyte data, including but not limited to, gene expression data for all barcoded locations on a substrate or slide, alignment data associated with alignment of a sample or portions of the sample and the barcoded locations of an array, and gene expression-based clustering information for the barcoded locations. The gene expression-based clustering information can include t-Distributed Stochastic Neighbor Embedding (t-SNE) and Uniform Manifold Approximation and Projection (UMAP) projections.

In some embodiments, the visualization system includes image setting functionality configured to adjust or configured settings associated with any of the workflows or processes described herein, including but not limited to fiducial marker display, scale display, rotation, and/or resetting the image data. In some embodiments, the visualization system includes one or more image manipulation tools, such as a pointer to select data or menu items, a lasso to select data, and a pen to annotate or mark data. The analyte data can be provided in a primary viewing panel.

In some embodiments, the visualization system includes a presentation of spatial analyte data organized with respect to clusters. In some embodiments, the presentation can provide representative clusters as violin plots, although a number of other non-limiting plot types can be envisioned. In some embodiments, the visualization system includes secondary viewing panels. The secondary viewing panels can provide one or more projections of the spatial analyte data provided in the primary viewing panel. For example, the secondary viewing panel can provide a spatial projection of the analyte data so that a user can interact with the spatial opacity and magnification settings of the data. The secondary viewing panel can provide an additional projection of the spatial analyte data other than or in addition to that shown on the primary viewing panel.

The primary viewing panel and secondary viewing panels can each individually be configured with image manipulation tools including, but not limited to, image resize functionality, image cropping functionality, image zoom functionality, image capture functionality, file view functionality, list view functionality, or the like.

Visualization and applications of spatial analyte data, including spatial analyte data overlayed on sample images, that are contemplated for use in the present disclosure are further described in U.S. Pat. No. 11,501,440, entitled "SYSTEMS AND METHODS FOR SPATIAL ANALYSIS OF ANALYTES USING FIDUCIAL ALIGNMENT," U.S. Patent Application Publication No. US2021-0150707 A1, entitled "SYSTEMS AND METHODS FOR BINARY TISSUE CLASSIFICATION," U.S. Pat. No. 11,514,575, entitled "Systems and Methods for Identifying Morphological Patterns in Tissue Samples," U.S. Patent Application Publication No. US2021-0155982 A1, entitled "Pipeline Spatial Analysis of Analytes," published May 27, 2021; International Patent Application Publication No. WO2022/

061150, entitled "Sample Handling Apparatus and Image Registration Methods," published Mar. 24, 2022, International Patent Application Publication No. WO 2021/252747, entitled "Fluid Delivery Methods," published Dec. 16, 2021, and PCT Application No. US2019/065100, entitled "Imaging system hardware," filed Dec. 6, 2019, each of which is hereby incorporated by reference herein in its entirety.

Additional Embodiments

Another aspect of the present disclosure provides a computer system comprising one or more processors, memory, and one or more programs for spatial analysis of analytes, where the one or more programs are stored in the memory and configured to be executed by the one or more processors. The one or more programs include instructions for obtaining a data structure, in electronic form, comprising an image of a sample on a substrate.

The substrate includes a plurality of border regions, where each respective border region in the plurality of border regions intersects another border region in the plurality of border regions. The substrate includes at least a first plurality of fiducial markers. The first plurality of fiducial markers comprises at least three fiducial markers. Each respective fiducial marker in the first plurality of fiducial markers encodes a different N-digit code, in a plurality of N-digit codes, where N is an integer greater than 3. At least two different border regions in the plurality of border regions includes a respective fiducial marker in the first plurality of fiducial markers. The substrate includes a set of capture spots (e.g., comprising at least 1000 capture spots). The image comprises a plurality of pixel values, each respective pixel value in the plurality of pixel values corresponding to a pixel in an array of pixels (e.g., comprising at least 100,000 pixels).

The plurality of pixel values is analyzed to identify a respective location of each fiducial marker in the first plurality of fiducial markers within the image.

The respective location of each fiducial marker in the first plurality of fiducial markers within the image is aligned with a location of each reference fiducial marker in a plurality of reference fiducial markers of a first template using an alignment algorithm to obtain a final transformation between the first plurality of fiducial markers of the image and the plurality of reference fiducial markers of the first template.

The final transformation and a coordinate system of the first template are used to register the image to the set of capture spots. The image is analyzed, after the using, in conjunction with spatial analyte data associated with each capture spot, thereby performing spatial analysis of analytes.

Another aspect of the present disclosure provides a computer readable storage medium storing one or more programs, the one or more programs comprising instructions, which when executed by an electronic device with one or more processors and a memory cause the electronic device to perform spatial analysis of analytes by a method comprising obtaining a data structure, in electronic form, comprising an image of a sample on a substrate.

The substrate includes a plurality of border regions, where each respective border region in the plurality of border regions intersects another border region in the plurality of border regions. The substrate includes at least a first plurality of fiducial markers. The first plurality of fiducial markers comprises at least three fiducial markers. Each respective fiducial marker in the first plurality of fiducial markers encodes a different N-digit code, in a plurality of N-digit codes, where N is an integer greater than 3. At least two different border regions in the plurality of border regions includes a respective fiducial marker in the first plurality of fiducial markers. The substrate includes a set of capture spots (e.g., comprising at least 1000 capture spots). The image comprises a plurality of pixel values, each respective pixel value in the plurality of pixel values corresponding to a pixel in an array of pixels (e.g., comprising at least 100,000 pixels).

The plurality of pixel values is analyzed to identify a respective location of each fiducial marker in the first plurality of fiducial markers within the image.

The respective location of each fiducial marker in the first plurality of fiducial markers within the image is aligned with a location of each reference fiducial marker in a plurality of reference fiducial markers of a first template using an alignment algorithm to obtain a final transformation between the first plurality of fiducial markers of the image and the plurality of reference fiducial markers of the first template.

The final transformation and a coordinate system of the first template are used to register the image to the set of capture spots. The image is analyzed, after the using, in conjunction with spatial analyte data associated with each capture spot, thereby performing spatial analysis of analytes.

Another aspect of the present disclosure provides a computer system including one or more processors and memory storing one or more programs for spatial analysis of analytes. It will be appreciated that this memory can be on a single computer, a network of computers, one or more virtual machines, or in a cloud computing architecture. The one or more programs are configured for execution by the one or more processors. The one or more programs include instructions for performing any of the methods disclosed herein.

Still another aspect of the present disclosure provides a computer readable storage medium storing one or more programs to be executed by an electronic device. The one or more programs include instructions for the electronic device to perform spatial analysis of analytes by any of the methods disclosed herein. It will be appreciated that the computer readable storage medium can exist as a single computer readable storage medium or any number of component computer readable storage mediums that are physically separated from each other.

EXAMPLES

Example 1—Image Registration Using Fiducial Markers

FIG. 10 illustrates a set of 12 unique fiducial markers used for performance testing of the presently disclosed systems and methods. The set of fiducial markers was printed in titanium as a 5 mm by 5 mm array onto a 25 mm by 74 mm glass slide, each fiducial marker having a thickness of 50 nm and a total diameter of 240 µm. Each fiducial marker consisted of three concentric rings and two inter-ring spacings, where the width of each respective ring and each respective inter-ring spacing was selected from 10 µm, 15 µm, and 20 µm. The respective N-digit code for each respective fiducial marker was a five bit ternary code obtained using the selected ring widths and inter-ring spacing widths. For instance, a five-digit code of 10-10-10-10-10 indicates that each of the three rings has a width of 10 µm and each of the two inter-ring spacings has a width of 10 µm. As another example, a five-digit code of 20-20-20-15-10 indicates a fiducial marker having a pattern comprising, from the outermost ring to the innermost ring, a first (e.g., outermost) ring having a width of 20 µm, a first inter-ring spacing having a width of 20 µm, a second (e.g., middle) ring having a width of 20 µm, a second inter-ring spacing having a width of 15 µm, and a third (e.g., innermost) ring having a width of 10 µm. The set of fiducial markers was imaged under dry conditions using an imaging instrument with red illumination, and with the fiducial markers facing the illumination.

Figure 11:
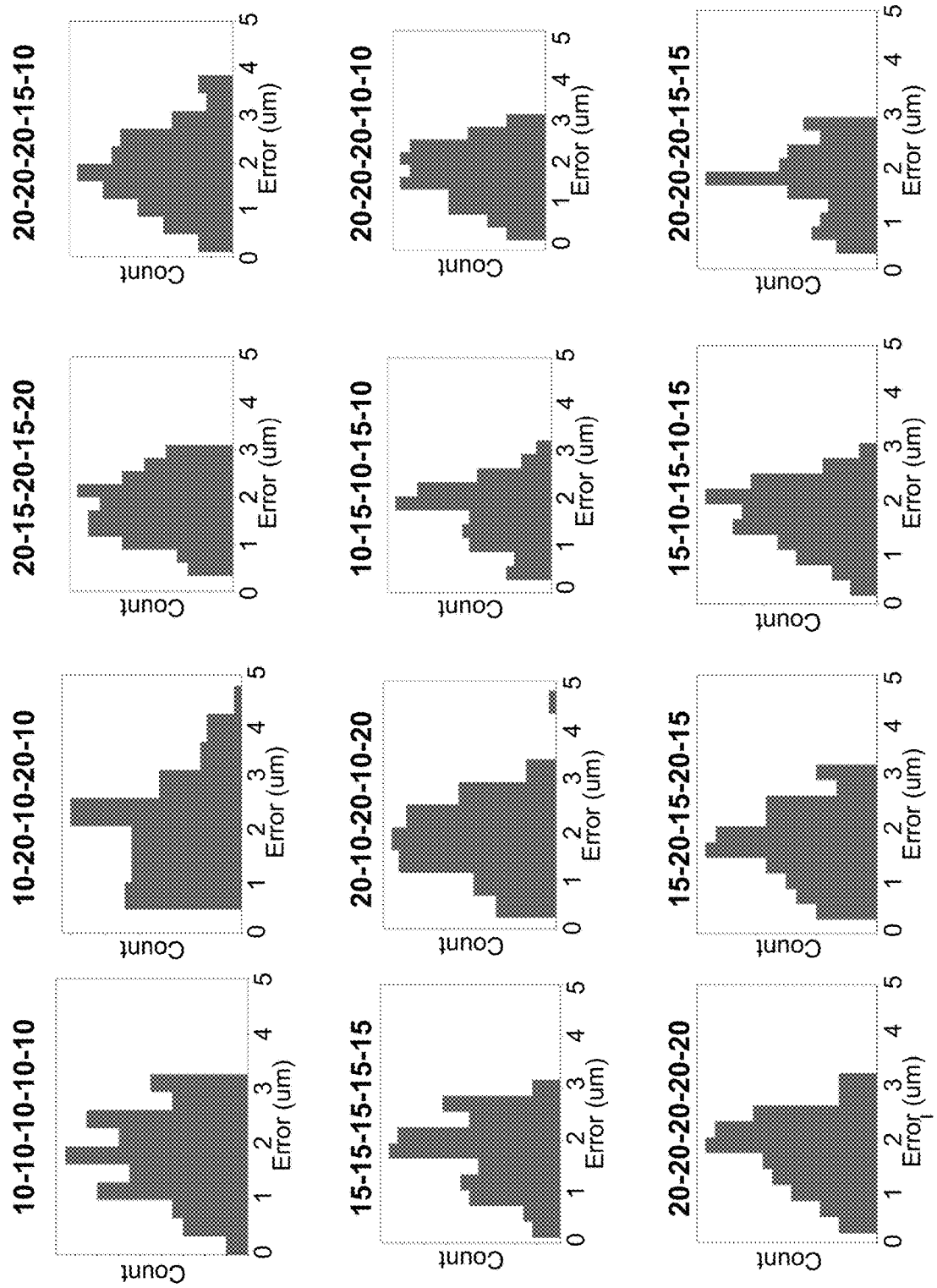
FIG. 11 shows performance metrics obtained for each of the example fiducial markers in FIG. 10, using the systems and methods described herein, in accordance with an embodiment of the present disclosure.

The image obtained for the set of fiducial markers was then used for identifying the location of each respective fiducial marker, and for subsequent alignment and registration of the image with reference fiducial markers in a template, in accordance with an embodiment of the present disclosure. FIG. 11 shows that the majority of registration errors for each of the identified fiducial centers was observed to be within 3 µm. These results indicate that the methods disclosed herein can be used to accurately, and within a small margin of error, identify the locations of fiducial markers that can be used for image registration and downstream spatial analysis of analytes.

REFERENCES CITED AND ALTERNATIVE EMBODIMENTS

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

The present invention can be implemented as a computer program product that comprises a computer program mechanism embedded in a non-transitory computer readable storage medium. For instance, the computer program product could contain the program modules shown in FIG. 1, and/or described in FIGS. 2A-I. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed:

1. A method of spatial analysis of analytes comprising:
A) obtaining a data structure in electronic form comprising an image of a sample on a substrate, wherein:
the substrate includes a plurality of border regions, wherein each respective border region in the plurality of border regions intersects another border region in the plurality of border regions,
the substrate includes at least a first plurality of fiducial markers,
the first plurality of fiducial markers comprises at least three fiducial markers,
each respective fiducial marker in the first plurality of fiducial markers encodes a different N-digit code, in a plurality of N-digit codes, wherein N is an integer greater than 3,
at least two different border regions in the plurality of border regions includes a respective fiducial marker in the first plurality of fiducial markers,
the substrate includes a set of capture spots, wherein the set of capture spots comprises at least 1000 capture spots, and
the image comprises a plurality of pixel values, each respective pixel value in the plurality of pixel values corresponding to a pixel in an array of pixels, wherein the array of pixels comprises at least 100,000 pixels;
B) analyzing the plurality of pixel values to identify a respective location of each fiducial marker in the first plurality of fiducial markers within the image;
C) aligning the respective location of each fiducial marker in the first plurality of fiducial markers within the image with a location of each reference fiducial marker in a plurality of reference fiducial markers of a first template using an alignment algorithm to obtain a final transformation between the first plurality of fiducial markers of the image and the plurality of reference fiducial markers of the first template;
D) using the final transformation and a coordinate system of the first template to register the image to the set of capture spots; and
E) analyzing the image after the using D) in conjunction with spatial analyte data associated with each capture spot, thereby performing spatial analysis of analytes.

2. The method of claim 1, wherein
the plurality of border regions consists of four border regions,
the first plurality of fiducial markers comprises a plurality of subsets of fiducial markers,
each respective border region in the plurality of border regions is associated with a respective subset of fiducial markers in the plurality of subsets of fiducial markers,
each respective fiducial marker in the first plurality of fiducial markers has a different pattern in a plurality of patterns,
the plurality of patterns consists of between 20 and 1000 patterns, and
each pattern in the plurality of patterns encodes a different N-digit code in the plurality of N-digit codes.

3. The method of claim 2, wherein each respective pattern in the plurality of patterns is a different concentric closed-form arrangement.

4. The method of claim 3, wherein each different concentric closed-form arrangement is a different concentric circular pattern.

5. The method of claim 1, wherein each fiducial marker in the first plurality of fiducial markers has a width of between 0.001 microns and 25 microns.

6. The method of claim 4, wherein
each respective pattern in the plurality of patterns comprises a different pattern of at least three rings and at least two inter-ring spacings,
each ring of each respective pattern in the plurality of patterns is characterized by a respective linewidth in a set of at least three discrete linewidths, each of the at least two inter-ring spacings of each respective pattern in the plurality of patterns is characterized by one of at least three different inter-ring spacing widths, and a respective linewidth of each respective ring in the at least three rings of a respective pattern in the plurality of patterns together with a respective inter-ring spacing of each of the at least two inter-ring spacings of the respective pattern collectively encode at least a five bit ternary code that localizes the corresponding fiducial marker to a particular position on the substrate in accordance with the first template.

7. The method of claim 1, wherein the B) analyzing the plurality of pixel values to identify a respective location of each fiducial marker in the first plurality of fiducial markers within the image comprises:

identifying a first plurality of edges in the plurality of pixel values;

filtering the first plurality of edges to identify a second plurality of edges from the first plurality of edges, wherein each edge in the second plurality of edges is a member of an edge-group of length six in a plurality of edge-groups of length six in the second plurality of edges;

identifying a respective fiducial center candidate using a circle Hough transform of each respective edge-group of length six in the plurality of edge-groups of length six, thereby identifying a plurality of fiducial center candidates, wherein each respective fiducial center candidate in the plurality of fiducial center candidates is associated with a pixel in the array of pixels;

identifying a plurality of fiducial centers from the plurality of fiducial center candidates by applying a threshold requirement to each fiducial center candidate in the plurality of fiducial center candidates;

associating each respective edge-group of length six in the plurality of edge-groups of length six with a corresponding fiducial center in the plurality of fiducial centers based at least on a proximity of the respective edge-group of length six to the corresponding fiducial center;

arranging, for each respective edge-group of length six in the plurality of edge-groups of length six, each edge in the respective edge-group of length six with respect to the fiducial center associated with the respective edge-group to form a corresponding ordered set of edges for each fiducial marker in the first plurality of fiducial markers, thereby forming a respective ordered set of concentric circles about each respective fiducial center in the plurality of fiducial centers; and determining, for each respective fiducial marker in the plurality of fiducial markers, the at least five bit ternary code of the fiducial marker from a radius of each concentric circle in the respective ordered set of concentric circles about the fiducial center of the respective fiducial marker.

8. The method of claim 7, wherein the identifying the first plurality of edges in the array of pixel values is performed using Sobel edge detection, and the filtering the first plurality of edges comprises determining a corresponding normal of a tangent of a respective edge in the first plurality of edges by fitting the respective edge with a polynomial line and using a corresponding normal of the polynomial line to identify edges in the first plurality of edges that are a member of an edge-group common to the respective edge.

9. The method of claim 8, wherein the fitting the respective edge with a polynomial line is performed at sub-pixel resolution.

10. The method of claim 1, wherein the first plurality of fiducial markers is made out of titanium, chromium, platinum, tantalum, gold, a combination thereof, or an alloy thereof.

11. The method of claim 1, wherein the first plurality of fiducial markers has a thickness of between 10 nm and 50 nm.

12. The method of claim 1, wherein the first plurality of fiducial markers has a thickness of between 40 nm and 300 nm.

13. The method of claim 1, wherein the alignment algorithm is a linear regression.

14. The method of claim 1, wherein the analyzing B) is performed on (i) a two-dimensional affine transformation of the array of pixel values and (ii) the two-dimensional affine transformation taking mirroring into consideration, the alignment algorithm computes a first residual value based on the respective location of each fiducial marker in the first plurality of fiducial markers within the two-dimensional affine transformation of the array of pixel values and a second residual value based on the respective location of each fiducial marker in the first plurality of fiducial markers within the two-dimensional affine transformation taking mirroring into consideration, and the alignment algorithm selects between the image and a mirror image of the image to compute the final transformation based on a comparison of the first and second residual value.

15. The method of claim 1, wherein the final transformation includes a similarity transform that comprises rotation, translation, and isotropic scaling of the first plurality of fiducial markers of the image to minimize a residual error between the first plurality of fiducial markers of the image and the corresponding plurality of reference fiducial markers.

16. The method of claim 1, wherein the final transformation includes a perspective transform.

17. The method of claim 1, wherein:

the sample is a sectioned tissue sample, each respective capture spot in the set of capture spots is (i) at a different position in a two-dimensional array and (ii) associates with one or more analytes from the sectioned tissue sample, and each respective capture spot in the set of capture spots is characterized by at least one unique spatial barcode in a plurality of spatial barcodes.

18. The method of claim 1, wherein a capture spot in the set of capture spots comprises a capture domain or a cleavage domain.

19. A computer system comprising:

one or more processors;

memory; and one or more programs, wherein the one or more programs are stored in the memory and configured to be executed by the one or more processors, the one or more programs for spatial analysis of analytes, the one or more programs including instructions for:

A) obtaining a data structure in electronic form comprising an image of a sample on a substrate, wherein:

the substrate includes a plurality of border regions, wherein each respective border region in the plurality of border regions intersects another border region in the plurality of border regions, the substrate includes at least a first plurality of fiducial markers, the first plurality of fiducial markers comprises at least three fiducial markers, each respective fiducial marker in the first plurality of fiducial markers encodes a different N-digit code, in a plurality of N-digit codes, wherein N is an integer greater than 3, at least two different border regions in the plurality of border regions includes a respective fiducial marker in the first plurality of fiducial markers, the substrate includes a set of capture spots, wherein the set of capture spots comprises at least 1000 capture spots, and the image comprises a plurality of pixel values, each respective pixel value in the plurality of pixel values corresponding to a pixel in an array of pixels, wherein the array of pixels comprises at least 100,000 pixels;

B) analyzing the plurality of pixel values to identify a respective location of each fiducial marker in the first plurality of fiducial markers within the image;

C) aligning the respective location of each fiducial marker in the first plurality of fiducial markers within the image with a location of each reference fiducial marker in a plurality of reference fiducial markers of a first template using an alignment algorithm to obtain a final transformation between the first plurality of fiducial markers of the image and the plurality of reference fiducial markers of the first template;

D) using the final transformation and a coordinate system of the first template to register the image to the set of capture spots; and E) analyzing the image after the using D) in conjunction with spatial analyte data associated with each capture spot, thereby performing spatial analysis of analytes.

20. A non-transitory computer readable storage medium storing one or more programs, the one or more programs comprising instructions, which when executed by an electronic device with one or more processors and a memory cause the electronic device to perform spatial analysis of analytes by a method comprising:

A) obtaining a data structure in electronic form comprising an image of a sample on a substrate, wherein: the substrate includes a plurality of border regions, wherein each respective border region in the plurality of border regions intersects another border region in the plurality of border regions, the substrate includes at least a first plurality of fiducial markers, the first plurality of fiducial markers comprises at least three fiducial markers, each respective fiducial marker in the first plurality of fiducial markers encodes a different N-digit code, in a plurality of N-digit codes, wherein N is an integer greater than 3, at least two different border regions in the plurality of border regions includes a respective fiducial marker in the first plurality of fiducial markers, the substrate includes a set of capture spots, wherein the set of capture spots comprises at least 1000 capture spots, and the image comprises a plurality of pixel values, each respective pixel value in the plurality of pixel values corresponding to a pixel in an array of pixels, wherein the array of pixels comprises at least 100,000 pixels;

B) analyzing the plurality of pixel values to identify a respective location of each fiducial marker in the first plurality of fiducial markers within the image;

C) aligning the respective location of each fiducial marker in the first plurality of fiducial markers within the image with a location of each reference fiducial marker in a plurality of reference fiducial markers of a first template using an alignment algorithm to obtain a final transformation between the first plurality of fiducial markers of the image and the plurality of reference fiducial markers of the first template;

D) using the final transformation and a coordinate system of the first template to register the image to the set of capture spots; and E) analyzing the image after the using D) in conjunction with spatial analyte data associated with each capture spot, thereby performing spatial analysis of analytes.

* * * * *